(12) United States Patent
Dack et al.

(10) Patent No.: US 8,278,343 B2
(45) Date of Patent: Oct. 2, 2012

(54) PYRROLIDINES

(75) Inventors: Kevin N. Dack, Sandwich (GB); James E. Mills, Sandwich (GB); Sarah E. Skerratt, Sandwich (GB)

(73) Assignee: Pfizer Inc., New York, NY (US)

( * ) Notice: Subject to any disclaimer, the term of this patent is extended or adjusted under 35 U.S.C. 154(b) by 295 days.

(21) Appl. No.: 12/613,771

(22) Filed: Nov. 6, 2009

(65) Prior Publication Data

US 2010/0120793 A1    May 13, 2010

Related U.S. Application Data

(60) Provisional application No. 61/112,869, filed on Nov. 10, 2008.

(51) Int. Cl.
*A01N 43/36* (2006.01)
*A61K 31/40* (2006.01)
(52) U.S. Cl. ........................... 514/423; 548/536
(58) Field of Classification Search ................ 548/536
See application file for complete search history.

(56) References Cited

U.S. PATENT DOCUMENTS

2007/0203222 A1    8/2007    Old et al. ................ 514/422

FOREIGN PATENT DOCUMENTS

| EP | 0525197 | 2/1993 |
|----|---------|--------|
| WO | WO 03053923 | 7/2003 |
| WO | WO 2007 005176 | 1/2007 |
| WO | WO 2007 140197 | 12/2007 |
| WO | WO 2008022725 A1 * | 2/2008 |
| WO | WO 2008 139287 | 11/2008 |

OTHER PUBLICATIONS

S.R. Byrn et al, Solid-State Chemistry of Drugs, 516 (2nd ed., 1999).*
B Testa et al., Prodrug Design in, 5 Encyclopedia of Pharmaceutical Technology, 3008-3014 (J. Swarbrick ed., 3rd ed., 2007).*
S.L. Morissette et al., Advanced Drug Delivery Reviews, 56, 275-300, 275 (2004).*
J. Aaltonen et al., European Journal of Pharmaceutics and Biopharmaceutics, 71, 23-37, 26 (2009).*
V. J. Stella, Prodrug Strategies for Improving Drug-Like Properties in, Optimizing the "Drug-Like" Properties of Leads in Drug Discovery 221-242, 224 (V.J. Stella et al., eds., 2006).*
Gavezzotti, Accounts of Chemical Research, 27, 309-314 (1994).*

* cited by examiner

*Primary Examiner* — James O Wilson
*Assistant Examiner* — Alexander R Pagano
(74) *Attorney, Agent, or Firm* — Richard V. Zanzalari

(57) ABSTRACT

This invention relates to a class of pyrrolidine compounds of formula (I), and pharmaceutically acceptable derivatives thereof, to their use in medicine, to compositions containing them, and to processes for their preparation. It also relates to intermediates used in the preparation of such compounds and derivatives. In particular the compounds of formula (I) are useful for the treatment of EP2-mediated conditions, such as endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome.

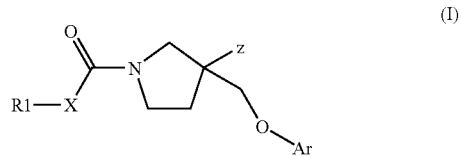

12 Claims, No Drawings

PYRROLIDINES

This application is a non-provisional filing which claims priority to U.S. Provisional Patent Application Ser. No. 61/112,869 filed Nov. 10, 2008.

This invention relates to a certain class of pyrrolidine compounds, and pharmaceutically acceptable derivatives thereof, to their use in medicine, to compositions containing them, and to processes for their preparation. It also relates to intermediates used in the preparation of such compounds and derivatives.

The compounds are preferably antagonists at the prostaglandin $E_2$ ($PGE_2$) receptor-2 (also known as the EP2 receptor). More preferably the compounds are EP2 antagonists with selectivity over DP1 (prostaglandin D1 receptor) and/or EP4 (prostaglandin $E_4$ ($PGE_4$) receptor-4). Most preferably the compounds are EP2 antagonists with selectivity over DP1 and EP4. In particular the present invention relates to a class of pyrrolidine compounds which should be useful for the treatment of EP2-mediated conditions, such as endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome.

Endometriosis is a common gynecological disease that affects 10-20% women of reproductive age and manifests itself in the presence of functional ectopic endometrial glands and stroma at locations outside the uterine cavity (reviewed in (Prentice 2001)). Patients with endometriosis may present with many different symptoms and severity. Most commonly this is dysmenorrhoea, but chronic pelvic pain, dyspareunia, dyschezia, menorrhagia, lower abdominal or back pain, infertility, bloating and pain on micturition are also part of the constellation of symptoms of endometriosis.

Originally described by Von Rokitansky in 1860 (Von Rokitansky 1860), the exact pathogenesis of endometriosis is unclear (Witz 1999; Witz 2002), but the most widely accepted theory is the implantation, or Sampson, theory (Sampson 1927). The Sampson theory postulates that the development of endometriosis is a consequence of retrograde dissemination and implantation of endometrial tissue into the peritoneal cavity during menstruation. Following attachment, the fragments of endometrium recruit a vascular supply and undergo cycles of proliferation and shedding under local and systemic hormonal controls. In women with patent fallopian tubes, retrograde menstruation appears to be a universal phenomenon (Liu & Hitchcock 1986). The disease often manifests itself as rectovaginal endometriosis or adenomyosis, ovarian cystic endometriomas and, most commonly, peritoneal endometriosis. The major sites of attachment and lesion growth within the pelvis are the ovaries, broad and round ligaments, fallopian tubes, cervix, vagina, peritoneum and the pouch of Douglas. At its most severe, endometriosis can cause profound structural modification to peritoneal cavity, including multi-organ adhesions and fibrosis.

Symptomatic endometriosis can be managed medically and surgically, where the intention is to remove the ectopic lesion tissue. Surgical intervention can be either conservative, aiming to preserve the reproductive potential of the patient, or comparatively radical for severe disease, involving dissection of the urinary tract, bowel, and rectovaginal septum, or total abdominal hysterectomy and bilateral salpingo-oophorectomy. Medical pharmacological treatments such as the androgenic therapies, danazol and gestrinone, the constellation of GnRH agonists, buserelin, goserelin, leuprolide, nafarelin and triptorelin, GnRH antagonists, cetrorelix and abarelix, as well as the progestogens, including medroxyprogesterone acetate, induce lesion atrophy by suppressing the production of estrogen. These approaches are not without unwanted side effects; danazol and gestrinone include weight gain, hirsuitism, acne, mood changes and metabolic effects on the cardiovascular system. The group of GnRH agonists and antagonists are found to cause a profound suppression of estrogen leading to vasomotor effects (hot flashes) and depletion of bone mineral density, which restricts their use to only six months of therapy.

Uterine leiomyomas (Walker 2002; Flake, et al. 2003), or fibroids, are the most common benign tumours found in women and occur in the majority of women by the time they reach the menopause. Although uterine fibroids are the most frequent indication for hysterectomy in the United States, as with endometriosis, remarkably little is known about the underlying pathophysiology of the disease. As with endometriotic lesions, the presence of enlarged uterine fibroids is associated with abnormal uterine bleeding, dysmenorrhoea, pelvic pain and infertility. Outside of surgical management, medical treatments commonly used for endometriosis, such as GnRH analogues or danazol, have been shown to suppress fibroid growth by inducing a reversible hypoestrogenic state (Chrisp & Goa 1990; Chrisp & Goa 1991; De Leo, et al. 2002; Ishihara, et al. 2003).

However, the future disease management of both uterine fibroids and endometriosis will rely on the development of more effective, well-tolerated and safer agents than those that are currently available. There are long term deleterious effects (principally altered sexual function, decreases in bone mineral density as well as increased risk of cardiovascular and thrombotic complications) of existing agents that completely suppress ovarian function and lead to decreases in bone mineral density, there is a motivation for developing non-hormonal mechanisms or approaches which modify the disease specifically at the level of the ectopic disease. One of these includes approaches includes agents which modify the cyclooxygenase-2 (COX-2) dependent $PGE_2$ signalling pathway (Boice & Rohrer 2005). $PGE_2$ mediates its effects through G protein-coupled receptors EP1, EP2, EP3 and EP4. Both the differential expression of EP receptors as well as their intracellular coupling pathways mediates the diverse biological functions of $PGE_2$ in different cell types (Narumiya, et al. 1999; Tilley, et al. 2001). The EP2 and EP4 receptors specifically couple to G proteins which activate adenylate cyclase and lead to the production of cAMP. In the uterine endometrium, COX-2 expression increases on glandular epithelium in the proliferative phase and is accompanied by an increase in EP2 and EP4 receptor expression (reviewed by (Sales & Jabbour 2003; Jabbour, et al. 2006)). In pathological conditions of the endometrium, such as endometrial adenocarcinoma, adenomyosis and endometriosis, this pathway appears to be up-regulated (Jabbour, et al. 2001; Ota, et al. 2001; Chishima, et al. 2002; Jabbour 2003; Matsuzaki, et al. 2004b; Buchweitz, et al. 2006). COX-2 plays an important role in ovulation, implantation, decidualisation and parturition (Sales & Jabbour 2003). Mice in which the EP2 receptor is deleted by homologous recombination have defects in embryo implantation and fertility (Hizaki, et al. 1999; Kennedy, et al. 1999; Tilley, et al. 1999), supporting the notion that COX-2 derived $PGE_2$ mediates effects on the uterine endometrium in part through the EP2 receptor. The expression of COX-2 is known to be greatly up-regulated at ectopic sites of disease, in contrast to that on normal eutopic endometrium (Ota, et al. 2001; Chishima, et al. 2002; Matsuzaki, et al. 2004b; Buchweitz, et al. 2006) and PGE2 induces the proliferation of endometrial epithelial cells in culture (Jabbour & Boddy 2003). In pre-clinical disease models of endometriosis, treatment with COX-2 selective agents, leads to the decrease in disease burden (Dogan, et al. 2004; Matsuzaki, et al. 2004a; Ozawa, et al. 2006; Laschke, et al. 2007). There is also one published clinical study (Cobellis, et al. 2004) which indicates that treatment of patients with endometriosis with rofecoxib for 6 months leads to improvements in pain symptoms and outcomes compared with placebo.

The aberrant expression of COX-2 in patients with endometriosis appears to have a number of consequences (Sales & Jabbour 2003). Firstly, $PGE_2$ appears to augment the expression and activity of aromatase on ectopic endometrial stromal cells (Noble, et al. 1997; Zeitoun & Bulun 1999). It could be speculated that ectopic generation of aromatase by the lesion would lead to increased local estrogen production, driving lesion growth independently of ovarian control and the normal estrous cycle. That the effects of $PGE_2$ on aromatase expression in vitro can be mimicked by the selective EP2 receptor agonist, butaprost (Zeitoun & Bulun 1999), supports the notion that compounds of the present invention would have utility in the treatment of growth disorders which are driven ectopic aromatase expression, such as endometriosis, adenomyomas, uterine fibroids as well as uterine and breast carcinoma.

There are other possible mechanisms by which a selective EP2 antagonist might inhibit cell growth. The observed effects of COX-2 inhibitors, such as celecoxib, in preventing intestinal polyp formation (Arber, et al. 2006) and the protection from adenoma formation in a mouse model ($\Delta^{716}$APC mouse) of familial adenomatous polyposis complex by deletion of COX-2 (Oshima, et al. 1996; Oshima, et al. 2001), implies that the $PGE_2$ pathway also has a key role in promoting carcinoma growth. That polyp and adenoma formation in the $\Delta^{716}$APC mouse model can also be inhibited by crossing these by additional germline deletion of the EP2 receptor, is consistent with the view that $PGE_2$ mediates effects on cell differentiation and growth through the EP2 receptor (Sonoshita, et al. 2001; Seno, et al. 2002). Furthermore, the emerging knowledge of the downstream signalling pathway from the EP2 receptor is consistent with EP2 playing a key role in early G1 events in cell cycle control, such as the regulation of β-catenin (Castellone, et al. 2005; Castellone, et al. 2006) and MAP kinase pathways (Jabbour & Boddy 2003).

Angiogenesis, the sprouting of capillaries from pre-existing vasculature, occurs during embryo development, wound repair and tumour growth. The increased COX-2 expression and vascular densities which accompany the development of adenomas in the $\Delta^{716}$APC mouse, are also consistently observed in clinical specimens and pre-clinical models of endometriosis and malignant conditions of, including but not limited to, ovarian, dermal, prostate, gastric, colorectal and breast cancer (Subbaramaiah, et al. 2002; Hull, et al. 2003; Kamiyama, et al. 2006). The involvement of the COX-2 pathway in this process has been supported by a number of observations (Liu, et al. 2001; Leahy, et al. 2002; Chang, et al. 2004; Ozawa, et al. 2006). The peritoneal fluid of women with endometriosis appears to display greater angiogenic activity than women without endometriosis (Gazvani & Templeton 2002; Bourlev, et al. 2006) and $PGE_2$ has been shown to promote the transcription of angiogenic factors such as VEGF and angiopoietins (reviewed in (Gately & Li 2004)). Recent data that indicate the specific contribution of EP2 receptors in the stimulation of endothelial cell growth and migration (Kamiyama, et al. 2006) as well as response to hypoxia (Critchley, et al. 2006), is consistent with and supports the notion that compounds of the present invention would have utility in the treatment of angiogenic disorders including, but not limited to, endometriosis, adenomyosis, leiomyoma, menorrhagia, macular degeneration, rheumatoid arthritis and cancer.

Both uterine nerve ablation and pre-sacral neurectomy surgical techniques are used to manage the painful symptoms of primary and secondary dysmenorrhoea (Proctor, et al. 2005). As $PGE_2$ is generated from $PGH_2$ by the action of COX-1 and COX-2 on arachadonic acid, elevated $PGE_2$ would have direct, pain-sensitizing effects on sensory afferent fibres that innervate the peritoneum and ectopic lesions (Tulandi, et al. 2001; Al-Fozan, et al. 2004; Berkley, et al. 2004; Quinn & Armstrong 2004; Tokushige, et al. 2006a; Tokushige, et al. 2006b). That elevated COX-2 expression correlates with non-menstrual chronic pelvic pain (Buchweitz, et al. 2006) is consistent with this notion. A number of lines of evidence from studies in mouse models suggest that one of the modes of action of $PGE_2$ on pain and nociception is mediated by the EP2 receptor (Ahmadi, et al. 2002; Reinold, et al. 2005; Hosl, et al. 2006). As such compounds of the present invention would have utility in the treatment of pain disorders including, but not limited to, dysmenorrhoea, dyschezia, dyspareunia, irritable bowel syndrome, endometriosis, adenomyosis, leiomyomata, CPP, interstitial cystitis, inflammatory and neuropathic pain conditions.

During the development of endometriosis activated inflammatory cells appear to be recruited into the peritoneal cavity. Peritoneal macrophages from women with endometriosis release more $PGE_2$ than those without endometriosis (Karck, et al. 1996; Wu, et al. 2005). One of the effects of elevated levels $PGE_2$ on peritoneal macrophages is to inhibit MMP-9 expression and thereby attenuate macrophage phagocytic function (Wu, et al. 2005), leading to the prolonged accumulation of endometrial tissue in the peritoneum. As such by restoring macrophage function, these findings give further support to the use of compounds of the present invention in the treatment of endometriosis and cancer.

Known EP2 antagonists include AH6809, (Pelletier, et al. 2001), but both its potency and selectivity fall short of being suitable for medical therapy.

S. Ahmadi, S. Lippross, W. L. Neuhuber & H. U. Zeilhofer. PGE2 selectively blocks inhibitory glycinergic neurotransmission onto rat superficial dorsal horn neurons. Nat Neurosci 5, 34-40 (2002).

H. Al-Fozan, S. Bakare, M.-F. Chen & T. Tulandi. Nerve fibers in ovarian dermoid cysts and endometriomas. Fertil Steril 82, 230-1 (2004).

N. Arber, C. J. Eagle, J. Spicak, I. Racz, P. Dite, J. Hajer, M. Zavoral, M. J. Lechuga, P. Gerletti, J. Tang, R. B. Rosenstein, K. Macdonald, P. Bhadra, R. Fowler, J. Wittes, A. G. Zauber, S. D. Solomon & B. Levin. Celecoxib for the prevention of colorectal adenomatous polyps. N Engl J. Med. 355, 885-95. (2006).

K. J. Berkley, N. Dmitrieva, K. S. Curtis & R. E. Papka. Innervation of ectopic endometrium in a rat model of endometriosis. PNAS 101, 11094-8 (2004).

J. A. Boice & S. Rohrer 2005 Use of selective cyclooxygenase-2 inhibitors for the treatment of endometriosis 2004-US19441 2005000238

V. Bourlev, N. Volkov, S. Pavlovitch, N. Lets, A. Larsson & M. Olovsson. The relationship between microvessel density, proliferative activity and expression of vascular endothelial growth factor-A and its receptors in eutopic endometrium and endometriotic lesions. Reproduction 132, 501-09 (2006).

O. Buchweitz, A. Staebler, P. Wuelfing, E. Hauzman, R. Greb & L. Kiesel. COX-2 overexpression in peritoneal lesions is correlated with non-menstrual chronic pelvic pain. European Journal of Obstetrics & Gynecology and Reproductive Biology 124, 216-21 (2006).

M. D. Castellone, H. Teramoto, B. O. Williams, K. M. Druey & J. S. Gutkind. Prostaglandin E2 promotes colon cancer cell growth Through a Gs-axin-b-catenin signaling axis. Science (Washington, D.C., United States) 310, 1504-10 (2005).

M. D. Castellone, H. Teramoto & J. S. Gutkind. Cyclooxygenase-2 and colorectal cancer chemoprevention: The beta-catenin connection. Cancer Research 66, 11085-88 (2006).

S.-H. Chang, C. H. Liu, R. Conway, D. K. Han, K. Nithipatikom, O. C. Trifan, T. F. Lane & T. Hla. From the Cover: Role of prostaglandin E2-dependent angiogenic switch in cyclooxygenase 2-induced breast cancer progression. PNAS 101, 591-96 (2004).

F. Chishima, S. Hayakawa, K. Sugita, N. Kinukawa, S. Aleemuzzaman, N. Nemoto, T. Yamamoto & M. Honda. Increased expression of cyclooxygenase-2 in local lesions of endometriosis patients. Am J Reprod Immunol 48, 50-6 (2002).

P. Chrisp & K. L. Goa. Nafarelin. A review of its pharmacodynamic and pharmacokinetic properties, and clinical potential in sex hormone-related conditions. Review 74 refs. Drugs 39, 523-51 (1990).

P. Chrisp & K. L. Goa. Goserelin. A review of its pharmacodynamic and pharmacokinetic properties, and clinical use in sex hormone-related conditions. Review 155 refs. Drugs 41, 254-88 (1991).

L. Cobellis, S. Razzi, S. De Simone, A. Sartini, A. Fava, S. Danero, W. Gioffre, M. Mazzini & F. Petraglia. The treatment with a COX-2 specific inhibitor is effective in the management of pain related to endometriosis. European Journal of Obstetrics & Gynecology and Reproductive Biology 116, 100-02 (2004).

H. O. D. Critchley, J. Osei, T. A. Henderson, L. Boswell, K. J. Sales, H. N. Jabbour & N. Hirani. Hypoxia-Inducible Factor-1{alpha} Expression in Human Endometrium and Its Regulation by Prostaglandin E-Series Prostanoid Receptor 2 (EP2). Endocrinology 147, 744-53 (2006).

V. De Leo, G. Morgante, A. La Marca, M. C. Musacchio, M. Sorace, C. Cavicchioli & F. Petraglia. A benefit-risk assessment of medical treatment for uterine leiomyomas. Drug Safety 25, 759-79 (2002).

E. Dogan, U. Saygili, C. Posaci, B. Tuna, S. Caliskan, S. Altunyurt & B. Saatli. Regression of endometrial explants in rats treated with the cyclooxygenase-2 inhibitor rofecoxib. Fertil Steril. 82 Suppl 3, 1115-20. (2004).

G. P. Flake, J. Andersen & D. Dixon. Etiology and pathogenesis of uterine leiomyomas: a review. Environmental Health Perspectives 111, 1037-54 (2003).

S. Gately & W. W. Li. Multiple roles of COX-2 in tumor angiogenesis: a target for antiangiogenic therapy. Seminars in Oncology 31, 2-11 (2004).

R. Gazvani & A. Templeton. Peritoneal environment, cytokines and angiogenesis in the pathophysiology of endometriosis. Reproduction 123, 217-26 (2002).

H. Hizaki, E. Segi, Y. Sugimoto, M. Hirose, T. Saji, F. Ushikubi, T. Matsuoka, Y. Noda, T. Tanaka, N. Yoshida, S. Narumiya & A. Ichikawa. Abortive expansion of the cumulus and impaired fertility in mice lacking the prostaglandin E receptor subtype EP2. PNAS 96, 10501-06 (1999).

K. Hosl, H. Reinold, R. J. Harvey, U. Muller, S. Narumiya & H. U. Zeilhofer. Spinal prostaglandin E receptors of the EP2 subtype and the glycine receptor [alpha]3 subunit, which mediate central inflammatory hyperalgesia, do not contribute to pain after peripheral nerve injury or formalin injection. Pain 126, 46-53 (2006).

M. L. Hull, D. S. Charnock-Jones, C. L. K. Chan, K. L. Bruner-Tran, K. G. Osteen, B. D. M. Tom, T.-P. D. Fan & S. K. Smith. Antiangiogenic Agents Are Effective Inhibitors of Endometriosis. J Clin Endocrinol Metab 88, 2889-99 (2003).

H. Ishihara, J. Kitawaki, N. Kado, H. Koshiba, S. Fushiki & H. Honjo. Gonadotropin-releasing hormone agonist and danazol normalize aromatase cytochrome P450 expression in eutopic endometrium from women with endometriosis, adenomyosis, or leiomyomas. Fertility & Sterility 79, 735-42 (2003).

H. N. Jabbour, S. A. Milne, A. R. Williams, R. A. Anderson & S. C. Boddy. Expression of COX-2 and PGE synthase and synthesis of PGE(2) in endometrial adenocarcinoma: a possible autocrine/paracrine regulation of neoplastic cell function via EP2/EP4 receptors. Br J Cancer. 85, 1023-31. (2001).

H. N. Jabbour 2003 Use of prostaglandin E synthase inhibitors, or EP2 or EP4 receptor antagonists, in the treatment of a pathological condition of the uterus 2002-GB4549 2003030911

H. N. Jabbour & S. C. Boddy. Prostaglandin E2 Induces Proliferation of Glandular Epithelial Cells of the Human Endometrium via Extracellular Regulated Kinase 1/2-Mediated Pathway. J Clin Endocrinol Metab 88, 4481-87 (2003).

H. N. Jabbour, K. J. Sales, O. P. Smith, S. Battersby & S. C. Boddy. Prostaglandin receptors are mediators of vascular function in endometrial pathologies. Mol Cell Endocrinol. 252, 191-200 (2006).

M. Kamiyama, A. Pozzi, L. Yang, L. M. DeBusk, R. M. Breyer & P. C. Lin. EP2, a receptor for PGE2, regulates tumor angiogenesis through direct effects on endothelial cell motility and survival. Oncogene 25, 7019-28 (2006).

U. Karck, F. Reister, W. Schafer, H. P. Zahradnik & M. Breckwoldt. PGE2 and PGF2 alpha release by human peritoneal macrophages in endometriosis. Prostaglandins. 51, 49-60. (1996).

C. R. J. Kennedy, Y. Zhang, S. Brandon, Y. Guan, K. Coffee, C. D. Funk, M. A. Magnuson, J. A. Oates, M. D. Breyer & R. M. Breyer. Salt-sensitive hypertension and reduced fertility in mice lacking the prostaglandin EP2 receptor. Nat Med 5, 217-20 (1999).

M. W. Laschke, A. Elitzsch, C. Scheuer, B. Vollmer & M. D. Menger. Selective cyclo-oxygenase-2 inhibition induces regression of autologous endometrial grafts by down-regulation of vascular endothelial growth factor-mediated angiogenesis and stimulation of caspase-3-dependent apoptosis. Fertility and Sterility 87, 163-71 (2007).

K. M. Leahy, R. L. Ornberg, Y. Wang, B. S. Zweifel, A. T. Koki & J. L. Masferrer. Cyclooxygenase-2 Inhibition by Celecoxib Reduces Proliferation and Induces Apoptosis in Angiogenic Endothelial Cells in Vivo. Cancer Res 62, 625-31 (2002).

C. H. Liu, S.-H. Chang, K. Narko, O. C. Trifan, M.-T. Wu, E. Smith, C. Haudenschild, T. F. Lane & T. Hla. Overexpression of Cyclooxygenase-2 Is Sufficient to Induce Tumorigenesis in Transgenic Mice. J. Biol. Chem. 276, 18563-69 (2001).

D. T. Liu & A. Hitchcock. Endometriosis: its association with retrograde menstruation, dysmenorrhoea and tubal pathology. British Journal of Obstetrics & Gynaecology 93, 859-62 (1986).

S. Matsuzaki, *M. Canis*, C. Darcha, R. Dallel, K. Okamura & G. Mage. Cyclooxygenase-2 selective inhibitor prevents implantation of eutopic endometrium to ectopic sites in rats. Fertility and Sterility 82, 1609-15 (2004a).

S. Matsuzaki, M. Canis, J.-L. Pouly, A. Wattiez, K. Okamura & G. Mage. Cyclooxygenase-2 expression in deep endometriosis and matched eutopic endometrium. Fertility and Sterility 82, 1309-15 (2004b).

S. Narumiya, Y. Sugimoto & F. Ushikubi. Prostanoid receptors: structures, properties, and functions. Physiol Rev. 79, 1193-226. (1999).

L. S. Noble, K. Takayama, K. M. Zeitoun, J. M. Putman, D. A. Johns, M. M. Hinshelwood, V. R. Agarwal, Y. Zhao, B. R. Carr & S. E. Bulun. Prostaglandin E2 stimulates aromatase expression in endometriosis-derived stromal cells. Journal of Clinical Endocrinology and Metabolism 82, 600-06 (1997).

M. Oshima, J. E. Dinchuk, S. L. Kargman, H. Oshima, B. Hancock, E. Kwong, J. M. Trzaskos, J. F. Evans & M. M. Taketo. Suppression of intestinal polyposis in Apc D716 knockout mice by inhibition of cyclooxygenase 2 (COX-2). Cell 87, 803-9 (1996).

M. Oshima, N. Murai, S. Kargman, M. Arguello, P. Luk, E. Kwong, M. M. Taketo & J. F. Evans. Chemoprevention of intestinal polyposis in the ApcD716 mouse by rofecoxib, a specific cyclooxygenase-2 inhibitor. Cancer Res 61, 1733-40 (2001).

H. Ota, S. Igarashi, M. Sasaki & T. Tanaka. Distribution of cyclooxygenase-2 in eutopic and ectopic endometrium in endometriosis and adenomyosis. Hum Reprod. 16, 561-6. (2001).

Y. Ozawa, T. Murakami, M. Tamura, Y. Terada, N. Yaegashi & K. Okamura. A selective cyclooxygenase-2 inhibitor suppresses the growth of endometriosis xenografts via antiangiogenic activity in severe combined immunodeficiency mice. Fertility and Sterility 86, 1146-51 (2006).

S. Pelletier, J. Dube, A. Villeneuve, F. Gobeil, Q. Yang, B. Battistini, G. Guillemette & P. Sirois. Prostaglandin E2 increases cyclic AMP and inhibits endothelin-1 production/secretion by guinea-pig tracheal epithelial cells through EP4 receptors. Br J Pharmacol 132, 999-1008 (2001).

A. Prentice. Regular review: Endometriosis. BMJ 323, 93-5 (2001).

M. L. Proctor, P. M. Latthe, C. M. Farquhar, K. S. Khan & N. P. Johnson. Surgical interruption of pelvic nerve pathways for primary and secondary dysmenorrhoea. Cochrane Database Syst Rev CD001896 (2005).

M. Quinn & G. Armstrong. 932-3 (Department of Obstetrics and Gynaecology, Hope Hospital, Manchester, UK., England: United Kingdom, 2004).

H. Reinold, S. Ahmadi, U. B. Depner, B. Layh, C. Heindl, M. Hamza, A. Pahl, K. Brune, S. Narumiya, U. Muller & H. U. Zeilhofer. Spinal inflammatory hyperalgesia is mediated by prostaglandin E receptors of the EP2 subtype. J. Clin. Invest. 115, 673-79 (2005).

K. J. Sales & H. N. Jabbour. Cyclooxygenase enzymes and prostaglandins in pathology of the endometrium. Reproduction 126, 559-67 (2003).

J. A. Sampson. Peritoneal endometriosis due to menstrual dissemination of endometrial tissue into the peritoneal cavity. American Journal of Obstetrics & Gynecology 14, 422-9 (1927).

H. Seno, M. Oshima, T.-O. Ishikawa, H. Oshima, K. Takaku, T. Chiba, S. Narumiya & M. M. Taketo. Cyclooxygenase 2- and prostaglandin E2 receptor EP2-dependent angiogenesis in ApcD716 mouse intestinal polyps. Cancer Research 62, 506-11 (2002).

M. Sonoshita, K. Takaku, N. Sasaki, Y. Sugimoto, F. Ushikubi, S. Narumiya, M. Oshima & M. M. Taketo. Acceleration of intestinal polyposis through prostaglandin receptor EP2 in ApcD716 knockout mice. Nature Medicine (New York, N.Y., United States) 7, 1048-51 (2001).

K. Subbaramaiah, L. Norton, W. Gerald & A. J. Dannenberg. Cyclooxygenase-2 Is Overexpressed in HER-2/neu-positive Breast Cancer. EVIDENCE FOR INVOLVEMENT OF AP-1 AND PEA3. J. Biol. Chem. 277, 18649-57 (2002).

S. L. Tilley, L. P. Audoly, E. H. Hicks, H.-S. Kim, P. J. Flannery, T. M. Coffman & B. H. Koller. Reproductive failure and reduced blood pressure in mice lacking the EP2 prostaglandin E2 receptor. J. Clin. Invest. 103, 1539-45 (1999).

S. L. Tilley, T. M. Coffman & B. H. Koller. Mixed messages: modulation of inflammation and immune responses by prostaglandins and thromboxanes. J Clin Invest. 108, 15-23. (2001).

N. Tokushige, R. Markham, P. Russell & I. S. Fraser. Nerve fibres in peritoneal endometriosis. Human Reproduction 21, 3001-07 (2006a).

N. Tokushige, R. Markham, P. Russell & I. S. Fraser. High density of small nerve fibres in the functional layer of the endometrium in women with endometriosis. Hum Reprod 21, 782-7 (2006b).

T. Tulandi, A. Felemban & M. F. Chen. Nerve fibers and histopathology of endometriosis-harboring peritoneum. J Am Assoc Gynecol Laparosc 8, 95-8 (2001).

C. Von Rokitansky. Ueber uterusdruesen-neubildung in uterus and ovarial sarcomen. Ztsch K K Gesellsch der Aerzte zu Wien 37, 577-81 (1860).

C. L. Walker. Role of hormonal and reproductive factors in the etiology and treatment of uterine leiomyoma. Recent Progress in Hormone Research 57, 277-94 (2002).

C. A. Witz. Current concepts in the pathogenesis of endometriosis. Clinical Obstetrics & Gynecology 42, 566-85 (1999).

C. A. Witz. Pathogenesis of endometriosis. Gynecologic & Obstetric Investigation 53, 52-62 (2002).

M. H. Wu, Y. Shoji, M. C. Wu, P. C. Chuang, C. C. Lin, M. F. Huang & S. J. Tsai. Suppression of matrix metalloproteinase-9 by prostaglandin E(2) in peritoneal macrophage is associated with severity of endometriosis. Am J Pathol. 167, 1061-9. (2005).

K. M. Zeitoun & S. E. Bulun. Aromatase: a key molecule in the pathophysiology of endometriosis and a therapeutic target. Fertility and Sterility 72, 961-69 (1999).

The compounds of the present invention have been found to have potentially useful pharmaceutical properties. Their potential use includes, but is not limited to, EP2 antagonist properties, which should be useful in the treatment of endometriosis, uterine fibroids (leiomyomata) and menorrhagia, adenomyosis, primary and secondary dysmenorrhoea (including symptoms of dyspareunia, dyschexia and chronic pelvic pain), chronic pelvic pain syndrome, precocious puberty, cervical ripening, breast carcinoma, colon carcinoma, familial adenomatous polyposis, colorectal adenomas, endometrial carcinoma, prostate carcinoma, pulmonary carcinoma, testicular carcinoma, gastric carcinoma, macular degeneration, inflammatory and neuropathic pain conditions, cancer pain.

Particularly of interest are the following diseases or disorders: endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome.

In particular, the compounds and derivatives of the present invention exhibit activity as prostaglandin $E_2$ ($PGE_2$) receptor-2 (EP2) antagonists and may be useful for treatment where EP2 receptor antagonism is indicated.

More particularly, the compounds and derivatives of the present invention may be useful for treating endometriosis and/or uterine fibroids (leiomyomata).

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with the indications mentioned above. The treatment may be a pre-treatment as well as a treatment at the on-set of symptoms.

The present invention provides for compounds of formula (I):

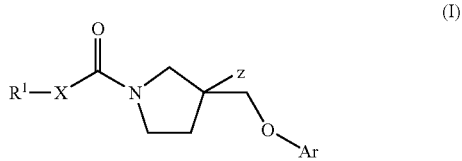

(I)

wherein:
$R^1$ is a phenyl group optionally substituted by one or two substituents independently selected from F, Cl, Br, CN, $C_{1-4}$ alkyl, $C_{1-4}$ alkylthio and $C_{1-4}$ alkoxy, fluoro-$C_{1-6}$ alkyl and fluoro-$C_{1-6}$ alkoxy, or a $C_{3-6}$ cycloalkyl group;
X represents a direct link, NH, or O;
Z is selected from

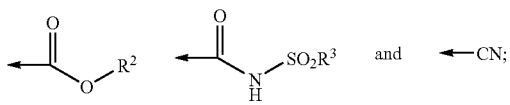

$R^2$ is H or $C_{1-6}$ alkyl (optionally substituted with 1 to 3 fluorine atoms);
$R^3$ is $C_{1-6}$ alkyl (optionally substituted with 1 to 3 fluorine atoms);
Ar is an aromatic group consisting of 1, 2 or 3 aromatic rings, which aromatic rings are independently selected from phenyl and a 5- or 6-membered heteroaromatic ring containing 1, 2, 3 or 4 heteroatoms independently selected from N, O and S, and which aromatic rings, if there are 2 or more, can be fused or linked by one or more covalent bond, and which aromatic rings are optionally substituted by 1, 2 or 3 substitutents independently selected from F, Cl, CN, OH, $C_{1-6}$ alkyl, $C_{1-6}$ alkylthio, fluoro-$C_{1-6}$ alkyl, fluoro-$C_{1-6}$ alkylthio, fluoro-$C_{1-6}$ alkoxy, $C_{1-6}$ alkoxy, $SO_2R^4$, $NR^5R^6$, $NHSO_2R^7$, $SO_2NR^8R^9$, $CONR^{10}R^{11}$ and $NHCOR^{12}$;
$R^4$ and $R^7$ are each independently $C_{1-6}$ alkyl (optionally substituted by 1 to 3 fluorine atoms);
$R^5$, $R^6$, $R^8$, $R^9$, $R^{10}$, $R^{11}$ and $R^{12}$ are each independently H or $C_{1-6}$ alkyl (optionally substituted by 1 to 3 fluorine atoms);
or a pharmaceutically acceptable salt, solvate (including hydrate), or prodrug thereof.

Unless otherwise indicated, alkyl and alkoxy groups may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy. Fluoroalkyl and fluoroalkoxy means, respectively, alkyl and alkoxy each independently substituted by 1 to 3 fluorine atoms. The term "$C_3$-$C_6$ cycloalkyl" means cyclopropyl, cyclobutyl, cyclopentyl or cyclohexyl.

In a further embodiment, $R^1$ is a phenyl group optionally substituted by one or two substituents independently selected from F, Cl and $C_{1-4}$ alkoxy, or a $C_{3-6}$ cycloalkyl group.

In a yet further embodiment, $R^1$ is a phenyl group optionally substituted by F, Cl, methoxy or ethoxy.

In a yet further embodiment, $R^1$ is 4-chlorophenyl, 4-fluorophenyl, phenyl, 3-chlorophenyl, 2-ethoxyphenyl, 2-methoxyphenyl, 3-methoxyphenyl, 3-ethoxyphenyl, 4-methoxyphenyl or 4-ethoxyphenyl.

In a yet further embodiment, $R^1$ is 4-methoxyphenyl or 4-fluorophenyl.

In an alternative embodiment, $R^1$ is selected from the values associated with the Examples below.

In a further embodiment, X is a direct link.
In a further embodiment, Z is

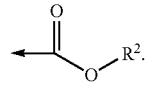

In a yet further embodiment, Z is $CO_2H$.

In a further embodiment, Ar is an aromatic group consisting of 1, 2 or 3 aromatic rings, which aromatic rings are independently selected from phenyl and a 5- or 6-membered heteroaromatic ring comprising either (a) 1 to 4 nitrogen atoms, (b) one oxygen or one sulphur atom or (c) 1 oxygen atom or 1 sulphur atom and 1 or 2 nitrogen atoms; and which aromatic rings, if there are 2 or more, can be fused or linked by one or more covalent bond, and which aromatic rings are optionally substituted by 1, 2 or 3 substitutents independently selected from F, Cl, CN, OH, $C_{1-6}$ alkyl, $C_{1-6}$ alkylthio, fluoro-$C_{1-6}$ alkyl, fluoro-$C_{1-6}$ alkylthio, fluoro-$C_{1-6}$ alkoxy, $C_{1-6}$ alkoxy, $SO_2R^4$, $NR^5R^6$, $NHSO_2R^7$, $SO_2NR^8R^9$, $CONR^{10}R^{11}$ and $NHCOR^{12}$.

In a further embodiment, Ar is a biphenyl, pyridinylphenyl, pyrimidinylphenyl or pyrazinylphenyl group, optionally substituted by 1, 2 or 3 substitutents independently selected from F, Cl, CN, OH, $C_{1-6}$ alkyl, $C_{1-6}$ alkylthio, per-fluoro-$C_{1-6}$ alkyl, perfluoro-$C_{1-6}$ alkylthio, perfluoro-$C_{1-6}$ alkoxy, $C_{1-6}$ alkoxy, $SO_2R^4$, $NR^5R^6$, $NHSO_2R^7$, $SO_2NR^8R^9$, $CONR^{10}R^{11}$ and $NHCOR^{12}$.

In a yet further embodiment, Ar is a biphenyl, pyridinylphenyl, pyrimidinylphenyl or pyrazinylphenyl optionally substituted by 1, 2 or 3 substitutents independently selected from F, Cl, CN, and a $C_{1-6}$ alkoxy group.

In a yet further embodiment, Ar is a biphenyl, pyridinylphenyl, pyrimidinylphenyl or pyrazinylphenyl or naphthyl group, substituted by F, Cl, CN, methoxy or ethoxy.

In a yet further embodiment, Ar is selected from

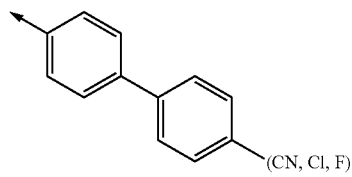

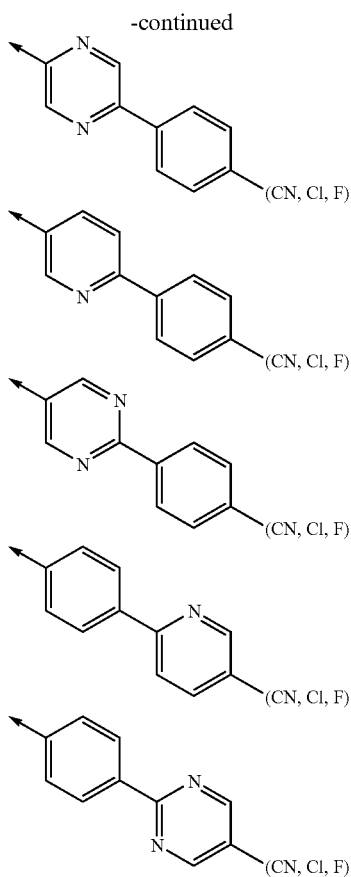

In an alternative embodiment Ar is selected from the values associated with the Examples below.

A preferred group of compounds, salts, solvates and prodrugs are those wherein $R^1$, Z and Ar have the values associated with the compounds of the Examples below.

In one embodiment, the present invention provides a compound of formula (Ia)

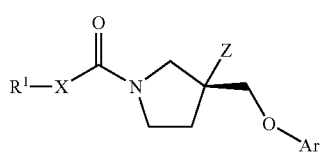

wherein $R^1$, X, Ar and Z are as defined hereinabove with respect to a compound of formula (I), including all embodiments, and combinations of particular embodiments, thereof.

In another embodiment, the present invention provides a compound of formula (Ib)

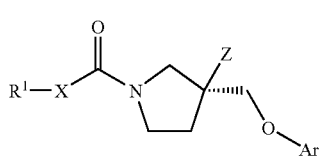

wherein $R^1$, X, Ar and Z are as defined hereinabove with respect to a compound of formula (I), including all embodiments, and combinations of particular embodiments, thereof.

A more preferred group of compounds, salts, solvates and prodrugs are the compounds of the Examples below (especially Examples 1, 2, 5, 10, 16, 17, 26, 28, 30, 32, 34, 50); and their salts, solvates and prodrugs.

The pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemi-salts of acids and bases may also be formed, for example, hemi-sulphate and hemicalcium salts.

For a review on suitable salts, see "Handbook of Pharmaceutical Salts: Properties, Selection, and Use" by Stahl and Wermuth (Wiley-VCH, 2002).

Pharmaceutically acceptable salts of compounds of formula I may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by RC Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In the general synthetic methods below, unless otherwise specified, the substituents $R^1$, Z and Ar are as defined above with reference to the compounds of formula (I) above.

The routes below illustrate methods of synthesising compounds of formula (I). The skilled person will appreciate that other methods may be equally as viable.

Scheme 1 illustrates the preparation of compounds of formula (I) via ether formation from intermediates (II) and (III), if necessary adding a suitable base (such as potassium carbonate) and/or additive (such as sodium iodide), and a suitable solvent, where LG in (II) is a suitable leaving group. Suitable leaving groups include, but are not limited to, Cl, Br, I, mesylate and tosylate.

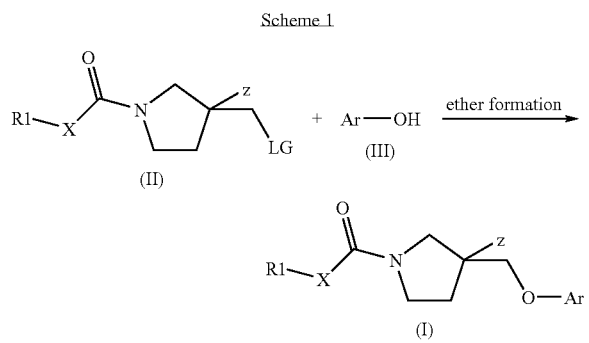

Typical conditions employed involve stirring the pyrrolidine of general formula (II) and the hydroxy-aryl compound of general formula (III) together with potassium carbonate, cesium carbonate or 1,8-diazobicyclo[5.4.0]undec-7-ene (DBU) in dimethyl sulphoxide (DMSO), dimethylformamide (DMF) or acetonitrile at a temperature from room temperature up to the reflux temperature of the solvent. A suitable alternative is to use an additive (such as sodium iodide, tetrabutyl ammonium iodide) as well as a base. Any suitable solvent may be used in place of those mentioned above. At least one equivalent of the intermediate hydroxyaryl compound (III) and at least one equivalent of the base should be used and an excess of one or both may be used if desired. Where Z is $C(O)O(C_{1-6}$ alkyl) in intermediate (II), if $Z=CO_2H$ of (I) is desired the hydrolysis can be done in situ, adding a suitable base or water to the reaction mixture after the ether formation has taken place. Suitable bases for this hydrolysis include lithium hydroxide or sodium hydroxide.

Scheme 2 illustrates the route for preparation of the pyrrolidine intermediates of general formula (II) from protected intermediates of general formula (IV) wherein PG is a suitable N-protecting group. Any suitable nitrogen protecting group may be used (as described in "Protecting Groups in Organic Synthesis" 3$^{rd}$ edition T. W. Greene and P. G. Wuts, Wiley-Interscience, 1999). Common nitrogen protecting groups (PG) suitable for use herein include tert-butoxycarbonyl (t-Boc), which is readily removed by treatment with an acid such as trifluoroacetic acid or hydrogen chloride in an organic solvent such as dichloromethane or 1,4-dioxane, and benzyl, which is readily removed by hydrogenation in the presence of a suitable catalyst or by treatment with 1-chloroethyl chloroformate.

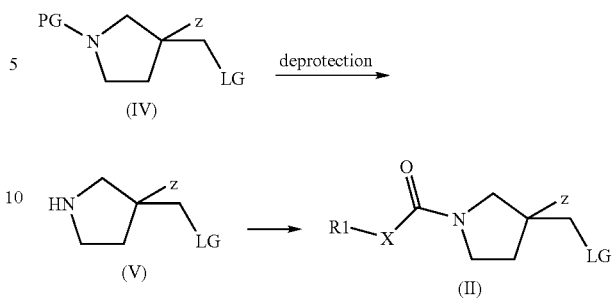

Compounds of formula (IV) can be made by methods well-known to those skilled in the art, for example with reference to literature precedents and/or the preparations herein, or routine adaptation thereof.

The compound of general formula (V) can be made by removal of the N-protecting group (PG). For example if PG is a benzyl group, it can be readily removed by hydrogenation in the presence of a suitable catalyst or by treatment with 1-chloroethyl chloroformate, or if PG is a benzamide group, it can be readily removed by refluxing in aqueous acid solution.

Wherein X represents a direct link, the $C(O)R^1$ group may be introduced by acylation of the intermediate (V) using standard acylation chemistry, such as with a suitable (activated) acid such as an acid chloride $R^1COCl$ or anhydride ($R^1CO_2O$ to provide the compounds of general formula (II). The acylation is preferably carried out using the acid chloride with a suitable base, such as triethylamine in a solvent such as dichloromethane, 1,2 dichloroethane or tetrahydrofuran. Acid chlorides $R^1COCl$ are either commercially available or will be well-known to those skilled in the art with reference to literature precedents.

Wherein X represents —NH—, the $C(O)NHR^1$ group may be introduced by reaction of the intermediates of formula (V) with a suitable isocyanate $R^1NCO$ to provide the compounds of formula (II). The urea formation is preferably carried out using the isocyanate with a suitable base, such as triethylamine, in a solvent, such as dichloromethane, 1,2 dichloroethane or tetrahydrofuran. Isocyanates $R^1NCO$ are either commercially available of will be well-known to those skilled in the art with reference to literature precedents.

Wherein X represents —O—, standard carbamate chemistry may be used to introduce the $C(O)OR^1$ group. The carbamate formation is preferably carried out using the appropriate chlorocarbamate, $R^1O(CO)Cl$, and intermediates of formula (V) with a suitable base, such as sodium hydrogen carbonate, in a solvent, such as dichloromethane, 1,2 dichloroethane or tetrahydrofuran to provide compounds of formula (II). Chlorocarbonates $R^1O(CO)Cl$ are either commercially available of will be well-known to those skilled in the art with reference to literature precedents.

Reagents/intermediates of general formula (III) are either commercially available or will be well-known to those skilled in the art with reference to literature precedents and/or the preparations herein.

Scheme 3 illustrates the route used to for prepare compounds of general formula (I), in which the pyrrolidine nitrogen is protected and $C(O)XR^1$ is introduced in the final step.

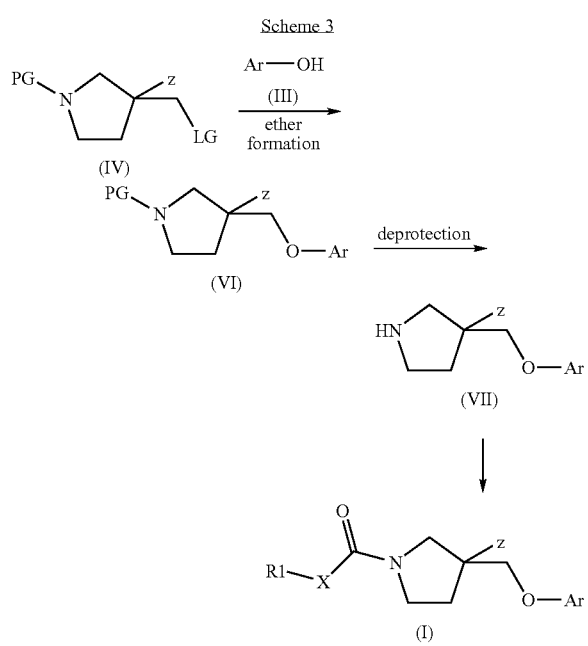

In Scheme 3 the intermediate of general formula (IV) is reacted in an etherification reaction as previously described in Scheme 1 to provide a protected intermediate (VI) from which the nitrogen protecting group can be removed using standard de-protection strategies to furnish a compound of general formula (VII). Any suitable nitrogen protecting group may be used (as described in "Protecting Groups in Organic Synthesis" $3^{rd}$ edition T. W. Greene and P. G. Wuts, Wiley-Interscience, 1999).

The C(O)XR$^1$ group may be introduced by acylation of the deprotected intermediate (VII), as previously described in Scheme 2. If X=bond, this can be done preferably via an acid chloride with a suitable base, such as triethylamine in a solvent such as dichloromethane, 1,1 dichloroethane or tetrahydrofuran. If X=—O—, this is preferably carried out using the appropriate chlorocarbamate, R$^1$O(CO)Cl, with a suitable base, such as sodium hydrogen carbonate, in a solvent, such as dichloromethane, 1,2 dichloroethane or tetrahydrofuran. If X=—NH—, this can be done preferably via an isocyanate with a suitable base, such as triethylamine, in a solvent, such as dichloromethane, 1,2 dichloroethane or tetrahydrofuran.

Intermediates of formula (VII) can be made from intermediates of formula (VI) described in Scheme 2, where the pyrrolidine can be protected with a suitable nitrogen protecting group (PG), where the preferred protecting groups are t-Boc, benzyl or benzamide.

According to a further embodiment the present invention provides novel intermediate compounds of general formula (II), (III), (IV), (V), (VI), (VII).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see "Polymorphism in Pharmaceutical Solids" by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

As indicated above, so-called 'prodrugs' of the compounds of formula (I) are also within the scope of the invention. Thus certain derivatives of compounds of formula (I), which may have little or no pharmacological activity themselves, can be converted into compounds of formula I having the desired activity, for example by hydrolytic cleavage, when administered into, or onto, the body. Such derivatives are referred to as 'prodrugs'. Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (Ed. E. B. Roche, American Pharmaceutical Association).

Prodrugs in accordance with the invention can be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include
(i) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and
(ii) where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Thus within the scope of the invention are envisaged the metabolites of the compounds of formula (I) when formed in vivo.

Compounds of formula (I) contain one or more asymmetric carbon atoms and can therefore exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{15}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention may be administered alone or in combination with one or more other compounds of the invention or in combination with one or more other drugs (or as any combination thereof).

The compounds of the present invention may be administered in combination with PDE5 inhibitors. Thus in a further aspect of the invention, there is provided a pharmaceutical product containing an EP2 antagonist and one or more PDEV inhibitors as a combined preparation for simultaneous, separate or sequential use in the treatment of endometriosis.

PDEV inhibitors useful for combining with compounds of the present invention include, but are not limited to:

(i) Preferably 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil, e.g. as sold as Viagra®) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxy phenyl]-2-(pyridin-2-yl)methyl-2,6-dihydro-7H-pyrazolo[4,3-d]pyrimidin-7-one (see WO 98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxy ethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)pyrazino[2',1':6,1]pyrido[3,4-b]indole-1,4-dione (tadalafil, IC-351, Clalis®), i.e. the compound of examples 78 and 95 of published international application WO95/19978, as well as the compound of examples 1, 3, 7 and 8; 2-[2-ethoxy-5-(4-ethylpiperazin-1-yl-1-sulphonyl)-phenyl]-5-methyl-7-propyl-3H-imidazo[5,1-f][1,2,4]triazin-4-one (vardenafil, LEVITRA®) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 of published international application WO93/07124 (EISAI); compounds 3 and 14 from Rotella D P, *J. Med. Chem.*, 2000, 43, 1257; 4-(4-chlorobenzyl)amino-6,7,8-trimethoxyquinazoline; N-[[3-(4,7-dihydro-1-methyl-7-oxo-3-propyl-1H-pyrazolo[4,3-d]-pyrimidin-5-yl)-4-propxyphenyl]sulfonyl]-1-methyl-2-pyrrolidine propanamide ["DA-8159" (Example 68 of WO00/27848)]; and 7,8-dihydro-8-oxo-6-[2-propoxyphenyl]-1H-imidazo[4,5-g]quinazoline and 1-[3-[1-[(4-fluorophenyl)methyl]-7,8-dihydro-8-oxo-1H-imidazo[4,5-g]quinazolin-6-yl]-4-propoxyphenyl] carboxamide; 4-[(3-chloro-4-methoxybenzyl)amino]-2-[(2S)-2-(hydroxymethyl)pyrrolidin-1-yl]N-(pyrimidin-2-ylmethyl)pyrimidine-5-carboxamide (TA-1790); 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzene sulfonamide (DA 8159) and pharmaceutically acceptable salts thereof.

(ii) 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, mono-sodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propyl indole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; I-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer); FR229934 and FR226807 (Fujisawa); and Sch-51866.

Preferably the PDEV inhibitor is selected from sildenafil, tadalafil, vardenafil, DA-8159 and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one. Most preferably the PDE5 inhibitor is sildenafil and pharmaceutically acceptable salts thereof. Sildenafil citrate is a preferred salt.

The compounds of the present invention may be administered in combination with a V1a antagonist. Thus, in a further aspect of the invention, there is provided a pharmaceutical product containing an EP2 receptor antagonist and one or more V1a antagonists as a combined preparation for simultaneous, separate or sequential use in the treatment of endometriosis.

A suitable vasopressin V1a receptor antagonist is, for example, (4-[4-Benzyl-5-(4-methoxy-piperidin-1-ylmethyl)-4H[1,2,4]triazol-3-yl]-3,4,5,6-tetrahydro-2H-[1,2]bipyridinyl), which is Example 26 in WO 2004/37809. A further example of a suitable vasopressin V1a receptor antagonist is 8-chloro-5-Methyl-1-(3,4,5,6-tetrahydro-2H-[1,2']bipyridinyl-4-yl)-5,6-dihydro-4H-2,3,5,10b-tetraazobenzo[e]azulene, or a pharmaceutically acceptable salt or solvate thereof, which is Example 5 in WO 04/074291.

Further examples of vasopressin V1a receptor antagonists for use with the invention are: SR49049 (Relcovaptan), atosiban (Tractocile®), conivaptan (YM-087), VPA-985, CL-385004, Vasotocin and OPC21268. Additionally, the V1a receptor antagonists described in WO 01/58880 are suitable for use in the invention.

The compounds of the present invention may be administered in combination with an agent which lowers estrogen levels, or which antagonises the estrogen receptor. Thus, in a further aspect of the invention, there is provided a pharmaceutical product containing a progesterone receptor antagonist and one or more agents which lower estrogen levels, or antagonise the estrogen receptor, as a combined preparation for simultaneous, separate or sequential use in the treatment of endometriosis.

Agents which lower estrogen levels include gonadotropin releasing hormone (GnRH) agonists, GnRH antagonists and estrogen synthesis inhibitors. Agents which antagonise the estrogen receptor, i.e. estrogen receptor antagonists, include anti-estrogens.

GnRH agonists suitable for the present invention include leuprorelin (Prostap—Wyeth), buserelin (Suprefact—Shire), goserelin (Zoladex—Astra Zeneca), triptorelin (De-capeptyl—Ipsen), nafarelin (Synarel—Searle), deslorelin (Somagard—Shire), and histrelin/supprelin (Ortho Pharmaceutical Corp/Shire).

GnRH antagonists suitable for the present invention include teverelix (also known as antarelix), abarelix (Plenaxis—Praecis Pharmaceuticals Inc.), cetrorelix (Cetrotide—ASTA Medica), and ganirelix (Orgalutran—Organon).

Anti-estrogens suitable for the present invention include tamoxifen, Faslodex (Astra Zeneca), idoxifene (see Coombes et al. (1995) Cancer Res. 55, 1070-1074), raloxifene or EM-652 (Labrie, F et al, (2001) J steroid Biochem Mol Biol, 79, 213).

Estrogen synthesis inhibitors suitable for the present invention include aromatase inhibitors. Examples of aromatase inhibitors include Formestane (4-OH androstenedione), Exemestane, Anastrozole (Arimidex) and Letroxole.

The compounds of the present invention may be administered in combination with an alpha-2-delta ligand. Thus, in a further aspect of the invention, there is provided a pharmaceutical product containing a progesterone receptor antagonist and one or more alpha-2-delta ligands, as a combined preparation for simultaneous, separate or sequential use in the treatment of endometriosis.

Examples of alpha-2-delta ligands for use in the present invention are those compounds, or pharmaceutically acceptable salts thereof, generally or specifically disclosed in U.S. Pat. No. 4,024,175, particularly gabapentin, EP641330, particularly pregabalin, U.S. Pat. No. 5,563,175, WO-A-97/33858, WO-A-97/33859, WO-A-99/31057, WO-A-99/31074, WO-A-97/29101, WO-A-02/085839, particularly [(1R,5R,6S)-6-(aminomethyl)bicyclo[3.2.0]hept-6-yl]acetic acid, WO-A-99/31075, particularly 3-(1-aminomethyl-cyclohexylmethyl)-4H-[1,2,4]oxadiazol-5-one and C-[1-(1H-tetrazol-5-ylmethyl)-cycloheptyl]-methylamine, WO-A-99/21824, particularly (3S,4S)-(1-aminomethyl-3,4-dimethyl-cyclopentyl)-acetic acid, WO-A-01/90052, WO-A-01/28978, particularly (1α,3α,5α)(3-amino-methyl-bicyclo [3.2.0]hept-3-yl)-acetic acid, EP0641330, WO-A-98/17627, WO-A-00/76958, particularly (3S,5R)-3-aminomethyl-5-methyl-octanoic acid, WO-A-03/082807, particularly (3S,5R)-3-amino-5-methyl-heptanoic acid, (3S,5R)-3-amino-5-methyl-nonanoic acid and (3S,5R)-3-amino-5-methyl-octanoic acid, WO-A-2004/039367, particularly (2S,4S)-4-(3-fluoro-phenoxymethyl)-pyrrolidine-2-carboxylic acid, (2S,4S)-4-(2,3-difluoro-benzyl)-pyrrolidine-2-carboxylic acid, (2S,4S)-4-(3-chlorophenoxy)proline and (2S,4S)-4-(3-fluorobenzyl)proline, EP1178034, EP1201240, WO-A-99/31074, WO-A-03/000642, WO-A-02/22568, WO-A-02/30871, WO-A-02/30881 WO-A-02/100392, WO-A-02/100347, WO-A-02/42414, WO-A-02/32736 and WO-A-02/28881, all of which are incorporated herein by reference.

Preferred alpha-2-delta ligands for use in the combination of the present invention include: gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)(3-amino-methyl-bicyclo [3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid, (3S,5R)-3-amino-5-methyl-octanoic acid, (2S,4S)-4-(3-chlorophenoxy)proline and (2S,4S)-4-(3-fluorobenzyl)proline or pharmaceutically acceptable salts thereof.

Further preferred alpha-2-delta ligands for use in the combination of the present invention are (3S,5R)-3-amino-5-methyloctanoic acid, (3S,5R)-3-amino-5-methylnonanoic acid, (3R,4R,5R)-3-amino-4,5-dimethylheptanoic acid and (3R,4R,5R)-3-amino-4,5-dimethyloctanoic acid, and the pharmaceutically acceptable salts thereof.

Particularly preferred alpha-2-delta ligands for use in the combination of the present invention are selected from gabapentin, pregabalin, (3S,5R)-3-amino-5-methyloctanoic acid, (1α,3α,5α)(3-amino-methyl-bicyclo[3.2.0]hept-3-yl)-acetic acid, (2S,4S)-4-(3-chlorophenoxy)proline and (2S,4S)-4-(3-fluorobenzyl)proline or pharmaceutically acceptable salts thereof.

The compounds of the present invention may be administered in combination with an oxytocin receptor antagonist. Thus, in a further aspect of the invention, there is provided a pharmaceutical product containing a progesterone receptor antagonist and one or more oxytocin antagonists, as a combined preparation for simultaneous, separate or sequential use in the treatment of endometriosis.

Examples of oxytocin receptor antagonists suitable for the present invention are atosiban (Ferring AB), barusiban (Ferring AB), TT-235 (Northwestern University), and AS-602305 (Serono SA).

The contents of the published patent applications mentioned above, and in particular the general formulae of the therapeutically active compounds of the claims and exemplified compounds therein, are incorporated herein in their entirety by reference thereto.

The compounds of the present invention may also be administered in combination with any one or more of the following
(i) Aromatase inhibitor;
(ii) Nuclear hormone receptor modulator;
(iii) Angiogenesis inhibitor;
(iv) VEGF inhibitor;
(v) Kinase inhibitor;
(vi) Protein farnesyl transferase inhibitor;
(vii) Prostanoid receptor antagonist;
(viii) Prostaglandin synthetase inhibitor;

(ix) Bioflavanoid;
(x) Alkylating agent;
(xi) Microtobule modulator, e.g. Microtobule stabilizer;
(xii) Topoisomerase I inhibitor;
(xiii) Protease inhibitor;
(xiv) Chemokine receptor antagonist; or
(xv) Neuroendocrine receptor modulators.

Thus, in a further aspect of the invention, there is provided a pharmaceutical product containing a progesterone receptor antagonist and any one or more of the following
(i) Aromatase inhibitor;
(ii) Nuclear hormone receptor modulator;
(iii) Angiogenesis inhibitor;
(iv) VEGF inhibitor;
(v) Kinase inhibitor;
(vi) Protein farnesyl transferase inhibitor;
(vii) Prostanoid receptor antagonist;
(viii) Prostaglandin synthetase inhibitor;
(ix) Bioflavanoid;
(x) Alkylating agent;
(xi) Microtobule modulator, e.g. Microtobule stabilizer;
(xii) Topoisomerase I inhibitor;
(xiii) Protease inhibitor;
(xiv) Chemokine receptor antagonist; or
(xv) Neuroendocrine receptor modulators.
as a combined preparation for simultaneous, separate or sequential use in the treatment of endometriosis.

Generally, compounds of the invention will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range <1 mg to 1000 mg depending, of course, on the mode of administration. For example, oral administration may require a total daily dose of from <1 mg to 1000 mg, while an intravenous dose may only require from <1 mg to 500 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with endometriosis and/or uterine leiomyoma. The treatment may be a pre-treatment as well as a treatment at the on-set of symptoms.

The compounds of formula (I) of the present invention have utility as EP2 antagonists in the treatment of various disease states. Preferably said EP2 antagonists exhibit a functional potency at the EP2 receptor expressed as an $IC_{50}$, lower than about 1000 nM, more preferably lower than 500 nM, yet more preferably lower than about 100 nM and more preferably still lower than about 50 nM wherein said $IC_{50}$ measurement of EP2 functional potency can be carried out using Protocol 1 below. Using this assay, compounds according to the present invention exhibit a functional potency at the EP2 receptor expressed as an $IC_{50}$ lower than 1000 nM.

Using this assay, compounds according to the present invention exhibit a functional potency at the EP2 receptor expressed as an $IC_{50}$ lower than 1000 nM.

Preferred compounds herein exhibit functional potency at the EP2 receptor as defined herein before and are selective for EP2 over DP1. Preferably said EP2 antagonists have a selectivity for EP2 over DP1 wherein said EP2 receptor antagonists are at least about 10-times, preferably at least about 20-times, more preferably at least about 30-times, even more preferably at least about 100-times, more preferably still at least about 300-times, even more preferably still at least about 500-times and especially at least about 1000-times more functionally selective for an EP2 receptor as compared with the DP1 receptor wherein said relative selectivity assessments are based on the measurement of DP1 and EP2 functional potencies which can be carried out using the assays described herein. DP1 activity is measured using Protocol 2 below.

Preferably said EP2 antagonists have a selectivity for EP2 over EP4 wherein said EP2 receptor antagonists are at least about 10-times, preferably at least about 30-times, more preferably at least about 100-times, more preferably still at least about 300-times, even more preferably still at least about 500-times and especially at least about 1000-times more functionally selective for an EP2 receptor as compared with the EP4 receptor wherein said relative selectivity assessments are based on the measurement of EP4 and EP2 functional potencies which can be carried out using the assays as described herein. EP4 activity is measured using Protocol 3 below.

Most preferred are EP2 antagonists have a selectivity for EP2 over DP1 and EP4 wherein said EP2 receptors antagonists are at least about 10-times, preferably at least about 30-times, more preferably at least about 100-times, more preferably still at least about 300-times, even more preferably still at least about 1000-times more functionally selective for an EP2 receptor as compared with the DP1 and EP4 receptors.

The compounds of the present invention may be tested in the screens set out below.

1.0 Measurement of In Vitro Antagonist Potency ($IC_{50}$) of Compounds Against Recombinant Human Prostaglandin E2 Receptor in CHO Cells The prostaglandin E2 (EP-2) receptor is Gs coupled and agonism of the receptor by PGE2 results in activation of intracellular adenylate cyclase enzymes that synthesise the second messenger signalling molecule, adenosine 3',5'-cyclic monophosphate (cAMP). CHO cells expressing the recombinant human EP-2 receptor are stimulated with PGE2 (5 nM) equivalent to approximately EC50 values to give the maximal cAMP signal. Decreases in cAMP levels following treatment of stimulated recombinant EP-2 cells with potential antagonist compounds were measured and potency ($IC_{50}$) calculated as follows.

A Chinese hamster ovary (CHO) cell line stably transfected with full length cDNA encoding human Prostaglandin E2 was established using standard molecular biology methods. Test compounds were dissolved in dimethyl sulphoxide (DMSO) at 4 mM. 11 point half log unit increment dilution series of test compound were prepared in DMSO then diluted 1 in 40 in a buffer comprised of phosphate buffered saline (PBS) and 0.05% pluronic F-127 surfactant. Freshly cultured cells at 80-90% confluence were harvested and re-suspended in 90% growth media/10% DMSO. The cells were frozen using a planar freezer and stored in frozen aliquots in cryovials in liquid nitrogen until the day of the experiment. A vial of cells was defrosted in a 37° C. water bath for 2 min, then transferred to 10 ml of Dulbecco's Modified Eagle's Medium (DMEM). The cells were then centrifuged for 5 min at 1000 g and the pellet re-suspended at 1,000,000 cells/ml in DMEM. 5,000 cells (5 ul) were added to 5 ul of the compound dilution series in a 384 well assay plate and pre-incubated for 30 min at 37° C. 5 ul of agonist (15 nM PGE2 in PBS to give 5 nM FAC) was added and plates further incubated for 90 min at 37° C. The relative cAMP concentration in each well was then measured using a β-galactosidase enzyme fragment complementation method purchased in kit form as the Discoverx cAMP II kit from GE Healthcare, UK. The luminescence readings taken from each assay well were converted into percent effect relative to maximum control wells corresponding to a 30 uM of 6-chloro-2-(4-pentyloxy-benzoyl)-1H-indol-3-yl]-acetic acid (prepared according to methods outlined in WO 9935130) demonstrated to give a maximal effect. Sigmoidal curves were fitted to plots of $\log_{10}$ inhibitor concentration vs percent effect. $IC_{50}$ estimates were determined as the concentration of test compound giving an effect half way between the bottom and top asymptotes of the sigmoidal dose response curve. Each experiment included an $IC_{50}$ determination for the literature compound as a standard to track assay consistency and allow fair comparison between values obtained in different experiments. The EC50 of PGE2 is used in combination with the ligand concentration in the assay to determine Ki values for antagonist dose responses using the Cheng-Prusoff equation. Consequently an agonist dose response curve is carried out for each experiment using the same incubation as the antagonist plate.

2.0 Measurement of In Vitro Antagonist Potency ($IC_{50}$) of Compounds Against Recombinant Human Prostaglandin D1 Receptor in CHO Cells The prostaglandin D1 (DP-1) receptor is Gs coupled and agonism of the receptor by PGE2 results in activation of intracellular adenylate cyclase enzymes that synthesise the second messenger signalling molecule, adenosine 3',5'-cyclic monophosphate (cAMP). CHO cells expressing the recombinant human DP-1 receptor are stimulated with BW245C (10 nM) equivalent to approximately EC70 values to give the maximal cAMP signal. Decreases in cAMP levels following treatment of stimulated recombinant DP-1 cells with potential antagonist compounds were measured and potency ($IC_{50}$) calculated as follows.

A Chinese hamster ovary (CHO) cell line stably transfected with full length cDNA encoding human Prostaglandin D1 was established using standard molecular biology methods. Test compounds were dissolved in dimethyl sulphoxide (DMSO) at 4 mM. 11 point half log unit increment dilution series of test compound were prepared in DMSO then diluted 1 in 40 in a buffer comprised of phosphate buffered saline (PBS) and 0.05% pluronic F-127 surfactant. Freshly cultured cells at 80-90% confluence were harvested and re-suspended in 90% growth media/10% DMSO. The cells were frozen using a planar freezer and stored in frozen aliquots in cryovials in liquid nitrogen until the day of the experiment. A vial of cells was defrosted in a 37° C. water bath for 2 min, then transferred to 10 ml of Dulbecco's Modified Eagle's Medium (DMEM). The cells were then centrifuged for 5 min at 1000 g and the pellet re-suspended at 1,000,000 cells/ml in DMEM. 5,000 cells (5 ul) were added to 5 ul of the compound dilution series in a 384 well assay plate and pre-incubated for 30 min at 37° C. 5 ul of agonist (30 nM BW245C in PBS to give 10 nM FAC) was added and plates further incubated for 90 min at 37° C. The relative cAMP concentration in each well was then measured using a β-galactosidase enzyme fragment complementation method purchased in kit form as the Discoverx cAMP II kit from GE Healthcare, UK. The luminescence readings taken from each assay well were converted into percent effect relative to maximum control wells corresponding to a 30 uM of S-5751, demonstrated to give a maximal effect. Sigmoidal curves were fitted to plots of $\log_{10}$ inhibitor concentration vs percent effect. $IC_{50}$ estimates were determined as the concentration of test compound giving an effect half way between the bottom and top asymptotes of the sigmoidal dose response curve. Each experiment included an $IC_{50}$ determination for the literature compound as a standard to track assay consistency and allow fair comparison between values obtained in different experiments. The EC70 of BW245C is used in combination with the ligand concentration in the assay to determine Ki values for antagonist dose responses using the Cheng-Prusoff equation. Consequently an agonist dose response curve is carried out for each experiment using the same incubation as the antagonist plate.

3.0 Measurement of In Vitro Antagonist Potency ($IC_{50}$) of Compounds Against Recombinant Human Prostaglandin E4 Receptor in CHO Cells The prostaglandin E4 (EP-4) receptor is Gs coupled and agonism of the receptor by PGE2 results in activation of intracellular adenylate cyclase enzymes that synthesise the second messenger signalling molecule, adenosine 3',5'-cyclic monophosphate (cAMP). CHO cells expressing the recombinant human EP-4 receptor are stimulated with PGE2 (6 nM) equivalent to approximately EC50 values to give the maximal cAMP signal. Decreases in cAMP levels following treatment of stimulated recombinant EP-2 cells with potential antagonist compounds were measured and potency ($IC_{50}$) calculated as follows.

A Chinese hamster ovary (CHO) cell line stably transfected with full length cDNA encoding human Prostaglandin E4 was established using standard molecular biology methods. Test compounds were dissolved in dimethyl sulphoxide (DMSO) at 4 mM. 11 point half log unit increment dilution series of test compound were prepared in DMSO then diluted 1 in 40 in a buffer comprised of phosphate buffered saline (PBS) and 0.05% pluronic F-127 surfactant. Freshly cultured cells at 80-90% confluence were harvested and re-suspended in 90% growth media/10% DMSO. The cells were frozen using a planar freezer and stored in frozen aliquots in cryovials in liquid nitrogen until the day of the experiment. A vial of cells was defrosted in a 37° C. water bath for 2 min, then transferred to 10 ml of Dulbecco's Modified Eagle's Medium (DMEM). The cells were then centrifuged for 5 min at 1000 g and the pellet re-suspended at 1,000,000 cells/ml in DMEM. 5,000 cells (5 ul) were added to 5 ul of the compound dilution series in a 384 well assay plate and pre-incubated for 30 min at 37° C. 5 ul of agonist (6 nM PGE2 in PBS to give 2 nM FAC) was added and plates further incubated for 90 min at 37° C. The relative cAMP concentration in each well was then measured using a β-galactosidase enzyme fragment complementation method purchased in kit form as the Discoverx cAMP II kit from GE Healthcare, UK. The luminescence readings taken from each assay well were converted into percent effect relative to maximum control wells corresponding to a 30 uM of 4-{(S)-1-[5-Chloro-2-(4-chloro-benzyloxy)-benzoylamino]-ethyl}-benzoic acid (WO2005105733), demonstrated to give a maximal effect. Sigmoidal curves were fitted to plots of $\log_{10}$ inhibitor concentration vs percent effect. $IC_{50}$ estimates were determined as the concentration of test compound giving an effect half way between the bottom and top asymptotes of the sigmoidal dose response curve. Each experiment included an $IC_{50}$ determination for the literature compound as a standard to track assay consistency and allow fair comparison between values obtained in different experiments. The EC50 of PGE2 is used in combination with the ligand concentration in the assay to determine Ki values for antagonist dose responses using the Cheng-Prusoff equation. Consequently an agonist dose response curve is carried out for each experiment using the same incubation as the antagonist plate.

| In-vitro Biological Data | |
|---|---|
| Example no. | EP2 Ki (nM) |
| 1 | 0.633 |
| 2 | 0.344 |
| 3 | 24.4 |
| 4 | 82.1 |
| 5 | 1.64 |
| 6 | 102 |
| 7 | 2.97 |
| 8 | 10.9 |
| 9 | 520 |
| 10 | 0.741 |
| 11 | 28.9 |
| 12 | 4.82 |
| 13 | 333 |
| 14 | 522 |
| 15 | 84.7 |
| 16 | 0.692 |
| 17 | 2.01 |
| 18 | 17.2 |
| 19 | 2.35 |
| 20 | 89 |
| 21 | 4.09 |
| 22 | 142 |
| 23 | 94.6 |
| 24 | 42.7 |
| 25 | 192 |
| 26 | 0.0376 |
| 27 | 4.34 |
| 28 | 0.334 |
| 29 | 28.2 |
| 30 | 0.461 |
| 31 | 282 |
| 32 | 0.735 |
| 33 | 141 |
| 34 | 0.743 |
| 35 | 105 |
| 36 | 1.16 |
| 37 | 30.3 |
| 38 | 3.08 |
| 39 | 48.1 |
| 40 | 2.36 |
| 41 | 66.9 |
| 42 | 2.93 |
| 43 | 145 |
| 44 | 3.83 |
| 45 | 170 |
| 46 | 23.7 |
| 47 | 226 |
| 48 | 43.8 |
| 49 | 124 |
| 50 | 1.88 |
| 51 | 19.3 |
| 52 | 134 |
| 53 | 17.5 |
| 54 | 389 |
| 55 | 28.9 |
| 56 | 466 |
| 57 | 29.4 |
| 58 | 884 |
| 59 | 98.1 |
| 60 | 979 |
| 61 | 26.2 |
| 62 | 868 |
| 63 | 174 |
| 64 | 621 |
| 65 | 175 |
| 66 | 3.3 |
| 67 | 85.7 |
| 68 | 14.6 |
| 69 | 309 |
| 70 | 22.7 |
| 71 | 23.9 |
| 72 | 25.5 |
| 73 | 459 |
| 74 | 35.6 |
| 75 | 504 |
| 76 | 158 |
| 77 | 213 |
| 78 | 511 |
| 79 | 21.3 |
| 80 | 344 |
| 81 | 55.5 |
| 82 | 524 |
| 83 | 119 |
| 84 | 438 |
| 85 | 7.29 |
| 86 | 5.36 |
| 87 | 225 |
| 88 | 14.9 |
| 89 | 252 |
| 90 | 4.16 |
| 91 | 37.4 |
| 92 | 7.81 |
| 93 | 165 |
| 94 | 431 |
| 95 | 1.03 |
| 96 | 178 |
| 97 | 1.89 |
| 98 | 260 |
| 99 | 1.99 |
| 100 | 518 |
| 101 | 3.59 |
| 102 | 160 |
| 103 | 3.77 |
| 104 | 392 |

The invention includes all polymorphs of the compounds of Formula (I) and crystal habits thereof.

The compounds of the invention may have the advantage that they are more potent, have a longer duration of action, have a broader range of activity, are more stable, have fewer side effects or are more selective, or have other more useful properties than the compounds of the prior art.

Thus the invention provides:
(i) a compound of formula (I) or a pharmaceutically acceptable derivative thereof;
(ii) a process for the preparation of a compound of formula (I) or a pharmaceutically acceptable derivative thereof;
(iii) a pharmaceutical formulation including a compound of formula (I) or a pharmaceutically acceptable derivative thereof, together with a pharmaceutically acceptable excipients, diluent or carrier;
(iv) a compound of formula (I) or a pharmaceutically acceptable derivative or composition thereof, for use as a medicament;
(v) the use of a compound of formula (I) or of a pharmaceutically acceptable derivative or composition thereof, for the manufacture of a medicament for the treatment of endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome;
(vi) use as in (v) where the disease or disorder is endometriosis and/or uterine fibroids (leiomyomata);
(vii) a method of treatment of a mammal to treat endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome including treating said mammal with an effective amount of a compound of formula (I) or with a pharmaceutically acceptable derivative or composition thereof;
(viii) a method as in (vii) where the disease or disorder is endometriosis and/or uterine fibroids (leiomyomata);

(ix) novel intermediates as described herein;
(x) a combination as described herein.

Other aspects of the invention will be apparent from the claims.

The Preparations and Examples that follow illustrate the invention but do not limit the invention in any way. All starting materials are available commercially or described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance traveled by a compound divided by the distance traveled by the solvent front on a TLC plate. Melting points were determined using a Gallenkamp MPD350 apparatus and are uncorrected. NMR was carried out using a Varian-Unity (nova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

The invention is illustrated by the following non-limiting Examples in which the following abbreviations and definitions are used:
APCI atmospheric pressure chemical ionisation mass spectrum
br broad
δ chemical shift
d doublet
DMF N,N-Dimethylformamide
ES electrospray ionisation
HPLC high pressure liquid chromatography
LRMS low resolution mass spectrum
m multiplet
Me methyl
m/z mass spectrum peak
NMR nuclear magnetic resonance
g gram
mg milligram
Rt retention time
s singlet
SM starting material
soln. solution
t triplet
(±) racemic mixture For the avoidance of doubt, named compounds used herein have been named using ACD Labs Name Software v7.11™.

Where singleton compounds have been analysed by LCMS, there are six methods used. These are illustrated below.
System 1—6 Minute Basic Run:
A: 0.1% ammonium hydroxide in water
B: 0.1% ammonium hydroxide in acetonitrile
Column: C18 phase Fortis 50×4.6 mm with 5 micron particle size
Gradient: 95-5% A over 3 min, 1 min hold, 1 mL/min
UV: 210 nm-450 nm DAD
Temperature: 50° C.
System 2—2 Minute Acidic Run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 min hold, 1.8 mL/min
UV: 210 nm-450 nm DAD
Temperature: 75° C.
System 3—Mass Spec:
ESCi: MS
Solvent 20 mM Ammonia 1 minute run
System 4—6 Minute Acidic Run:
A: 0.1% formic acid in water
B: 0.1% formic acid in acetonitrile
Column: C18 phase Phenomenex Luna 50×4.6 mm with 5 micron particle size
Gradient: 95-5% A over 3 min, 1 min hold, 1 mL/min
UV: 210 nm-450 nm DAD
Temperature: 50° C.
System 5—5 minute acidic run:
A 0.0375% TFA in water
B 0.01875% TFA in acetonitrile
Column Ymc ODS-AQ 50 mm×2 mm with 5 micron particle size
Gradient: 90-10% A over 4.7 min, 1 min hold, 0.8 mL/min
Temperature: 50° C.
System 6—5 minute acidic run:
A 0.0375% TFA in water
B 0.01875% TFA in acetonitrile
Column Ymc ODS-AQ 50 mm×2 mm with 5 micron particle size
Gradient: 99-0% A over 4.7 min, 1 min hold, 0.8 mL/min
Temperature: 50° C.
Mass Spectrometer Model: Agilent 1956A
Ionization Mode: API-ES
Polarity: Positive Where singleton compounds have been purified by High Performance Liquid Chromatography, unless otherwise stated, one of two methods were used, and these are shown below.

|  | Method a | Method b |
| --- | --- | --- |
| Column | Sunfire C18 4.6 × 50 mm id | Xterra 4.6 × 50 mm id |
| Temperature | Ambient | Ambient |
| Mobile Phase A | 0.05% formic acid in water | 0.05% ammonia in water |
| Mobile Phase B | 0.05% formic acid in acetonitrile | 0.05% ammonia in acetonitrile |
| Gradient-Initial | 5% B | 5% B |
| Time 0 mins | 5% B | 5% B |
| Time 3 mins | 98% B | 98% B |
| Time 4 mins | 98% B | 98% B |
| Time 4.1 mins | 5% B | 5% B |
| Time 5 mins | 5% B | 5% B |
| Flow rate | 1.5 mL/min | 1.5 mL/min |
| Injection volume | 5 μL | 5 μL |

EXAMPLE 1

3-(4'-Cyano-biphenyl-4-yloxymethyl)-1-(4-methoxybenzoyl)-pyrrolidine-3-carboxylic acid
(enantiomer 1)

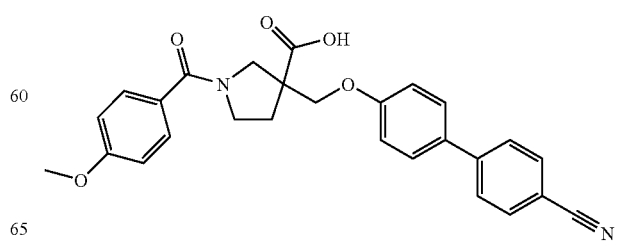

Sodium trimethyl silanolate (72.1 g) and water (7.72 mL, 428.6 mmol) were added to a stirred solution of 3-(4'-cyano-biphenyl-4-yloxymethyl)-1-(4-methoxy-benzoyl)-pyrrolidine-3-carboxylic acid ethyl ester (see Preparation 28) (207.7 g, 428.6 mmol) in acetonitrile (2090 mL). The resulting mixture was stirred at RT for 18 hours. The reaction mixture was filtered and the solid was partitioned between ethyl acetate (2000 mL) and aqueous hydrogen chloride solution (2000 mL, 2M). The organic layer was washed with water (1000 mL) then concentrated under reduced pressure to afford a pale orange foam. This was recrystallised twice, from ethyl acetate (700 mL) then isopropyl alcohol (700 mL) to afford the title compound as a white solid (107.2 g, 55%).

1H NMR (400 MHz, DMSO d-6) δ ppm 1.89-2.05 (m, 1H), 2.15-2.19 (m, 1H), 3.40-3.53 (m, 3H), 3.66 (s, 3H), 3.82 (d, 1H), 3.96-4.23 (m, 2H), 6.84 (d, 2H), 6.90 (d, 1H), 6.96 (d, 1H), 7.36-7.42 (m, 2H), 7.54-7.58 (m, 2H), 7.70-7.75 (m, 4H)

LCMS Rt 7.14 mins, ES m/z 457 [MH]+

Hydrolysis Method A

EXAMPLE 2

3-(4'-Cyano-biphenyl-4-yloxymethyl)-1-(4-fluoro-benzoyl)-pyrrolidine-3-carboxylic acid (enantiomer 1)

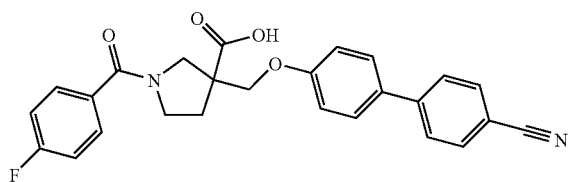

Lithium hydroxide (16 mg, 0.67 mmol) was added to a stirred solution of 3-(4'-cyano-biphenyl-4-yloxymethyl)-1-(4-fluoro-benzoyl)-pyrrolidine-3-carboxylic acid ethyl ester (see Preparation 29) (105 mg, 0.22 mmol) in ethanol (1 mL) and water (1 mL). The resulting mixture was stirred at RT for 5 hours. The mixture was concentrated under reduced pressure to remove ethanol and the residue was partitioned between ethyl acetate (5 mL) and 2M HCl aqueous solution (5 mL). The organic layer was washed with brine (5 mL), dried over magnesium sulphate and concentrated under reduced pressure to afford a white solid. This was recrystallised from isopropyl alcohol (2.5 mL) to afford the title compound as a white solid (76 mg, 77%).

LCMS Rt 3.06 mins, ES m/z 445 [MH]+

Hydrolysis Method B

EXAMPLE 3

3 ((4-(5-cyanopyridin-2-yl)phenoxy)methyl)-1-(2-methoxybenzoyl)pyrrolidine-3-carboxylic acid

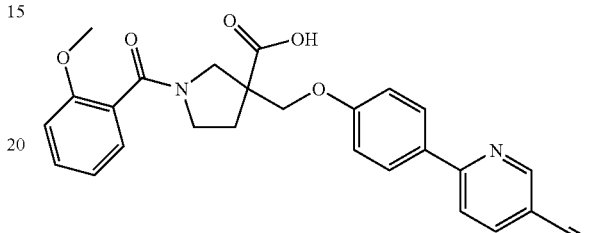

Potassium trimethyl silanolate (14 mg, 0.10 mmol) was added to a stirred solution of 3-[4-(5-cyano-pyridin-2-yl)-phenoxymethyl]-1-(2-methoxy-benzoyl)-pyrrolidine-3-carboxylic acid ethyl ester (see Preparation 43) (40 mg, 0.08 mmol) in tetrahydrofuran (5 mL). The resulting mixture was stirred at RT for 18 hours. The reaction mixture was concentrated under reduced pressure and the residue was partitioned between ethyl acetate (5 mL) and 2M HCl aqueous solution (5 mL). The organic layer was washed with brine (5 mL) then concentrated under reduced pressure to afford a colourless gum. The residue was purified by column chromatography on silica gel, eluting with ethyl acetate then methanolic ammonia to afford the title compound as a white solid (18 mg, 48%).

LCMS Rt 2.79 mins, ES m/z 458 [MH]+

Hydrolysis Method C

Examples 4 to 85 were prepared according to one of the methods described above for Examples 1-3, starting from the appropriate halo or tosylate compounds of formula (II) and the appropriate alcohols of formula (III) (where X=bond).

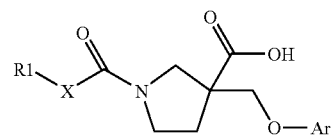

| Ex | R¹ | Ar | Method | Data |
|---|---|---|---|---|
| 4 | F-⟨⟩- | ⟨⟩-⟨⟩-CN | B | Enantiomer 2<br>LCMS Rt 1.51 mins<br>ES m/z 445 [MH]+ |

-continued

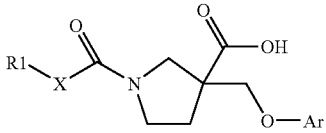

| Ex | R¹ | Ar | Method | Data |
|---|---|---|---|---|
| 5 | 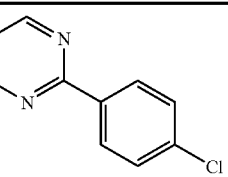 | 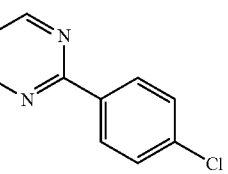 | B | Enantiomer 1<br>LCMS Rt 3.12 mins<br>ES m/z 456 [MH]⁺ |
| 6 | 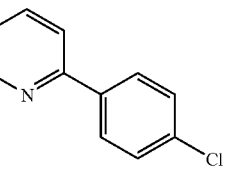 | 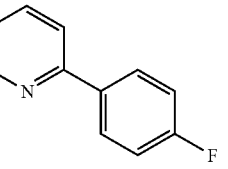 | B | Enantiomer 2<br>LCMS Rt 3.08 mins<br>ES m/z 456 [MH]⁺ |
| 7 | 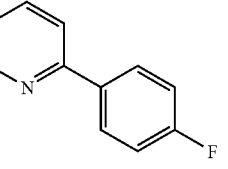 | 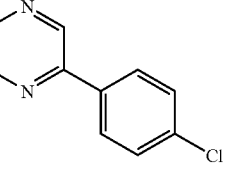 | B | Enantiomer 1<br>LCMS Rt 3.06 mins,<br>ES m/z 455 [MH]⁺ |
| 8[a] | 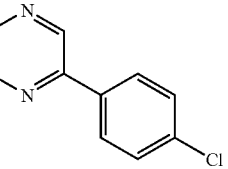 | 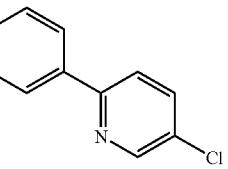 | B | Enantiomer 1<br>LCMS Rt 2.86 mins,<br>ES m/z 439 [MH]⁺ |
| 9[b] | | | B | Enantiomer 2<br>LCMS Rt 2.87 mins,<br>ES m/z 439 [MH]⁺ |
| 10 | | | B | Enantiomer 1<br>LCMS Rt 3.15 mins,<br>ES m/z 456 [MH]⁺ |
| 11 | | | B | Enantiomer 2<br>LCMS Rt 3.16 mins,<br>ES m/z 456 [MH]⁺ |
| 12 | | | B | Enantiomer 1<br>LCMS Rt 3.09 mins,<br>ES m/z 455 [MH]⁺ |

-continued

| Ex | R¹ | Ar | Method | Data |
|---|---|---|---|---|
| 13 | 4-F-C₆H₄- | 4-(5-chloropyridin-2-yl)phenyl | B | Enantiomer 2<br>LCMS Rt 3.09 mins<br>ES m/z 455 [MH]⁺ |
| 14 | 4-F-C₆H₄- | 2,3-difluorophenyl | B^c | Enantiomer 1<br>LCMS Rt 2.07 mins<br>ES m/z 380 [MH]⁺ |
| 15 | 4-F-C₆H₄- | 4-(5-chloropyrimidin-2-yl)phenyl | B | Enantiomer 1<br>LCMS Rt 2.63 mins<br>ES m/z 456 [MH]⁺ |
| 16 | 4-F-C₆H₄- | 4-(5-chloropyrimidin-2-yl)phenyl | B | Enantiomer 2<br>LCMS Rt 2.65 mins<br>ES m/z 456 [MH]⁺ |
| 17 | 4-F-C₆H₄- | 4'-fluoro-[1,1'-biphenyl]-4-yl | B^d | Enantiomer 1<br>1H NMR (400 MHz, CHLOROFORM-d) δ ppm 2.07 (br. s. 1 H) 2.47 (br. s. 1 H) 3.08-3.20 (m, 2 H) 3.40-3.85 (m, 3 H) 3.94-4.22 (br m. 1 H) 7.12 (m, 5 H) 7.50 (br s. 1 H) 7.49-7.53 (br. m. 6 H) |
| 18 | 4-F-C₆H₄- | 4'-fluoro-[1,1'-biphenyl]-4-yl | B^e | Enantiomer 2<br>1H NMR (400 MHz, CHLOROFORM-d) δ ppm 2.45 (br. s. 2H) 3.65-3.80 (br. d. 3 H) 4.05 (br. s. 1 H) 4.25 (br. m. 2 H) 6.88 (br. m. 2 H) 7.05 (m. 4. H) 7.38-7.45 (m, 4 H) 7.51 (m, 2 H) |
| 19^a | 4-F-C₆H₄- | 4-(5-cyanopyridin-2-yl)phenyl | B | Enantiomer 1<br>LCMS Rt 3.17 mins,<br>ES m/z 446 [MH]⁺ |

Structure (header): R1–X–C(=O)–N(pyrrolidine with 3-carboxylic acid and 3-CH₂–O–Ar substituents)

-continued

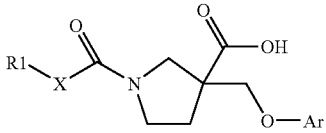

| Ex | R¹ | Ar | Method | Data |
|---|---|---|---|---|
| 20[b] | 4-F-phenyl | 6-(4-phenyl)-pyridine-3-carbonitrile | B | Enantiomer 2<br>LCMS Rt 3.16 mins,<br>ES m/z 446 [MH]⁺ |
| 21[a] | 4-F-phenyl | 2-(4-phenyl)-5-fluoropyrimidine | B | Enantiomer 1<br>LCMS Rt 3.28 mins,<br>ES m/z 440 [MH]⁺ |
| 22[b] | 4-F-phenyl | 2-(4-phenyl)-5-fluoropyrimidine | B | Enantiomer 2<br>LCMS Rt 3.21 mins,<br>ES m/z 440 [MH]⁺ |
| 23[a] | 4-F-phenyl | 5-(4-cyanophenyl)-pyridine | B | Enantiomer 1<br>LCMS Rt 3.12 mins,<br>ES m/z 446 [MH]⁺ |
| 24[a] | 4-F-phenyl | 2-(4-fluorophenyl)-pyrazine | B | Enantiomer 1<br>LCMS Rt 3.11 mins,<br>ES m/z 440 [MH]⁺ |
| 25 | 4-F-phenyl | 3-chloro-4-fluorophenyl | B[f] | Enantiomer 1<br>ES m/z 396 [MH]⁺ |
| 26 | 4-Cl-phenyl | 4'-cyanobiphenyl | B | Enantiomer 1<br>LCMS Rt 3.12 mins,<br>ES m/z 461 [MH]⁺ |
| 27 | 4-Cl-phenyl | 4'-cyanobiphenyl | B | Enantiomer 2<br>LCMS Rt 2.84 mins,<br>ES m/z 461 [MH]⁺ |

-continued

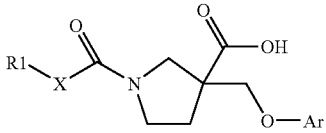

| Ex | R¹ | Ar | Method | Data |
|---|---|---|---|---|
| 28 | 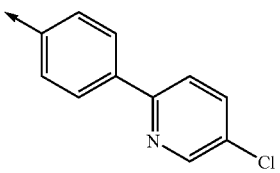 | 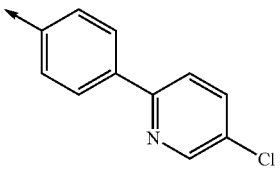 | B | Enantiomer 1<br>LCMS Rt 3.21 mins,<br>APCI m/z 472 [MH]⁺ |
| 29 | 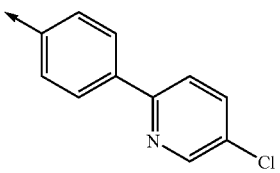 | 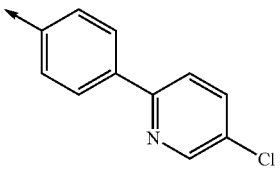 | B | Enantiomer 2<br>LCMS Rt 3.21 mins,<br>APCI m/z 472 [MH]⁺ |
| 30 | 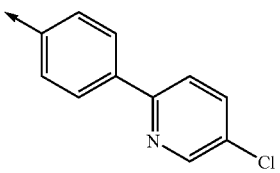 | 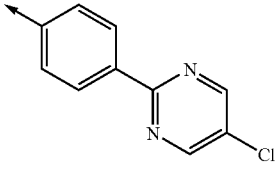 | B | Enantiomer 1<br>LCMS Rt 3.12 mins<br>ES m/z 472 [MH]⁺ |
| 31 | 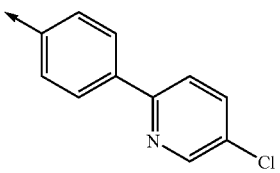 | 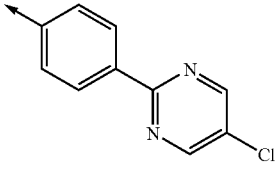 | B | Enantiomer 2<br>LCMS Rt 3.17 mins<br>ES m/z 472 [MH]⁺ |
| 32 | 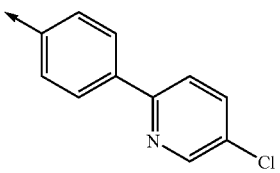 | 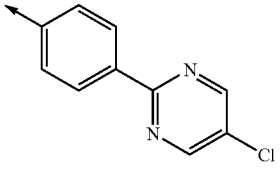 | B | Enantiomer 1<br>LCMS Rt 3.01 mins,<br>APCI m/z 471 [MH]⁺ |
| 33 | 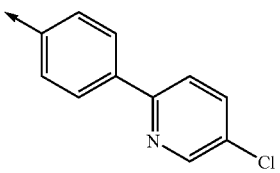 | 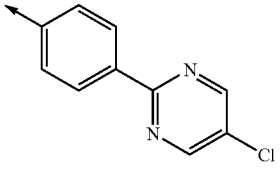 | B | Enantiomer 2<br>LCMS Rt 3.09 mins<br>ES m/z 471 [MH]⁺ |
| 34 | 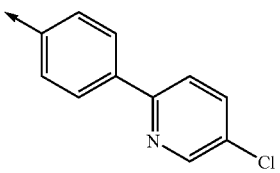 | 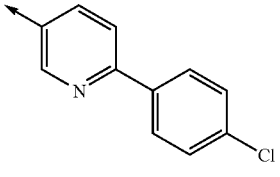 | B | Enantiomer 1<br>LCMS Rt 3.30 mins,<br>ES m/z 472 [MH]⁺ |
| 35 | 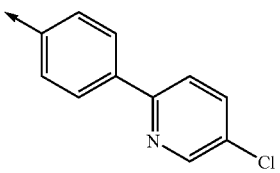 | 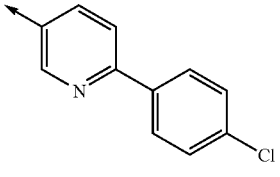 | B | Enantiomer 2<br>LCMS Rt 3.30 mins<br>ES m/z 472 [MH]⁺ |

-continued

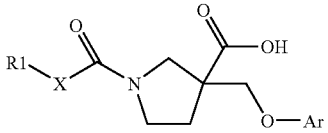

| Ex | R¹ | Ar | Method | Data |
|---|---|---|---|---|
| 36 | 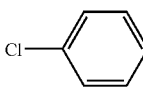 | 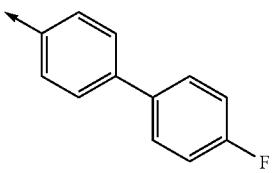 | B | Enantiomer 1<br>LCMS Rt 3.31 mins,<br>ES m/z 454 [MH]⁺ |
| 37 | 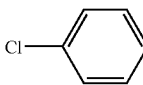 | 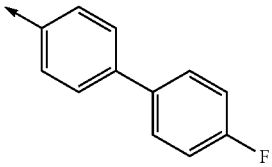 | B | Enantiomer 2<br>LCMS Rt 3.30 mins,<br>ES m/z 454 [MH]⁺ |
| 38 | 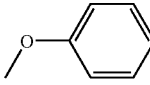 | 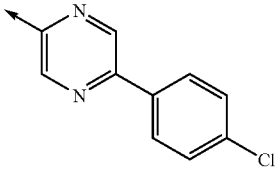 | B | Enantiomer 1<br>LCMS Rt 3.11 mins,<br>ES m/z 468 [MH]⁺ |
| 39 | 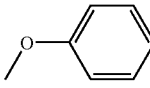 | 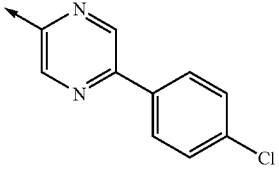 | B | Enantiomer 2<br>LCMS Rt 3.11 mins,<br>ES m/z 468 [MH]⁺ |
| 40 | 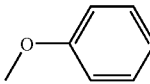 | 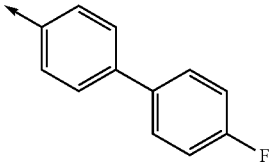 | B | Enantiomer 1<br>LCMS Rt 1.49 mins,<br>ES m/z 450 [MH]⁺ |
| 41 | 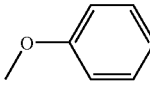 | 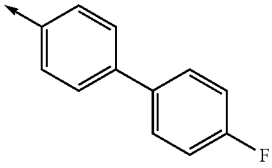 | B | Enantiomer 2<br>LCMS Rt 1.49 mins,<br>ES m/z 450 [MH]⁺ |
| 42 | 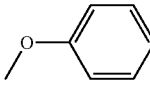 | 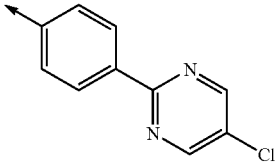 | B | Enantiomer 1<br>LCMS Rt 2.97 mins,<br>ES m/z 468 [MH]⁺ |
| 43 | 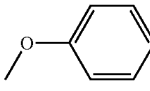 |  | B | Enantiomer 2<br>LCMS Rt 3.00 mins,<br>ES m/z 468 [MH]⁺ |

-continued

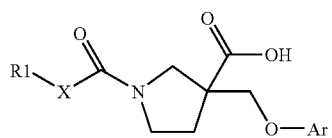

| Ex | R¹ | Ar | Method | Data |
|---|---|---|---|---|
| 44 | 4-methoxyphenyl | 5-(4-chlorophenyl)pyridin-2-yl | B | Enantiomer 1<br>LCMS Rt 3.00 mins,<br>ES m/z 467 [MH]$^+$ |
| 45 | 4-methoxyphenyl | 5-(4-chlorophenyl)pyridin-2-yl | B | Enantiomer 2<br>LCMS Rt 1.46 mins,<br>ES m/z 467 [MH]$^+$ |
| 46 | 4-methoxyphenyl | 5-chloro-2-phenylpyridin-... | B | Enantiomer 1<br>LCMS Rt 1.46 mins,<br>ES m/z 467 [MH]$^+$ |
| 47 | 4-methoxyphenyl | 5-chloro-2-phenylpyridin-... | B | Enantiomer 2<br>LCMS Rt 1.47 mins,<br>ES m/z 467 [MH]$^+$ |
| 48 | 4-methoxyphenyl | 4'-cyanobiphenyl-4-yl | B | Enantiomer 2<br>LCMS Rt 3.03 mins,<br>ES m/z 457 [MH]$^+$ |
| 49 | 4-methoxyphenyl | 2-(4-chlorophenyl)pyrimidin-5-yl | B | Enantiomer 1<br>LCMS Rt 3.08 mins,<br>ES m/z 468 [MH]$^+$ |
| 50 | 4-methoxyphenyl | 2-(4-chlorophenyl)pyrimidin-5-yl | B | Enantiomer 2<br>LCMS Rt 3.18 mins,<br>ES m/z 468 [MH]$^+$ |

-continued

| Ex | R¹ | Ar | Method | Data |
|---|---|---|---|---|
| 51 | 2-ethoxyphenyl | 5-(4-chlorophenyl)pyrazin-2-yl | B | Enantiomer 1<br>LCMS Rt 3.26 mins,<br>ES m/z 482 [MH]⁺ |
| 52 | 2-ethoxyphenyl | 5-(4-chlorophenyl)pyrazin-2-yl | B | Enantiomer 2<br>LCMS Rt 3.26 mins<br>ES m/z 482 [MH]⁺ |
| 53 | 2-ethoxyphenyl | 4'-fluorobiphenyl-4-yl | B | Enantiomer 1<br>1H NMR (400 MHz, METHANOL-d₄) δ ppm 2.12-2.25 (m, 1H) 2.35-2.50 (m, 1H) 3.40-3.50 (m, 2H) 3.68-4.34 (m, 9H) 6.94-7.04 (m, 3H) 7.12-7.25 (m, 3H) 7.39-7.58 (m, 6H). ES m/z 464 [MH]⁺ |
| 54 | 2-ethoxyphenyl | 4'-fluorobiphenyl-4-yl | B | Enantiomer 2<br>1H NMR (400 MHz, METHANOL-d₄) δ ppm 2.10-2.24 (m, 1H) 2.35-2.47 (m, 1H) 3.40-3.50 (m, 2H) 3.65-4.34 (m, 9H) 6.94-7.04 (m, 3H) 7.12-7.29 (m, 3H) 7.340-7.58 (m, 6H). ES m/z 464 [MH]⁺ |
| 55 | 2-ethoxyphenyl | 4-(5-chloropyrimidin-2-yl)phenyl | B | Enantiomer 1<br>1H NMR (400 MHz, METHANOL-d₄) δ ppm 2.15-2.30 (m, 1H) 2.37-2.50 (m, 1H) 3.40-3.51 (m, 1H), 3.71-3.85 (m, 3H) 4.08-4.13 (m, 3H) 4.26-4.38 (m, 1H) 6.96-7.06 (m, 2H) 7.20-7.26 (m, 1H) 7.37-7.41 (m, 1H) 8.29-8.25 (m, 2H) 8.75 (d, 2H)<br>ES m/z 482 [MH]⁺ |
| 56 | 2-ethoxyphenyl | 4-(5-chloropyrimidin-2-yl)phenyl | B | Enantiomer 2<br>ES m/z 482 [MH]⁺ |

-continued
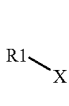
| Ex | R¹ | Ar | Method | Data |
|---|---|---|---|---|
| 57 | 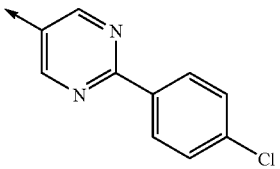 | 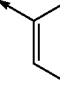 | B | Enantiomer 1<br>LCMS Rt 3.16 mins,<br>ES m/z 482 [MH]⁺ |
| 58 | 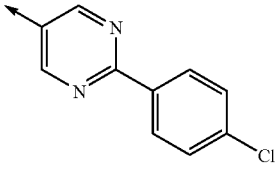 | 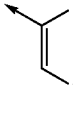 | B | Enantiomer 2<br>LCMS Rt 3.16 mins,<br>ES m/z 482 [MH]⁺ |
| 59 | 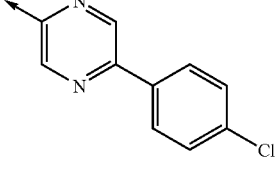 | 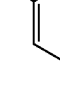 | B | Enantiomer 1<br>LCMS Rt 3.09 mins<br>ES m/z 468 [MH]⁺ |
| 60 | 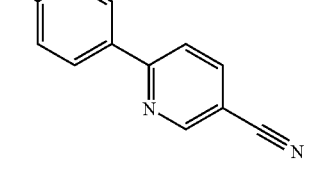 | 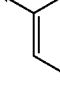 | C | Enantiomer 2<br>LCMS Rt 2.79 mins,<br>ES m/z 458 [MH]⁺ |
| 61 | 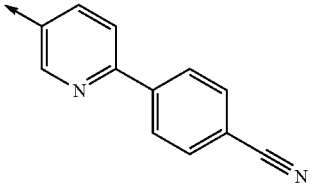 | 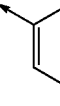 | C | Enantiomer 1<br>LCMS Rt 2.73 mins,<br>ES m/z 458 [MH]⁺ |
| 62 | 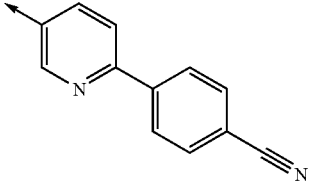 | 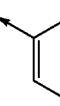 | C | Enantiomer 2<br>LCMS Rt 2.73 mins,<br>ES m/z 458 [MH]⁺ |
| 63 | 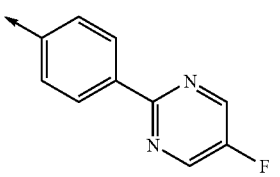 | | B | Enantiomer 1<br>LCMS Rt 2.35 mins,<br>ES m/z 452 [MH]⁺ |

-continued
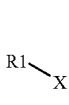
| Ex | R¹ | Ar | Method | Data |
|---|---|---|---|---|
| 64 | 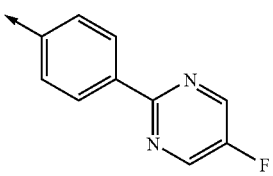 |  | B | Enantiomer 2<br>LCMS Rt 2.35 mins,<br>ES m/z 452 [MH]⁺ |
| 65 | 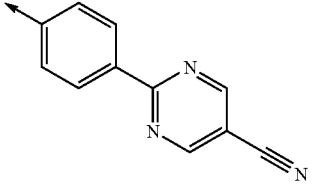 |  | C | Enantiomer 1<br>LCMS Rt 2.29 mins,<br>ES m/z 459 [MH]⁺ |
| 66 | 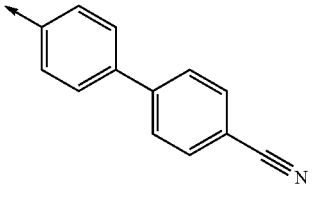 |  | B | Enantiomer 1<br>LCMS Rt 2.92 mins,<br>ES m/z 457 [MH]⁺ |
| 67 | 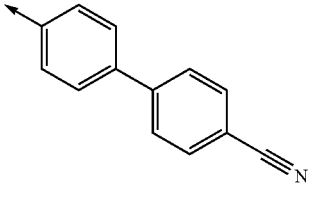 |  | B | Enantiomer 2<br>LCMS Rt 2.95 mins,<br>ES m/z 457 [MH]⁺ |
| 68 | 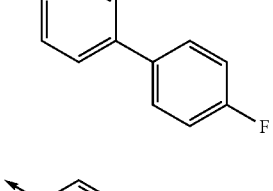 |  | B | Enantiomer 1<br>LCMS Rt 3.09 mins,<br>ES m/z 450 [MH]⁺ |
| 69 | 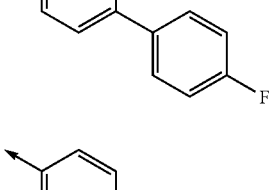 |  | B | Enantiomer 2<br>LCMS Rt 3.09 mins,<br>ES m/z 450 [MH]⁺ |
| 70 | 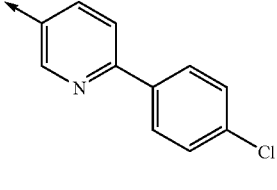 |  | B | Enantiomer 1<br>LCMS Rt 2.96 mins,<br>ES m/z 467 [MH]⁺ |

-continued

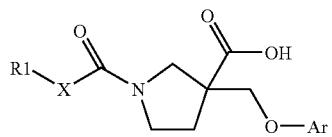

| Ex | R¹ | Ar | Method | Data |
|---|---|---|---|---|
| 71 | 2-methoxyphenyl | 5-(4-chlorophenyl)pyridin-2-yl | B | Enantiomer 2 LCMS Rt 2.96 mins, ES m/z 467 [MH]⁺ |
| 72 | 2-methoxyphenyl | 4-(5-chloropyrimidin-2-yl)phenyl | B | Enantiomer 1 1H NMR (400 MHz, METHANOL-d₄) δ ppm 2.10-2.30 (m, 1H) 2.33-2.45 (m, 1H) 3.42-3.49 (m, 1H) 3.65-3.80 (m, 3H) 3.83 (s, 3H) 4.10-4.15 (m, 1H) 4.27-4.37 (m, 1H) 6.96-7.07 (m, 4H) 7.18-7.25 (m, 1H) 7.40 (t, 1H), 8.33 (dd, 2H), 8.75 (d, 2H) ES m/z 468 [MH]⁺ |
| 73 | 2-methoxyphenyl | 4-(5-chloropyrimidin-2-yl)phenyl | B | Enantiomer 2 LCMS Rt 2.96 mins, ES m/z 468 [MH]⁺ |
| 74 | 2-methoxyphenyl | 2-(4-chlorophenyl)pyrimidin-5-yl | B | Enantiomer 1 LCMS Rt 3.02 mins, ES m/z 468 [MH]⁺ |
| 75 | 2-methoxyphenyl | 2-(4-chlorophenyl)pyrimidin-5-yl | B | Enantiomer 2 LCMS Rt 1.43 mins, ES m/z 468 [MH]⁺ |
| 76 | 2-methoxyphenyl | 5-(4-fluorophenyl)pyridin-2-yl | B | Enantiomer 1 LCMS Rt 2.85 mins, ES m/z 451 [MH]⁺ |

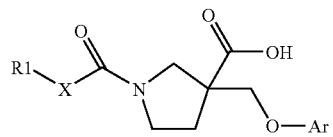

| Ex | R¹ | Ar | Method | Data |
|---|---|---|---|---|
| 77 | 2-methoxyphenyl | 4-(5-chloropyridin-2-yl)phenyl | B | Enantiomer 1<br>1H NMR (400 MHz, METHANOL-d$_4$) δ ppm 2.21-2.24 (1H, m) 2.27-2.48 (m, 1H) 3.40-5.52 (m, 2H) 3.71-3.86 (m, 2H) 3.85 (s, 3H) 6.99-7.27 (m, 5H) 7.42-7.45 (m, 1H) 7.91-7.94 (m, 2H) 8.25-8.27 (m, 1H) 8.55-8.64 (m, 1H) 8.88-8.89 (m, 1H).<br>ES m/z 466 [MH]⁺ |
| 78 | 2-methoxyphenyl | 4-(5-chloropyridin-2-yl)phenyl | B | Enantiomer 2<br>1H NMR (400 MHz, METHANOL-d$_4$) δ ppm 2.21-2.27 (1H, m) 2.27-2.48 (m, 1H) 3.41-5.52 (m, 2H) 3.70-3.89 (m, 2H) 3.85 (s, 3H) 6.99-7.27 (m, 5H) 7.41-7.45 (m, 1H) 7.90-7.94 (m, 2H) 8.25-8.30 (m, 1H) 8.54-8.64 (m, 1H) 8.86-8.89 (m, 1H).<br>ES m/z 466 [MH]⁺ |
| 79 | cyclobutyl | 4'-fluorobiphenyl-4-yl | B | Enantiomer 1<br>LCMS Rt 2.49 mins<br>ES m/z 398 [MH]⁺ |
| 80 | cyclobutyl | 4'-fluorobiphenyl-4-yl | B | Enantiomer 2<br>LCMS Rt 2.52 mins,<br>ES m/z 398 [MH]⁺ |
| 81 | cyclopentyl | 4'-fluorobiphenyl-4-yl | B | Enantiomer 1<br>LCMS Rt 2.57 mins<br>ES m/z 412 [MH]⁺ |
| 82 | cyclopentyl | 4'-fluorobiphenyl-4-yl | B | Enantiomer 2<br>LCMS Rt 2.61 mins<br>ES m/z 412 [MH]⁺ |

-continued

| Ex | R¹ | Ar | Method | Data |
|---|---|---|---|---|
| 83 | cyclopropyl-CH₂- | 4'-fluorobiphenyl-4-yl | B | Enantiomer 1<br>LCMS Rt 3.14, MS ES m/z 384 |
| 84 | cyclopropyl-CH₂- | 4'-fluorobiphenyl-4-yl | B | Enantiomer 2<br>LCMS Rt 3.13 mins<br>ES m/z 384 [MH]⁺ |
| 85[a,g] | 4-fluorophenyl- | 2-(5-carbamoylpyrimidin-2-yl)phenyl | B | Enantiomer 1<br>LCMS Rt 2.66 mins,<br>ES m/z 465 [MH]⁺ |

[a] Ethyl ester precursor prepared according to Preparation 29, using 1-(4-fluoro-benzoyl)-3-iodomethyl-pyrrolidine-3-carboxylic acid ethyl ester, enantiomer 1 (Preparation 12). Hydrolysis of crude product (hydrolysis method B) afforded product.
[b] Ethyl ester precursor prepared according to Preparation 29, using 1-(4-fluoro-benzoyl)-3-iodomethyl-pyrrolidine-3-carboxylic acid ethyl ester, enantiomer 2 (Preparation 12). Hydrolysis of crude product (hydrolysis method B) afforded product.
[c] Enantiomers separated using a Chiralpak AD-H, 70:30 heptane:IPA. Rt 36.12 mins. 94.2% e.e
[d] Enantiomers separated using a Chiralpak AD-H, 70:30 heptane:IPA. Rt 14.52 mins. 99.5% e.e
[e] Enantiomers separated using a Chiralpak AD-H, 70:30 heptane:IPA. Rt 16.86 mins. 93.0% e.e
[f] Enantiomers separated using a Chiralpak AS-H, 70:30 heptane:IPA. Rt 15.15 mins. >99.% e.e
[g] Expected product was 3-[4-(5-Cyano-pyrimidin-2-yl)-phenoxymethyl]-1-(4-fluoro-benzoyl)-pyrrolidine-3-carboxylic acid, however hydrolysis of the nitrile group was observed in addition to hydrolysis of the ethyl ester Examples 86 to 94 were prepared according to one of the methods described above for Examples 1-3, starting from the appropriate halo or tosylate compounds of formula (II) and the appropriate alcohols of formula (III) (where X=O).

| Ex | R¹ | Ar | Hydrolysis method | Data |
|---|---|---|---|---|
| 86 | 4-methylphenyl- | 4'-fluorobiphenyl-4-yl | C | Enantiomer 1<br>LCMS Rt 3.57 mins, ES m/z 450 [MH]⁺ |
| 87 | 4-methylphenyl- | 4'-fluorobiphenyl-4-yl | C | Enantiomer 2<br>LCMS Rt 3.62 mins, ES m/z 450 [MH]⁺ |

-continued

[Structure: R1-X-C(=O)-N(pyrrolidine)-C(COOH)(CH2-O-Ar)]

| Ex | R¹ | Ar | Hydrolysis method | Data |
|---|---|---|---|---|
| 88 | 4-Cl-C6H4- | 4'-F-biphenyl-4-yl | C | Enantiomer 1 LCMS Rt 3.60 mins, ES m/z 470 [MH]+ |
| 89 | 4-Cl-C6H4- | 4'-F-biphenyl-4-yl | C | Enantiomer 2 LCMS Rt 3.60 mins, ES m/z 470 [MH]+ |
| 90 | 4-F-C6H4- | 4'-F-biphenyl-4-yl | C | Enantiomer 1 LCMS Rt 3.53 mins ES m/z 454 [MH]+ |
| 91 | 4-F-C6H4- | 4'-F-biphenyl-4-yl | C | Enantiomer 2 LCMS Rt 3.53 mins ES m/z 454 [MH]+ |
| 92 | 4-MeO-C6H4- | 4'-F-biphenyl-4-yl | C | Enantiomer 1 LCMS Rt 3.48 mins ES m/z 466 [MH]+ |
| 93 | 4-MeO-C6H4- | 4'-F-biphenyl-4-yl | C | Enantiomer 2 LCMS Rt 3.48 mins ES m/z 466 [MH]+ |
| 94 | 2-MeO-C6H4- | 4'-F-biphenyl-4-yl | C | Enantiomer 1 LCMS Rt 2.48 mins, ES m/z 466 [MH]+ |

Examples 95 to 104 were prepared according to one of the methods described above for Examples 14, starting from the appropriate halo or tosylate compounds of formula (II) and the appropriate alcohols of formula (III) (where X=NH).

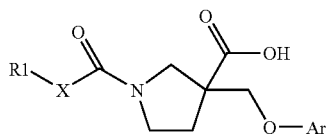

| Ex | R¹ | Ar | Hydrolysis method | Data |
|---|---|---|---|---|
| 95 | 4-methoxyphenyl | 4'-fluorobiphenyl-4-yl | B | Enantiomer 1 LCMS Rt 3.33 mins, ES m/z 465 [MH]⁺ |
| 96 | 4-methoxyphenyl | 4'-fluorobiphenyl-4-yl | B | Enantiomer 2 LCMS Rt 3.33 mins, ES m/z 465 [MH]⁺ |
| 97 | 3-methoxyphenyl | 4'-fluorobiphenyl-4-yl | B | Enantiomer 1 LCMS Rt 3.24 mins, ES m/z 465 [MH]⁺ |
| 98 | 3-methoxyphenyl | 4'-fluorobiphenyl-4-yl | B | Enantiomer 2 LCMS Rt 3.25 mins, ES m/z 465 [MH]⁺ |
| 99 | 2-chlorophenyl | 4'-fluorobiphenyl-4-yl | B | Enantiomer 1 LCMS Rt 3.40 mins, ES m/z 469 [MH]⁺ |
| 100 | 2-chlorophenyl | 4'-fluorobiphenyl-4-yl | B | Enantiomer 2 LCMS Rt 3.40 mins, ES m/z 469 [MH]⁺ |
| 101 | 4-chlorophenyl | 4'-fluorobiphenyl-4-yl | B | Enantiomer 1 LCMS Rt 3.39 mins, ES m/z 469 [MH]⁺ |
| 102 | 4-chlorophenyl | 4'-fluorobiphenyl-4-yl | B | Enantiomer 2 LCMS Rt 3.39 mins, ES m/z 469 [MH]⁺ |

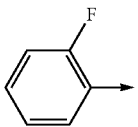

| Ex | R¹ | Ar | Hydrolysis method | Data |
|---|---|---|---|---|
| 103 | 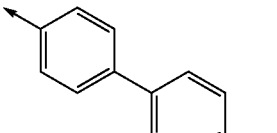 | 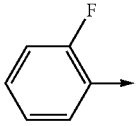 | B | Enantiomer 1 LCMS Rt 3.25 mins, ES m/z 453 [MH]⁺ |
| 104 | 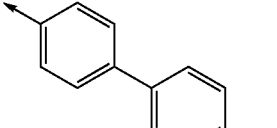 | 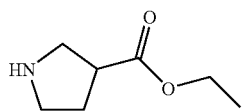 | B | Enantiomer 2 LCMS Rt 3.25 mins, ES m/z 453 [MH]⁺ |

Preparation 1: Pyrrolidine-3-carboxylic acid ethyl ester (±)

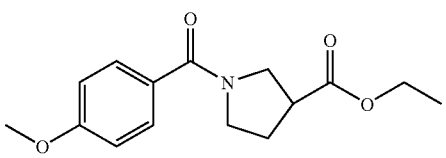

Palladium hydroxide on carbon (10% by weight, 32 g) was added to a solution of 1-benzyl-pyrrolidine-3-carboxylic acid ethyl ester (320 g, 1.37 mol) in ethanol (3000 mL) and hydrogenated (40 psi, 60° C.) for 16 hours. The reaction mixture was filtered through Arbocel™ then the filtrate was concentrated under reduced pressure to afford the title compound as a brown oil (195 g, 99%).

1H NMR (400 MHz, CDCl₃) δ: 1.23 (t, 3H), 1.90-2.00 (m, 2H), 2.79-2.88 (m, 2H) 3.00-3.12 (m, 3H), 4.10 (q, 2H)

Preparation 2: 1-(4-Methoxy-benzoyl)-pyrrolidine-3-carboxylic acid ethyl ester (±)

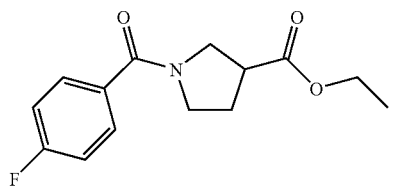

4-Methoxy-benzoyl chloride (185 mL, 1.36 mol) and triethylamine (259 mL, 1.86 mol) were added to a stirred solution of pyrrolidine-3-carboxylic acid ethyl ester (177.5 g, 1.24 mol) (see Preparation 1) in THF (2500 mL) at 10° C. The resulting mixture was stirred at room temperature for 18 hours. The reaction mixture was quenched with 10% citric acid aqueous solution (2000 mL) then ethyl acetate (2000 mL) was added. The organic layer was washed with saturated aqueous NaHCO₃ (2000 mL) and water (2000 mL), dried over magnesium sulphate then concentrated under reduced pressure to afford the title compound as a brown oil (285.3 g, 83%).

1H NMR (400 MHz, CDCl₃) δ: 1.27 (m, 3H) 2.15-2.20 (m, 2H) 3.09-3.13 (m, 1H) 3.65-3.90 (m, 4H) 3.83 (s, 3H) 4.17 (m, 2H) 6.90 (d, 2H) 7.51 (d, 2H), ES m/z 278 [MH]⁺

Preparation 3: 1-(4-Fluoro-benzoyl)-pyrrolidine-3-carboxylic acid ethyl ester (±)

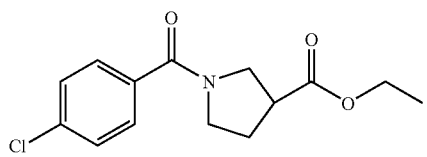

The title compound was prepared according to the method described for Preparation 2 using pyrrolidine-3-carboxylic acid ethyl ester (see Preparation 1) and 4-fluoro-benzoyl chloride to afford the title compound as a colourless oil (4.3 g, 76%).

1H NMR (400 MHz, CHLOROFORM-d) δ ppm 1.25-1.29 (t, 3H) 2.16-2.27 (m, 2H) 3.05-3.15 (m, 1H) 3.50-3.92 (m, 4H) 4.16-4.20 (m, 2H) 7.09-7.11 (m, 2H) 7.51-7.57 (m, 2H)

Preparation 4: 1-(4-Chloro-benzoyl)-pyrrolidine-3-carboxylic acid ethyl ester (±)

The title compound was prepared according to the method described for Preparation 2 using pyrrolidine-3-carboxylic acid ethyl ester (see Preparation 1) and 4-chloro-benzoyl chloride to afford the title compound as a pale yellow oil (3.02 g, 79%).

1H NMR (400 MHz, CHLOROFORM-d) d ppm 1.26-1.29 (t, 3H) 2.10-2.15 (m, 2H) 3.01-3.05 (m, 1H) 3.35-3.61 (m, 4H) 4.15-4.20 (m, 2H) 7.52-7.53 (m, 2H) 8.05-8.07 (m, 2H)

Preparation 5:
1-(2-Methoxy-benzoyl)-pyrrolidine-3-carboxylic acid ethyl ester (±)

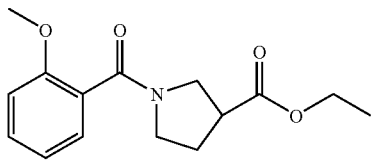

The title compound was prepared according to the method described for Preparation 2 using pyrrolidine-3-carboxylic acid ethyl ester (see Preparation 1) and 2-methoxy-benzoyl chloride to afford the title compound as a colourless oil (4.17 g, 68%).

1H NMR (400 MHz, CHLOROFORM-d) d ppm 1.20-1.29 (m, 3H) 2.10-2.27 (m, 2H) 2.98-3.28 (m, 1H) 3.30-3.37 (m, 1H) 3.45-3.48 (m, 1H) 3.66-3.91 (m, 2H) 3.82 (s, 3H) 4.11-4.19 (m, 2H) 6.89-6.97 (m, 2H) 7.33-7.35 (m, 2H). ES m/z 278 [MH]$^+$

Preparation 6:
1-(2-Ethoxy-benzoyl)-pyrrolidine-3-carboxylic acid ethyl ester (±)

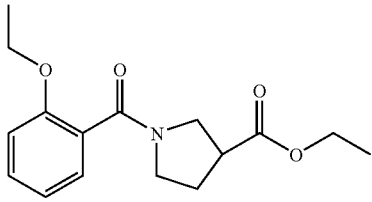

The title compound was prepared according to the method described for Preparation 2 using pyrrolidine-3-carboxylic acid ethyl ester (see Preparation 1) and 2-ethoxy-benzoyl chloride to afford the title compound as a pale yellow oil (5.13 g, 83%).

1H NMR (400 MHz, CHLOROFORM-d) d ppm 1.21-1.26 (m, 3H) 1.35-1.38 (m, 3H) 2.02-2.24 (m, 4H) 2.97-3.12 (m, 1H) 3.29-3.38 (m, 1H) 3.48 (d, 1H) 3.60-3.95 (m, 2H) 4.04-4.19 (m, 2H) 6.86-6.89 (m, 1H) 6.94 (t, 1H) 7.25-7.32 (m, 2H). ES m/z 292 [MH]$^+$

Preparation 7:
1-(4-Methoxy-benzoyl)-pyrrolidine-3,3-dicarboxylic acid diethyl ester

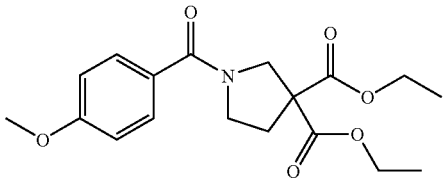

Lithium bis(trimethylsilyl)amide (1000 mL of a 1.0M solution in tetrahydrofuran, 1.0 mol) was added to a stirred solution of 1-(4-methoxy-benzoyl)-pyrrolidine-3-carboxylic acid ethyl ester (±) (268 g, 0.97 mol) (see Preparation 2) in THF (1600 mL) at −70° C. The mixture was stirred for 20 mins at −70° C. then ethyl chloroformate (104 mL, 1.09 mol) was added over 15 minutes. The resulting mixture was stirred at −60° C. for 1 hour. The reaction mixture was quenched with 10% citric acid aqueous solution (1200 mL) at −50° C. then warmed to room temperature. The organic layer was separated, washed with saturated aqueous NaHCO$_3$ (1200 mL) and water (1200 mL) then concentrated under reduced pressure to afford the title compound as an orange oil (316.0 g, 94%).

LCMS Rt 2.07 mins
1H NMR (400 MHz, CDCl$_3$) δ: 1.20 (m, 6H), 2.33-2.50 (m, 2H), 3.55-3.72 (m, 2H), 3.77 (s, 3H), 3.90-4.21 (m, 6H), 6.84 (d, 2H), 7.44 (d, 2H).

Preparation 8:
1-(4-Methoxy-benzoyl)-pyrrolidine-3,3-dicarboxylic acid ethyl ester (non racemic)

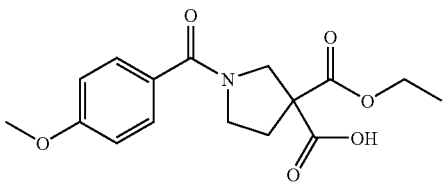

1-(4-Methoxy-benzoyl)-pyrrolidine-3,3-dicarboxylic acid diethyl ester (679.9 g, 1.95 mol) (see Preparation 7) in acetonitrile (1000 mL) was added to pH 7 buffer solution (10 L, 0.1M potassium phosphate) then Savinase 16T Type W enzyme (3200 g) was added and the resulting slurry was heated to 30° C. The pH of the reaction mixture was kept at 8.5 using a pH stat (TIM856 Titration Manager) and stirred for 6 days. Water (6 L) and ethyl acetate (12 L) was added to the reaction mixture then acidified to pH1 using 2M HCl aqueous solution (6 L). This was filtered through Arbocel™ and the organic layer was separated, washed with water (5 L) then extracted with 0.5M NaOH aqueous solution (7 L). The aqueous phase was acidified using 2M HCl aqueous solution (5 L) and extracted with ethyl acetate (6.5 L). The organic phase was concentrated under reduced pressure to afford the title compound as an orange oil (334.3 g, 53%). (92.9:7.1 ratio of isomers)

LCMS Rt 2.38 mins, ES m/z 310 [MH]$^+$

Preparation 9: 3-Hydroxymethyl-1-(4-methoxy-benzoyl)-pyrrolidine-3-carboxylic acid (non racemic)

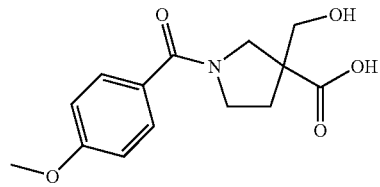

Lithium borohydride (207 mL, 414.0 mmol, 2M in THF) was added to a stirred solution of 1-(4-methoxy-benzoyl)-pyrrolidine-3,3-dicarboxylic acid ethyl ester (88.63 g, 275.8 mmol) (see Preparation 8) in isopropyl alcohol (600 mL) at 5° C. The mixture was stirred for 4 hours at 5° C. then quenched with 2M HCl aqueous solution (300 mL) and stirred for 15 minutes. The solvent volume was reduced by concentration under reduced pressure and the aqueous residue was extracted with ethyl acetate (300 mL). The organic layer was separated, washed with water (300 mL) then concentrated under reduced pressure to afford a pale brown solid. This was triturated with acetonitrile to afford the title compound as a white solid (27.8 g, 36%). (99.3:0.7 ratio of isomers)

LCMS Rt 1.197 mins

1H NMR (400 MHz, DMSO-d6) δ: 1.84-1.91 (m, 1H), 2.07-2.13 (m, 1H), 3.40-3.64 (m, 5H), 3.75 (s, 2H), 3.78 (s, 3H), 6.96 (d, 2H), 7.47 (d, 2H).

Preparation 10: 3-Hydroxymethyl-1-(4-methoxy-benzoyl)-pyrrolidine-3-carboxylic acid ethyl ester (non racemic)

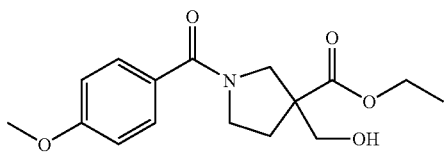

Acetyl chloride (80.2 mL, 1130 mmol) was added to a suspension of 3-hydroxymethyl-1-(4-methoxy-benzoyl)-pyrrolidine-3-carboxylic acid (210.0 g, 751.9 mmol) (see Preparation 9) in ethanol (2100 mL) and the reaction mixture was heated at 80° C. for 4 hours. Water (200 mL) was added then ethanol was removed by concentration under reduced pressure. The aqueous residue was partitioned between ethyl acetate (2 L) and saturated aqueous NaHCO₃ (1500 mL). The organic layer was separated, washed with water (1500 mL) then concentrated under reduced pressure to afford the title compound as a colourless oil (140.7 g, 61%). (99.3:0.7 ratio of isomers)

LCMS Rt 1.564 mins

Preparation 11: 1-(4-Methoxy-benzoyl)-3-(toluene-4-sulfonyloxymethyl)-pyrrolidine-3-carboxylic acid ethyl ester (non racemic)

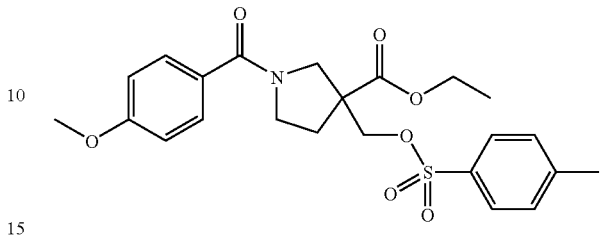

4-Toluenesulphonyl chloride (131 g, 687 mmol) and trimethylamine hydrochloride (43.8 g, 458 mmol) were added to 3-hydroxymethyl-1-(4-methoxy-benzoyl)-pyrrolidine-3-carboxylic acid ethyl ester (140.7 g, 457.8 mmol) (see Preparation 10) and triethylamine (160 mL, 1140 mmol) in dichloromethane (1400 mL) at 0° C. The reaction mixture was stirred at 0° C. for 4 hours then at RT for 18 hours. Cooled to 0° C. and trimethylamine hydrochloride (21.9 g, 229 mmol) was added, followed by 4-toluenesulphonyl chloride (17.45 g, 91.6 mmol). The reaction mixture was stirred at 0° C. for 4 hours. Water (500 mL) was added and stirred for 10 minutes. The reaction mixture was washed with 2M citric acid aqueous solution (1400 mL) and saturated aqueous NaHCO₃ (1400 mL). The organic layer was separated, washed with water (1300 mL) then concentrated under reduced pressure to afford the title compound as a brown oil (215.15 g, 100%).

LCMS Rt 2.29 mins

Preparation 12: 1-(4-Fluoro-benzoyl)-3-iodomethyl-pyrrolidine-3-carboxylic acid ethyl ester (±)

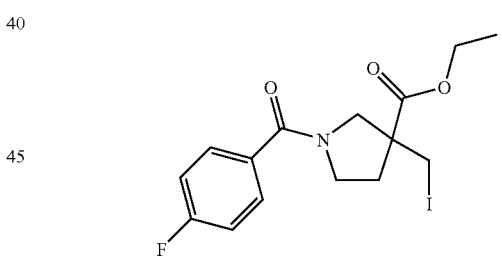

To a stirred solution of 1-(4-fluoro-benzoyl)-pyrrolidine-3-carboxylic acid ethyl ester (4.20 g, 15.8 mmol) (see Preparation 3) in tetrahydrofuran (50 mL) at −78° C. under a nitrogen atmosphere, was added lithium bis(trimethylsilyl)amide (19.0 mL of a 1.0M solution in tetrahydrofuran, 19.0 mmol). The resulting mixture was stirred at −78° C. for 30 minutes and then diiodomethane was added (1.40 mL, 17.4 mmol). The mixture was allowed to warm to room temperature and stir for a further 16 hours. The mixture was quenched with 10% aqueous citric acid (50 mL) and extracted with ethyl acetate (2×100 mL). The combined organics were washed with brine (100 mL), dried over magnesium sulphate, filtered and concentrated under reduced pressure. The crude material was purified using silica gel column chromatography, using a gradient eluent of 30% ethyl acetate in heptane to 50% ethyl acetate in heptane to afford the title compound as a colourless oil (4.2 g, 65%).

1H NMR (400 MHz, CHLOROFORM-d) δ ppm 1.27-1.30 (m, 3H) 1.90-2.17 (m, 2H), 2.47-2.53 (m, 2H) 3.30-4.24 (m, 6H) 7.09-7.11 (m, 2H) 7.52-7.55 (m, 2H) ES m/z 406 [MH]+

The enantiomers of 2.6 g of title compound were separated using a Chiralpak IC 70:30 heptane:IPA.

Peak 1 Yield 686 mg, 98.99% e.e. (first eluting peak at 14.95 mins) —Enantiomer 1

Peak 2 Yield 615 mg, 98.93% e.e. (second eluting peak at 16.82 mins) —Enantiomer 2

Preparation 13: 1-(4-Chloro-benzoyl)-3-iodomethyl-pyrrolidine-3-carboxylic acid ethyl ester (±)

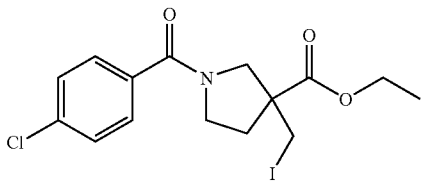

The title compound was prepared according to the method described for Preparation 12 using 1-(4-chloro-benzoyl)-pyrrolidine-3-carboxylic acid ethyl ester (see Preparation 4) to afford the title compound as a yellow oil (531 mg, 60%).

1H NMR (400 MHz, DMSO-$d_6$) δ ppm 1.14-1.26 (m, 3H) 1.95-2.36 (m, 2H) 2.30-2.36 (m, 2H) 3.35-4.20 (m, 6H) 7.49-7.59 (m, 2H) ES m/z 422 [MH]+

Preparation 14: 3-Iodomethyl-1-(4-methoxy-benzoyl)-pyrrolidine-3-carboxylic acid ethyl ester (±)

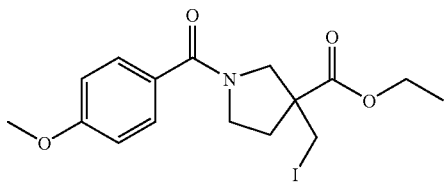

The title compound was prepared according to the method described for Preparation using 1-(4-methoxy-benzoyl)-pyrrolidine-3-carboxylic acid ethyl ester (see Preparation 2) to afford the title compound as a yellow oil (5.09 g, 27%).

1H NMR (400 MHz, CHLOROFORM-d) δ ppm 1.24-1.36 (m, 3H) 1.90-2.10)m, 2H) 2.46-2.52 (m, 2H) 3.30-4.24 (m, 6H) 3.84 (s, 3H) 6.92 (d, 2H) 7.51 (d, 2H)

Preparation 15: 3-Iodomethyl-1-(2-methoxy-benzoyl)-pyrrolidine-3-carboxylic acid ethyl ester (±)

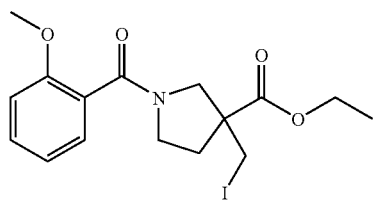

The title compound was prepared according to the method described for Preparation using 1-(2-methoxy-benzoyl)-pyrrolidine-3-carboxylic acid ethyl ester (see Preparation 5) to afford the title compound as a pale yellow oil (4.80 g, 61%)

1H NMR (400 MHz, CHLOROFORM-d) δ ppm 1.27-1.35 (m, 3H) 2.01-2.13 (m, 2H) 2.46-2.52 (m, 2H) 3.34-3.45 (m, 2H), 3.70-3.77 (m, 2H) 3.85 (d, 3H) 4.20-4.29 (m, 2H) 6.90-7.05 (m, 2H) 7.27 (dd, 1H) 7.33-7.40 (m, 1H)

Preparation 16: 1-(2-Ethoxy-benzoyl)-3-iodomethyl-pyrrolidine-3-carboxylic acid ethyl ester (±)

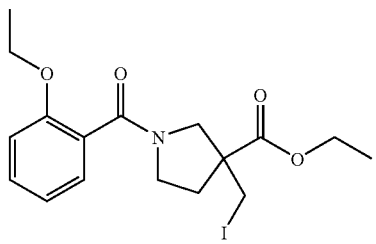

The title compound was prepared according to the method described for Preparation 12 using 1-(2-ethoxy-benzoyl)-pyrrolidine-3-carboxylic acid ethyl ester (see Preparation 6) to afford the title compound as a pale yellow oil (1.68 g, 24%)

1H NMR (400 MHz, CHLOROFORM-d) δ ppm 1.26-1.33 (m, 3H) 1.39-1.62 (m, 3H) 1.99-2.04 (m, 1H) 2.07-2.15 (m, 1H) 2.46-2.51 (m, 2H) 3.36-3.46 (m, 2H) 3.73-3.83 (m, 2H) 4.04-4.30 (m, 4H) 6.91 (t, 1H) 6.98 (td, 1H) 7.26-7.37 (m, 2H)

Preparation 17: 4-(5-Chloro-pyridin-2-yl)-phenol

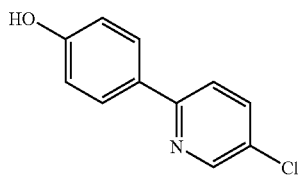

Palladium(0),tetrakis(triphenylphosphine) (4.69 g, 4.05 mmol) was added to a stirred suspension of 2,5-dichloropyridine (12.0 g, 81.08 mmol), 4-hydroxybenzene boronic acid (11.2 g, 81.1 mmol) and potassium carbonate (11.2 g, 81.1 mmol) in dioxane (100 mL) and water (100 mL). The mixture was refluxed for 2 hours, then partitioned between diethyl ether (100 mL) and water (100 mL). The organics were washed with brine (100 mL), dried over magnesium sulphate and concentrated under reduced pressure. The residue was purified by column chromatography on silica gel, eluting with 4% methanol in dichloromethane, to afford the title compound as an off-white solid (15.5 g, 81%).

1H NMR (400 MHz, METHANOL-d4) δ ppm 6.87 (d, 2H) 7.73-7.82 (m, 3H) 8.50 (s, 1H). ES m/z 204, 206 [MH]−

Preparation 18: 6-(4-Hydroxy-phenyl)-nicotinonitrile

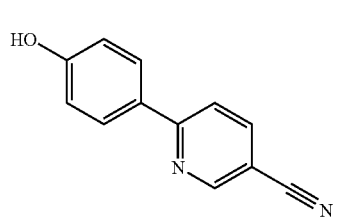

The title compound was prepared according to the method described for Preparation 17 using 4-hydroxybenzene boronic acid and 2-bromo-5-cyanopyridine to afford the title compound as a white solid (250 mg, 23%)

1H NMR (400 MHz, METHANOL-d4) δ ppm 6.85-6.91 (d, 2H), 7.90-8.15 (m, 4H) 8.83 (s, 1H). ES m/z 204, 195 [MH]⁻

Preparation 19: 4-(5-Chloro-pyrimidin-2-yl)-phenol

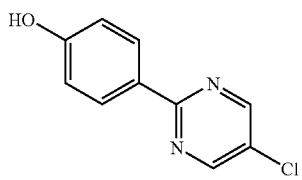

The title compound was prepared according to the method described for Preparation 17 using 4-hydroxybenzene boronic acid and 2,5-dichloro-pyrimidine to afford the title compound as a pale yellow solid (1.91 g, 29%)

1H NMR (400 MHz, DMSO-d6) d ppm 6.88 (q, J=4.94 Hz) 6.88 (m, 2H) 8.20 (m, 2H), 8.89 (s, 2H) 10.02 (s, 1H)

Preparation 20: 4-(5-Fluoro-pyrimidin-2-yl)-phenol

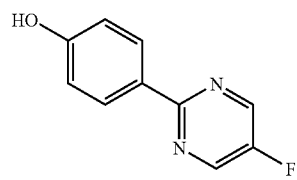

The title compound was prepared according to the method described for Preparation 17 using 4-hydroxybenzene boronic acid and 2-chloro-5-fluoro-pyrimidine to afford the title compound as a white solid (575 mg, 42%)

1H NMR (400 MHz, METHANOL-d4) δ ppm 6.83-6.87 (m, 2H), 8.19-8.23 (m, 2H) 8.67 (s, 2H). ES m/z 189 [MH]⁻

Preparation 21: 6-(4-Fluoro-phenyl)-pyridin-3-ol

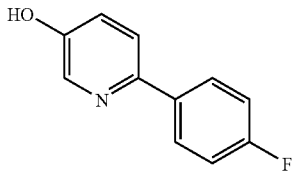

The title compound was prepared according to the method described for Preparation 17 using 2-bromo-5-hydroxypyridine and 4-fluorophenylboronic acid to afford the title compound as an off-white solid (270 mg, 51%)

1H NMR (400 MHz, METHANOL-d4) δ ppm 7.13-7.17 (m, 2H), 7.26-7.29 (m, 1H), 7.64-7.66 (m, 1H), 7.83-7.87 (dd, 2H), 8.14-8.15 (m, 1H). ES m/z 188 [MH]⁻

Preparation 22: 4-(5-Hydroxy-pyridin-2-yl)-benzonitrile

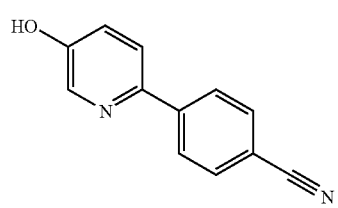

The title compound was prepared according to the method described for Preparation 17 using 2-bromo-5-hydroxypyridine and 4-cyanophenylboronic acid to afford the title compound as a yellow solid (300 mg, 26%)

1H NMR (400 MHz, METHANOL-d₄) δ ppm 7.30 (dd, 1H) 7.77-7.81 (m, 3H) 8.06 (m, 2H) 8.22 (m, 1H). ES m/z 195 [MH]⁻

Preparation 23: 6-(4-Chloro-phenyl)-pyridin-3-ol

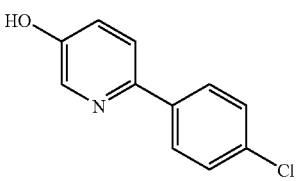

The title compound was prepared according to the method described for Preparation 17 using 4-chlorophenylboronic acid and 2-bromo-5-hydroxypyridine to afford the title compound as an off-white solid (1.3 g, 73%)

LCMS Rt 2.49 mins, ES m/z 204 [MH]−

Preparation 24: 2-(4-Chloro-phenyl)-5-methoxy-pyrimidine

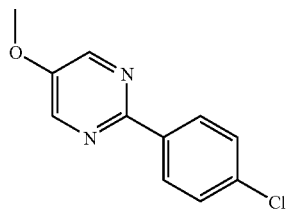

The title compound was prepared according to the method described for Preparation 17 using 2-chloro-5-methoxy-pyrimidine and 4-chlorophenylboronic acid to afford the title compound as an off-white solid (4.05 g, 40%)

Preparation 25: 5-(4-Chloro-phenyl)-pyrazin-2-ol

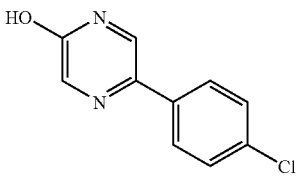

To a stirred solution of (4-chloro-phenyl)-oxo-acetaldehyde (300 mg, 1.69 mmol) in methanol (15 mL) was added 2-amino-acetamide (187 mg, 1.69 mmol). The resulting mixture was cooled to −30° C. and 12.5M aqueous sodium hydroxide solution (0.3 mL) added. The resulting mixture was allowed to warm to −5° C. and was stirred at this temperature for 2 hours, followed by stirring at room temperature for 2 hours. Concentrated aqueous hydrogen chloride (0.3 mL) was added, followed by saturated sodium bicarbonate solution (1.0 mL). The reaction mixture was filtered and the resulting solid was washed with water (10 mL) and dried in a vacuum oven to afford the title compound as a brown solid (130 mg, 37%)

1H NMR (400 MHz, DMSO-d6) d ppm 7.47 (m, 1H) 7.57 (m, 1H), 7.88-7.96 (m, 3H), 8.11 (s, 1H)

Preparation 26: 5-(4-Fluoro-phenyl)-pyrazin-2-ol

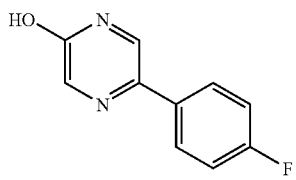

The title compound was prepared according to the method described for Preparation 25 using (4-fluoro-phenyl)-oxo-acetaldehyde and 2-amino-acetamide to afford the title compound as a pale yellow oil (2.33 g, 42%).

1H NMR (400 MHz, CHLOROFORM-d) d ppm 7.12-7.18 (m, 2H) 7.62 (s, 1H) 7.73-7.79 (m, 2H) 8.35 (s, 1H), ES m/z 189 [MH]−

Preparation 27: 2-(4-Chloro-phenyl)-pyrimidin-5-ol

To a stirred solution of 2-(4-chloro-phenyl)-5-methoxy-pyrimidine (100 mg, 0.45 mmol) was added hydrogen bromide in acetic acid (3 mL of a 33% by weight solution). The resulting mixture was stirred at reflux for 4 hours. The mixture was then partitioned between diethyl ether (25 mL) and saturated sodium hydrogen carbonate solution (25 mL). The organics were further washed with water (25 mL), brine (25 mL), dried over magnesium sulphate, filtered and concentrated under reduced pressure. The resulting precipitate was washed with pentane (10 mL) and then dried under reduced pressure to afford the title compound as a white solid in 88% yield, 82 mg.

1H NMR (400 MHz, CHLOROFORM-d) d ppm 7.43-7.46 (m, 2H) 7.44-7.46 (m, 2H) 8.29-8.30 (m, 2H) 8.30 8.48 (s, 2H)

Preparation 28a: 3-(4'-Cyano-biphenyl-4-yloxymethyl)-1-(4-methoxy-benzoyl)-pyrrolidine-3-carboxylic acid ethyl ester (non racemic)

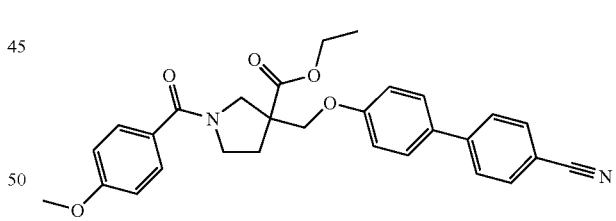

4'-hydroxy-4-biphenyl carbonitrile (107.0 g, 549 mmol) and potassium carbonate (94.9 g, 687 mmol) were added to a stirred solution of 1-(4-methoxy-benzoyl)-3-(toluene-4-sulfonyloxymethyl)-pyrrolidine-3-carboxylic acid ethyl ester (211.3 g, 457.8 mmol) (see Preparation 11) in dimethylsulphoxide (422 mL). The reaction mixture was heated at 80° C. for 18 hours then partitioned between ethyl acetate (2000 mL) and water (2000 mL). The organic layer was washed with water (2000 mL) then separated and concentrated under reduced pressure to afford the title compound as an orange oil (207.7 g, 93%). (>99.5% e.e.)

LCMS Rt 2.571 mins

Preparation 28b: 3-(4'-Cyano-biphenyl-4-yloxymethyl)-1-(4-methoxy-benzoyl)-pyrrolidine-3-carboxylic acid ethyl ester (±)

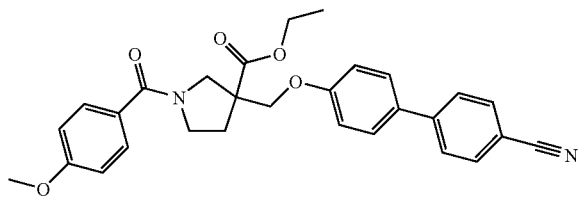

The title compound was prepared according to the method described for Preparation 29 using 4'-hydroxy-4-biphenyl carbonitrile and 3-Iodomethyl-1-(4-methoxy-benzoyl) pyrrolidine-3-carboxylic acid ethyl ester (Preparation 14) to afford the racemate as a white solid (124 mg, 71%)

The enantiomers were separated using a Chiralpak IA 55:45 heptane:IPA.

Peak 1 Yield 28 mg, 99.5% e.e. (first eluting peak at 17.7 mins)

Peak 2 Yield 23.5 mg, 95.8% e.e. (second eluting peak at 20.6 mins)

Preparation 29: 3-(4'-Cyano-biphenyl-4-yloxymethyl)-1-(4-fluoro-benzoyl)-pyrrolidine-3-carboxylic acid ethyl ester (±)

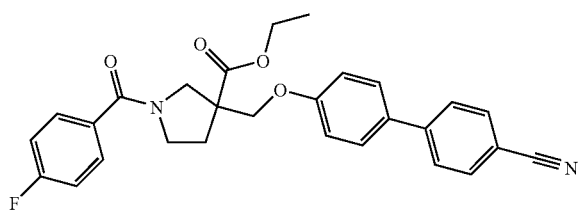

4'-Hydroxy-4-biphenyl carbonitrile (329 mg, 1.68 mmol) and potassium carbonate (317 mg, 2.30 mmol) were added to a stirred solution of 1-(4-fluoro-benzoyl)-3-iodomethyl-pyrrolidine-3-carboxylic acid ethyl ester (620 mg, 1.53 mmol) (see Preparation 12) in dimethylformamide (7 mL). The reaction mixture was heated at 80° C. for 18 hours then partitioned between ethyl acetate (100 mL) and water (100 mL). The organic layer was washed with water (2000 mL), dried over magnesium sulfate then concentrated under reduced pressure. The residue was purified by column chromatography on silica gel, eluting with 3:1→1:1 heptane:EtOAc to afford the title compound as a white solid (517 mg, 71%).

The enantiomers were separated using a Chiralpak IB 55:45 heptane:IPA.

Peak 1 Yield 140 mg, 96.7% ee (first eluting peak at 11.8 mins)

Peak 2 Yield 132 mg, 98.8% ee (second eluting peak at 15.4 mins)

Preparation 30: 3-[6-(4-Chloro-phenyl)-pyridin-3-yloxymethyl]-1-(4-fluoro-benzoyl)-pyrrolidine-3-carboxylic acid ethyl ester (±)

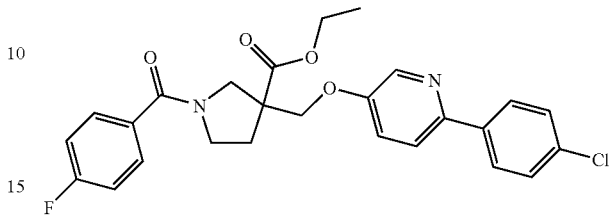

The title compound was prepared according to the method described for Preparation 29 using 6-(4-chloro-phenyl)-pyridin-3-ol (Preparation 23) and 1-(4-fluoro-benzoyl)-3-iodomethyl-pyrrolidine-3-carboxylic acid ethyl ester (Preparation 12) to afford the racemate as a pale yellow solid (128 mg, 53.6%)

The enantiomers were separated using a Chiralpak IB 55:45 heptane:IPA.

Peak 1 Yield 15 mg, 99.5% ee (first eluting peak at 16.9 mins)

Peak 2 Yield 20 mg, 98.0% ee (second eluting peak at 26.2 mins)

Preparation 31: 3-[2-(4-Chloro-phenyl)-pyrimidin-5-yloxymethyl]-1-(4-fluoro-benzoyl)-pyrrolidine-3-carboxylic acid ethyl ester (±)

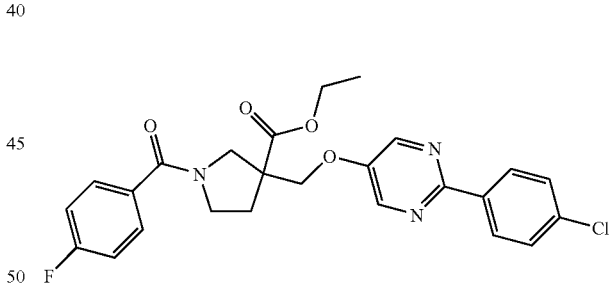

The title compound was prepared according to the method described for Preparation 29 using 2-(4-chloro-phenyl)-pyrimidin-5-ol (Preparation 27) and 1-(4-fluoro-benzoyl)-3-iodomethyl-pyrrolidine-3-carboxylic acid ethyl ester (Preparation 12) to afford the racemate as a pale yellow solid (89 mg, 37%)

The enantiomers were separated using a Chiralpak IA 55:45 heptane:IPA.

Peak 1 Yield 28 mg, 98.3% ee (first eluting peak at 10.8 mins)

Peak 2 Yield 18 mg, 99.5% ee (second eluting peak at 14.8 mins)

Preparation 32: 3-[4-(5-Chloro-pyridin-2-yl)-phenoxymethyl]-1-(4-fluoro-benzoyl)-pyrrolidine-3-carboxylic acid ethyl ester (±)

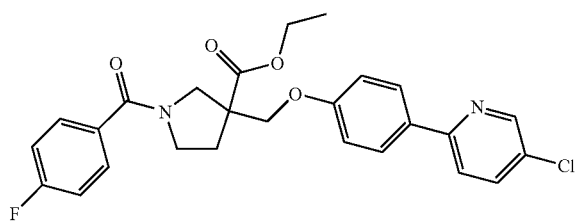

The title compound was prepared according to the method described for Preparation 29 using 4-(5-chloro-pyridin-2-yl)-phenol (Preparation 17) and 1-(4-fluoro-benzoyl)-3-iodomethyl-pyrrolidine-3-carboxylic acid ethyl ester (Preparation 12) to afford the racemate as a white solid (127 mg, 53.2%)

The enantiomers were separated using a Chiralpak 1B 55:45 heptane:IPA.

Peak 1 Yield 43 mg, 99.5% ee (first eluting peak at 8.6 mins)

Peak 2 Yield 51 mg, 99.5% ee (second eluting peak at 10.3 mins)

Preparation 33: 3-[4-(5-Chloro-pyrimidin-2-yl)-phenoxymethyl]-1-(4-fluoro-benzoyl)-pyrrolidine-3-carboxylic acid ethyl ester (±)

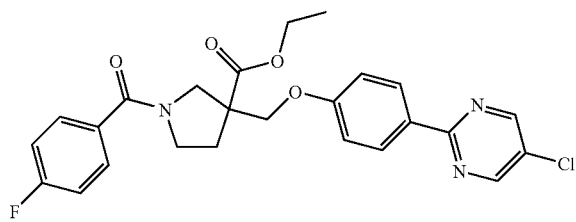

The title compound was prepared according to the method described for Preparation 29 using 4-(5-chloro-pyrimidin-2-yl)-phenol (Preparation 19) and 1-(4-fluoro-benzoyl)-3-iodomethyl-pyrrolidine-3-carboxylic acid ethyl ester (Preparation 12) to afford the racemate as a pale yellow solid (103 mg, 43.1%)

The enantiomers were separated using a Chiralpak IC 100% MeOH.

Peak 1 Yield 29 mg, 99.1% ee (first eluting peak at 9.7 mins)

Peak 2 Yield 28 mg >99.5% ee (second eluting peak at 11.6 mins)

Preparation 34: 1-(4-Chloro-benzoyl)-3-(4'-cyano-biphenyl-4-yloxymethyl)-pyrrolidine-3-carboxylic acid ethyl ester (±)

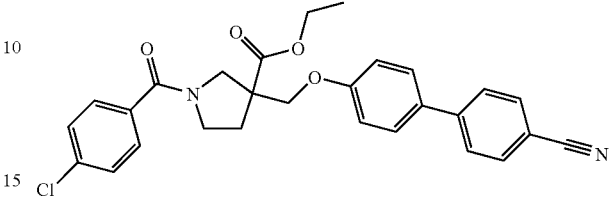

The title compound was prepared according to the method described for Preparation 29 using 1-(4-chloro-benzoyl)-3-iodomethyl-pyrrolidine-3-carboxylic acid ethyl ester (Preparation 13) and 4'-hydroxy-4-biphenyl carbonitrile to afford the racemate as a white solid (181 mg, 79.6%)

The enantiomers were separated using a Chiralpak IA 55:45 heptane:IPA.

Peak 1 Yield 52 mg, 93.1% ee (first eluting peak at 14.4 mins)

Peak 2 Yield 46 mg, 99.5% ee (second eluting peak at 20.3 mins)

Preparation 35: 1-(4-Chloro-benzoyl)-3-[4-(5-chloro-pyridin-2-yl)-phenoxymethyl]-pyrrolidine-3-carboxylic acid ethyl ester (±)

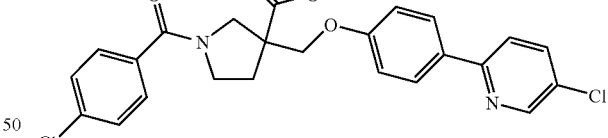

The title compound was prepared according to the method described for Preparation 29 using 4-(5-chloro-pyridin-2-yl)-phenol (Preparation 17) and 1-(4-chloro-benzoyl)-3-iodomethyl-pyrrolidine-3-carboxylic acid ethyl ester (Preparation 13) to afford the racemate as a white solid (63 mg, 30%)

The enantiomers were separated using a Chiralpak IB 55:45 heptane:IPA.

Peak 1 Yield 12 mg, 97.7% ee (first eluting peak at 10.60 mins)

Peak 2 Yield 12 mg, 69.7% ee (second eluting peak at 14.7 mins)

Preparation 36: 1-(4-Chloro-benzoyl)-3-[4-(5-chloro-pyrimidin-2-yl)-phenoxymethyl]-pyrrolidine-3-carboxylic acid ethyl ester (±)

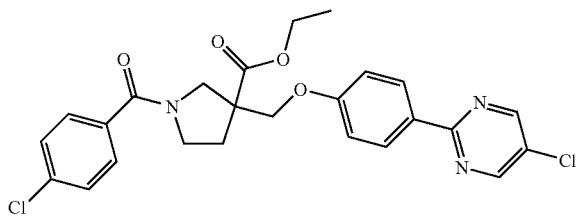

The title compound was prepared according to the method described for Preparation 29 using 4-(5-chloro-pyrimidin-2-yl)-phenol (Preparation 19) and 1-(4-chloro-benzoyl)-3-iodomethyl-pyrrolidine-3-carboxylic acid ethyl ester (Preparation 13) to afford the racemate as a white solid (153 mg, 65.7%)

The enantiomers were separated using a Chiralpak IA 55:45 heptane:IPA.

Peak 1 Yield 56 mg, 94.4% ee (first eluting peak at 12.30 mins)

Peak 2 Yield 47 mg, 99.3% ee (second eluting peak at 18.90 mins)

Preparation 37: 1-(4-Chloro-benzoyl)-3-[6-(4-chloro-phenyl)-pyridin-3-yloxymethyl]-pyrrolidine-3-carboxylic acid ethyl ester

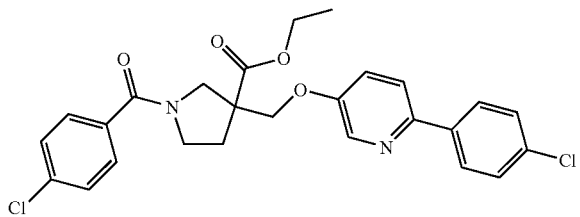

The title compound was prepared according to the method described for Preparation 29 using 6-(4-chloro-phenyl)-pyridin-3-ol (Preparation 23) and 1-(4-chloro-benzoyl)-3-iodomethyl-pyrrolidine-3-carboxylic acid ethyl ester (Preparation 13) to afford the racemate as a white solid (56 mg, 27%)

The enantiomers were separated using a Chiralpak IA 55:45 heptane:IPA.

Peak 1 Yield 11.04 mg, 99.2% ee (first eluting peak at 18.4 mins)

Peak 2 Yield 10.4 mg, 98.5% ee (second eluting peak at 29.8 mins)

Preparation 38: 1-(4-Chloro-benzoyl)-3-(4'-fluoro-biphenyl-4-yloxymethyl)-pyrrolidine-3-carboxylic acid ethyl ester (±)

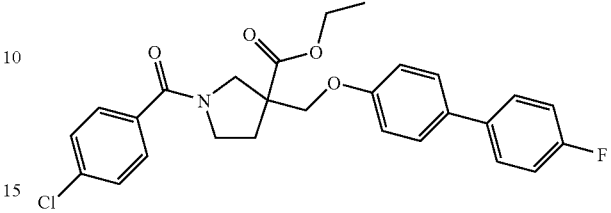

The title compound was prepared according to the method described for Preparation 29 using 4'-fluoro-biphenyl-4-ol and 1-(4-chloro-benzoyl)-3-iodomethyl-pyrrolidine-3-carboxylic acid ethyl ester (Preparation 13) to afford the racemate as a white solid (84 mg, 37%)

The enantiomers were separated using a Chiralpak IB 55:45 heptane:IPA.

Peak 1 Yield 20 mg, 97% ee (first eluting peak at 8.02 mins)

Peak 2 Yield 23 mg, 98.6% ee (second eluting peak at 10.50 mins)

Preparation 39: 3-(4'-Fluoro-biphenyl-4-yloxymethyl)-1-(4-methoxy-benzoyl)-pyrrolidine-3-carboxylic acid ethyl ester (±)

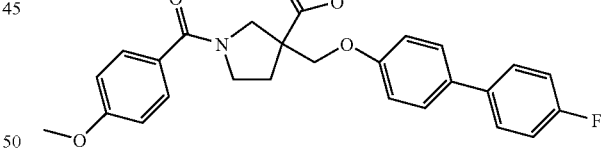

The title compound was prepared according to the method described for Preparation 29 using 4'-fluoro-biphenyl-4-ol and 3-iodomethyl-1-(4-methoxy-benzoyl)-pyrrolidine-3-carboxylic acid ethyl ester (Preparation 14) to afford the racemate as a white solid (162 mg, 73.2%)

The enantiomers were separated using a Chiralpak IB 55:45 heptane:IPA.

Peak 1 Yield 67 mg, 97.4% e.e. (first eluting peak at 9.70 mins)

Peak 2 Yield 68 mg, 98.7% e.e. (second eluting peak at 14.9 mins)

Preparation 40: 3-[4-(5-Chloro-pyrimidin-2-yl)-phenoxymethyl]-1-(4-methoxy-benzoyl)-pyrrolidine-3-carboxylic acid ethyl ester (±)

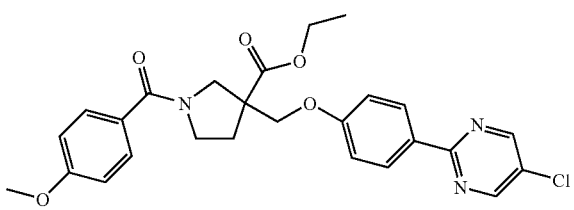

The title compound was prepared according to the method described for Preparation 29 using 4-(5-chloro-pyrimidin-2-yl)-phenol (Preparation 19) and 3-iodomethyl-1-(4-methoxy-benzoyl)-pyrrolidine-3-carboxylic acid ethyl ester (Preparation 14) to afford the racemate as a white solid (245 mg, 76%)

The enantiomers were separated using a Chiralpak IB 55:45 heptane:IPA.

Peak 1 Yield 60 mg, 96.7% e.e. (first eluting peak at 12.1 mins)

Peak 2 Yield 51 mg, 98.8% e.e. (second eluting peak at 20.6 mins)

Preparation 41: 3-[6-(4-Chloro-phenyl)-pyridin-3-yloxymethyl]-1-(4-methoxy-benzoyl)-pyrrolidine-3-carboxylic acid ethyl ester (±)

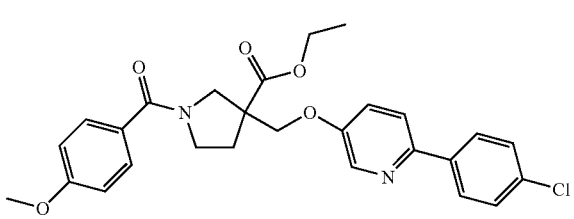

The title compound was prepared according to the method described for Preparation 29 using 6-(4-chloro-phenyl)-pyridin-3-ol (Preparation 23) and 3-iodomethyl-1-(4-methoxy-benzoyl)-pyrrolidine-3-carboxylic acid ethyl ester (Preparation 14) to afford the racemate as a white solid (94 mg, 46%)

The enantiomers were separated using a Chiralpak IB 55:45 heptane:IPA.

Peak 1 Yield 17 mg, >99.5% e.e. (first eluting peak at 14.27 mins)

Peak 2 Yield 8 mg, 99.3% e.e. (second eluting peak at 22.3 mins)

Preparation 42: 3-[4-(5-Chloro-pyridin-2-yl)-phenoxymethyl]-1-(4-methoxy-benzoyl)-pyrrolidine-3-carboxylic acid ethyl ester (±)

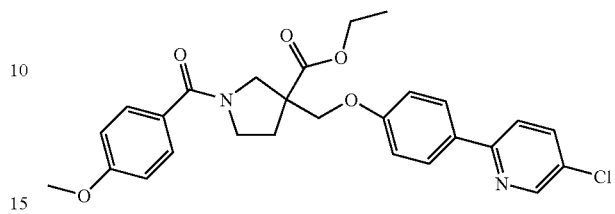

The title compound was prepared according to the method described for Preparation 29 using 4-(5-chloro-pyridin-2-yl)-phenol (Preparation 17) and 3-iodomethyl-1-(4-methoxy-benzoyl)-pyrrolidine-3-carboxylic acid ethyl ester (Preparation 14) to afford the racemate as a white solid (133 mg, 65.2%)

The enantiomers were separated using a Chiralpak IB 55:45 heptane:IPA.

Peak 1 Yield 23 mg, >99.5% e.e. (first eluting peak at 12.2 mins)

Peak 2 Yield 16 mg, 99.4% e.e. (second eluting peak at 18.5 mins)

Preparation 43: 3-[4-(5-Cyano-pyridin-2-yl)-phenoxymethyl]-1-(2-methoxy-benzoyl)-pyrrolidine-3-carboxylic acid ethyl ester (±)

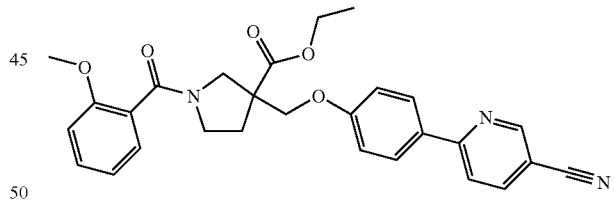

The title compound was prepared according to the method described for Preparation 29 using 6-(4-hydroxy-phenyl)-nicotinonitrile (Preparation 18) and 3-iodomethyl-1-(2-methoxy-benzoyl)-pyrrolidine-3-carboxylic acid ethyl ester (Preparation 15) to afford the racemate as a white solid (112 mg, 64.6%)

The enantiomers were separated using a Chiralpak IA 55:45 heptane:IPA.

Peak 1 Yield 40 mg, 99% e.e. (first eluting peak at 14.4 mins)

Peak 2 Yield 22 mg, 98.8% e.e. (second eluting peak at 21.6 mins)

Preparation 44: 3-[6-(4-Cyano-phenyl)-pyridin-3-yloxymethyl]-1-(2-methoxy-benzoyl)-pyrrolidine-3-carboxylic acid ethyl ester (±)

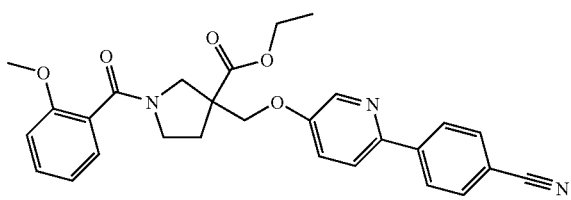

The title compound was prepared according to the method described for Preparation 29 using 4-(5-hydroxy-pyridin-2-yl)-benzonitrile (Preparation 22) and 3-iodomethyl-1-(2-methoxy-benzoyl)-pyrrolidine-3-carboxylic acid ethyl ester (Preparation 15) to afford the racemate as a white solid (149 mg, 85.2%)

The enantiomers were separated using a Chiralpak IA 55:45:0.1 heptane:IPA:DEA.

Peak 1 Yield 34 mg, 99.5% e.e. (first eluting peak at 13.04 mins)

Peak 2 Yield 36.2 mg, 99.5% e.e. (second eluting peak at 22.77 mins)

Preparation 45: 3-[4-(5-Fluoro-pyrimidin-2-yl)-phenoxymethyl]-1-(2-methoxy-benzoyl)-pyrrolidine-3-carboxylic acid ethyl ester (±)

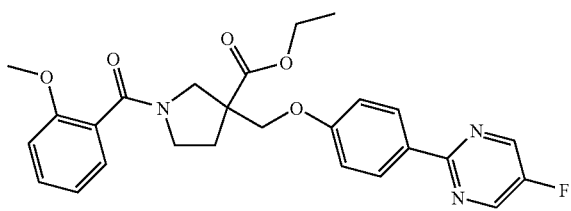

The title compound was prepared according to the method described for Preparation 29 using 4-(5-fluoro-pyrimidin-2-yl)-phenol (Preparation 20) and 3-iodomethyl-1-(2-methoxy-benzoyl)-pyrrolidine-3-carboxylic acid ethyl ester (Preparation 15) to afford the racemate as a white solid (85 mg, 49%)

The enantiomers were separated using a Chiralpak IA 70:30:0.1 heptane:IPA:DEA.

Peak 1 Yield 34 mg, 96.4% e.e. (first eluting peak at 9.13 mins)

Peak 2 Yield 35 mg, 99.5% e.e. (second eluting peak at 12.04 mins)

Preparation 46: 3-[4-(5-Cyano-pyrimidin-2-yl)-phenoxymethyl]-1-(2-methoxy-benzoyl)-pyrrolidine-3-carboxylic acid ethyl ester (±)

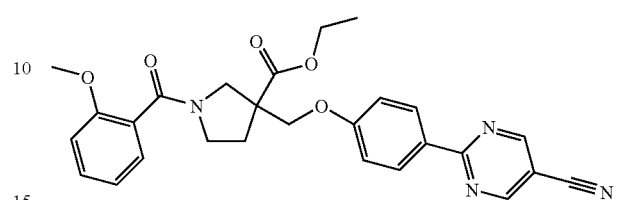

The title compound was prepared according to the method described for Preparation 29 using 2-(4-hydroxy-phenyl)-pyrimidine-5-carbonitrile and 3-iodomethyl-1-(2-methoxy-benzoyl)-pyrrolidine-3-carboxylic acid ethyl ester (Preparation 15) to afford the racemate as a white solid (53 mg, 30%)

The enantiomers were separated using a Chiralpak IA 55:45:0.1 heptane:IPA:DEA.

Peak 1 Yield 19 mg, 96.4% e.e. (first eluting peak at 9.13 mins)

Peak 2 Yield 4 mg, 99.5% e.e. (first eluting peak at 12.04 mins)

Preparation 47: 3-(4'-Cyano-biphenyl-4-yloxymethyl)-1-(2-methoxy-benzoyl)-pyrrolidine-3-carboxylic acid ethyl ester (±)

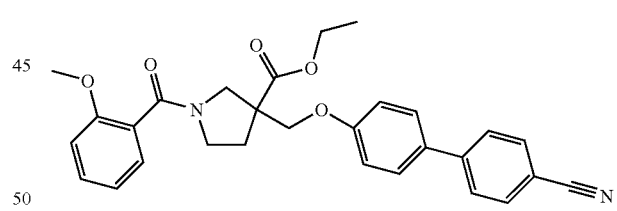

The title compound was prepared according to the method described for Preparation 29 using 4'-hydroxy-4-biphenyl carbonitrile and 3-iodomethyl-1-(2-methoxy-benzoyl)-pyrrolidine-3-carboxylic acid ethyl ester (Preparation 15) to afford the racemate as a white solid (157 mg, 66%)

The enantiomers were separated using a Chiralpak IB 55:45 heptane:IPA.

Peak 1 Yield 39 mg, 98.5% e.e. (first eluting peak at 13.5 mins)

Peak 2 Yield 42 mg, 96.8% e.e. (second eluting peak at 17.10 mins)

Preparation 48: 3-(4'-Fluoro-biphenyl-4-yloxymethyl)-1-(2-methoxy-benzoyl)-pyrrolidine-3-carboxylic acid ethyl ester (±)

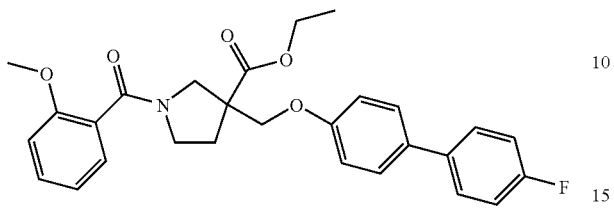

The title compound was prepared according to the method described for Preparation 29 using 4'-fluoro-biphenyl-4-ol and 3-iodomethyl-1-(2-methoxy-benzoyl)-pyrrolidine-3-carboxylic acid ethyl ester (Preparation 15) to afford the racemate as a white solid (178 mg, 76%)

The enantiomers were separated using a Chiralpak IB 55:45 heptane:IPA.

Peak 1 Yield 46 mg, 99.5% e.e. (first eluting peak at 10.10 mins)

Peak 2 Yield 42 mg, 98.4% e.e. (second eluting peak at 12.70 mins)

Preparation 49: 3-[6-(4-Chloro-phenyl)-pyridin-3-yloxymethyl]-1-(2-methoxy-benzoyl)-pyrrolidine-3-carboxylic acid ethyl ester (±)

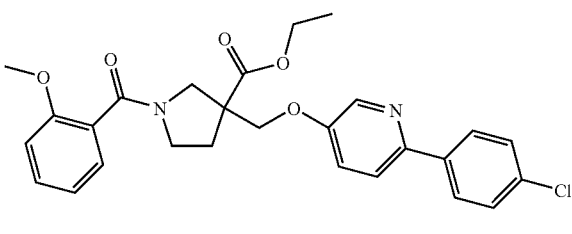

The title compound was prepared according to the method described for Preparation 29 using 6-(4-chloro-phenyl)-pyridin-3-ol (Preparation 23) and 3-iodomethyl-1-(2-methoxy-benzoyl)-pyrrolidine-3-carboxylic acid ethyl ester (Preparation 15) to afford the racemate as a white solid (116 mg, 47.7%)

The enantiomers were separated using a Chiralpak IB 55:45 heptane:IPA.

Peak 1 Yield 11 mg, 99.5% e.e. (first eluting peak at 12.2 mins)

Peak 2 Yield 7 mg, 99.5% e.e. (second eluting peak at 16.9 mins)

Preparation 50: 3-[4-(5-Chloro-pyridin-2-yl)-phenoxymethyl]-1-(2-methoxy-benzoyl)-pyrrolidine-3-carboxylic acid ethyl ester (±)

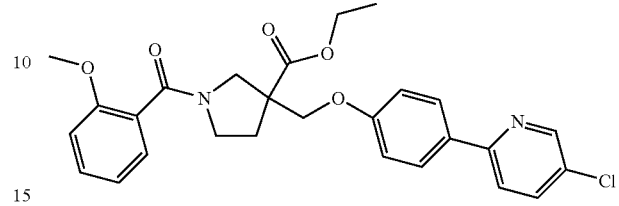

The title compound was prepared according to the method described for Preparation 29 using 4-(5-chloro-pyridin-2-yl)-phenol (Preparation 17) and 3-iodomethyl-1-(2-methoxy-benzoyl)-pyrrolidine-3-carboxylic acid ethyl ester (Preparation 15) to afford the racemate as a white solid (133 mg, 54.7%)

The enantiomers were separated using a Chiralpak IB 55:45 heptane:IPA.

Peak 1 Yield 39 mg, 97.7% e.e. (first eluting peak at 10.3 mins)

Peak 2 Yield 36 mg, 98.2% e.e. (second eluting peak at 12.9 mins)

Preparation 51: 3-[4-(5-Chloro-pyrimidin-2-yl)-phenoxymethyl]-1-(2-methoxy-benzoyl)-pyrrolidine-3-carboxylic acid ethyl ester (±)

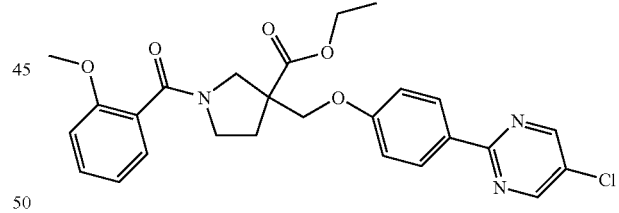

The title compound was prepared according to the method described for Preparation 29 using 4-(5-chloro-pyrimidin-2-yl)-phenol (Preparation 19) and 3-iodomethyl-1-(2-methoxy-benzoyl)-pyrrolidine-3-carboxylic acid ethyl ester (Preparation 15) to afford the racemate as a white solid (160 mg, 65.7%)

The enantiomers were separated using a Chiralpak IB 55:45 heptane:IPA.

Peak 1 Yield 56 mg, 97.6% e.e. (first eluting peak at 10.01 mins)

Peak 2 Yield 54 mg, 98.8% e.e. (second eluting peak at 13.07 mins)

Preparation 52: 3-[6-(4-Fluoro-phenyl)-pyridin-3-yloxymethyl]-1-(2-methoxy-benzoyl)-pyrrolidine-3-carboxylic acid ethyl ester (±)

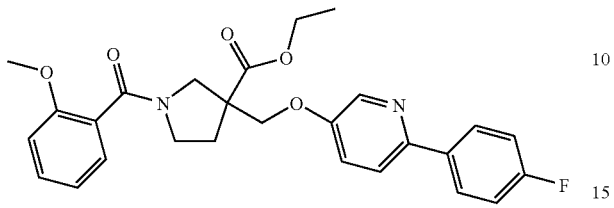

The title compound was prepared according to the method described for Preparation 29 using 6-(4-fluoro-phenyl)-pyridin-3-ol (Preparation 21) and 3-iodomethyl-1-(2-methoxy-benzoyl)-pyrrolidine-3-carboxylic acid ethyl ester (Preparation 15) to afford the racemate as a white solid (127 mg, 73.7%)

The enantiomers were separated using a Chiralpak AD-H 55:45 heptane:IPA.

Peak 1 Yield 57 mg, 96.9% e.e. (first eluting peak at 12.25 mins)

Peak 2 Yield 50 mg, 99.3% e.e. (second eluting peak at 21.4 mins)

Preparation 53: 3-[2-(4-Chloro-phenyl)-pyrimidin-5-yloxymethyl]-1-(2-methoxy-benzoyl)-pyrrolidine-3-carboxylic acid ethyl ester (±)

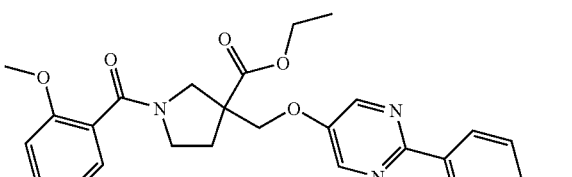

The title compound was prepared according to the method described for Preparation 29 using 2-(4-chloro-phenyl)-pyrimidin-5-ol (Preparation 27) and 3-iodomethyl-1-(2-methoxy-benzoyl)-pyrrolidine-3-carboxylic acid ethyl ester (Preparation 15) to afford the racemate as a white solid (110 mg, 45.2%)

The enantiomers were separated using a Chiralpak IB 55:45 heptane:IPA.

Peak 1 Yield 24 mg, 98.7% e.e. (first eluting peak at 12.0 mins)

Peak 2 Yield 24 mg, 99% e.e. (second eluting peak at 16.9 mins)

Preparation 54: 1-(2-Ethoxy-benzoyl)-3-(4'-fluoro-biphenyl-4-yloxymethyl)-pyrrolidine (±)

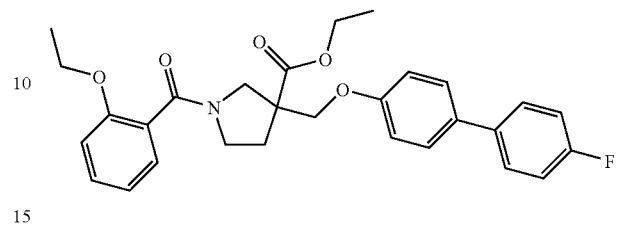

The title compound was prepared according to the method described for Preparation 29 using 4'-fluoro-biphenyl-4-ol and 1-(2-ethoxy-benzoyl)-3-iodomethyl-pyrrolidine-3-carboxylic acid ethyl ester (Preparation 16) to afford the racemate as a white solid (191 mg, 70%)

The enantiomers were separated using a Chiralpak OD-H 55:45 heptane:IPA.

Peak 1 Yield 65 mg, 99.5% e.e. (first eluting peak at 6.8 mins)

Peak 2 Yield 60 mg, 99.3% e.e. (second eluting peak at 8.5 mins)

Preparation 55: 3-[4-(5-Chloro-pyrimidin-2-yl)-phenoxymethyl]-1-(2-ethoxy-benzoyl)-pyrrolidine-3-carboxylic acid ethyl ester (±)

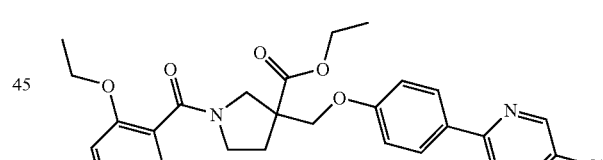

The title compound was prepared according to the method described for Preparation 29 using 4-(5-chloro-pyrimidin-2-yl)-phenol (Preparation 19) and 1-(2-ethoxy-benzoyl)-3-iodomethyl-pyrrolidine-3-carboxylic acid ethyl ester (Preparation 16) to afford the racemate as a white solid (103 mg, 36.3%)

The enantiomers were separated using a Chiralpak IB 55:45 heptane:IPA.

Peak 1 Yield 20 mg, 98.7% e.e. (first eluting peak at 8.10 mins)

Peak 2 Yield 15 mg, 99% e.e. (second eluting peak at 10.8 mins)

Preparation 56: 3-[2-(4-Chloro-phenyl)-pyrimidin-5-yloxymethyl]-1-(2-ethoxy-benzoyl)-pyrrolidine-3-carboxylic acid ethyl ester (±)

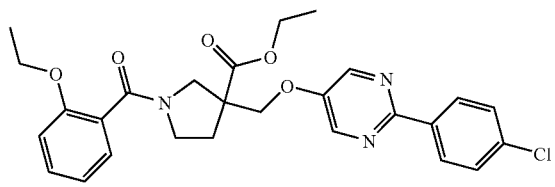

The title compound was prepared according to the method described for Preparation 29 using 2-(4-chloro-phenyl)-pyrimidin-5-ol (Preparation 27) and 1-(2-ethoxy-benzoyl)-3-iodomethyl-pyrrolidine-3-carboxylic acid ethyl ester (Preparation 16) to afford the racemate as a white solid (238 mg, 83.9%)

The enantiomers were separated using a Chiralpak IB 55:45 heptane:IPA.

Peak 1 Yield 45 mg, 98.7% e.e. (first eluting peak at 9.60 mins)

Peak 2 Yield 48 mg, 99.1% e.e. (second eluting peak at 13.7 mins)

Preparation 57: 3-[5-(4-Chloro-phenyl)-pyrazin-2-yloxymethyl]-1-(4-fluoro-benzoyl)-pyrrolidine-3-carboxylic acid ethyl ester (±)

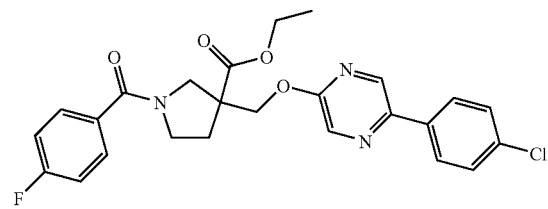

The title compound was prepared according to the method described for Preparation 29 using 5-(4-chloro-phenyl)-pyrazin-2-ol (Preparation 25) and 1-(4-fluoro-benzoyl)-3-iodomethyl-pyrrolidine-3-carboxylic acid ethyl ester (Preparation 12) to afford the racemate as a white solid (73 mg, 20%)

The enantiomers were separated using a Chiralpak IB 55:45 heptane:IPA.

Peak 1 Yield 20 mg, 97.8% e.e. (first eluting peak at 9.09 mins)

Peak 2 Yield 22 mg, 97.5% e.e. (second eluting peak at 11.1 mins)

Preparation 58: 1-(4-Chloro-benzoyl)-3-[5-(4-chloro-phenyl)-pyrazin-2-yloxymethyl]-pyrrolidine-3-carboxylic acid ethyl ester (±)

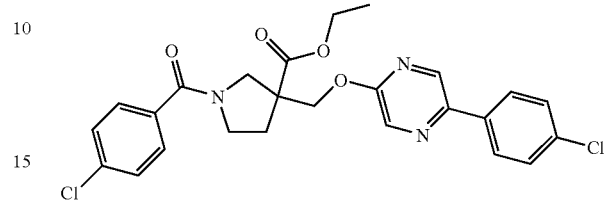

The title compound was prepared according to the method described for Preparation 29 using 5-(4-chloro-phenyl)-pyrazin-2-ol (Preparation 25) and 1-(4-chloro-benzoyl)-3-iodomethyl-pyrrolidine-3-carboxylic acid ethyl ester (Preparation 13) to afford the racemate as a pale yellow solid (42 mg, 20%)

The enantiomers were separated using a Chiralpak IA 55:45 heptane:IPA.

Peak 1 Yield 13.1 mg, 99% e.e. (first eluting peak at 13.10 mins)

Peak 2 Yield 19.3 mg, 99.2% e.e. (second eluting peak at 19.29 mins)

Preparation 59: 3-[5-(4-Chloro-phenyl)-pyrazin-2-yloxymethyl]-1-(4-methoxy-benzoyl)-pyrrolidine-3-carboxylic acid ethyl ester (±)

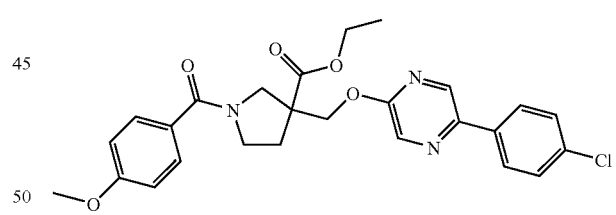

The title compound was prepared according to the method described for Preparation 29 using 5-(4-chloro-phenyl)-pyrazin-2-ol (Preparation 25) and 3-iodomethyl-1-(4-methoxy-benzoyl)-pyrrolidine-3-carboxylic acid ethyl ester (Preparation 14) to afford the racemate as a white solid (44 mg, 22%)

The enantiomers were separated using a Chiralpak IA 55:45 heptane:IPA.

Peak 1 Yield 14 mg, 95% e.e. (first eluting peak at 15.40 mins)

Peak 2 Yield 21 mg, 95% e.e. (second eluting peak at 18.60 mins)

Preparation 60: 3-[5-(4-Chloro-phenyl)-pyrazin-2-yloxymethyl]-1-(2-methoxy-benzoyl)-pyrrolidine-3-carboxylic acid ethyl ester (±)

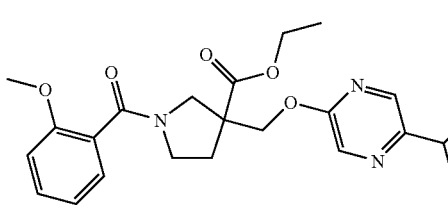

The title compound was prepared according to the method described for Preparation 29 using 5-(4-chloro-phenyl)-pyrazin-2-ol (Preparation 25) and 3-iodomethyl-1-(2-methoxy-benzoyl)-pyrrolidine-3-carboxylic acid ethyl ester (Preparation 15) to afford the racemate as a white solid (45 mg, 18%)

The enantiomers were separated using a Chiralpak IA 55:45 heptane:IPA.

Peak 1 Yield 13 mg, 95% e.e. (first eluting peak at 10.30 mins)

Peak 2 Yield 6 mg, 99% e.e. (second eluting peak at 13.0 mins)

Preparation 61: 3-[5-(4-Chloro-phenyl)-pyrazin-2-yloxymethyl]-1-(2-ethoxy-benzoyl)-pyrrolidine-3-carboxylic acid ethyl ester (±)

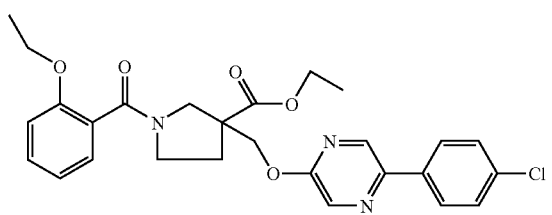

The title compound was prepared according to the method described for Preparation 29 using 5-(4-chloro-phenyl)-pyrazin-2-ol (Preparation 25) and 1-(2-ethoxy-benzoyl)-3-iodomethyl-pyrrolidine-3-carboxylic acid ethyl ester (Preparation 16) to afford the racemate as a white solid (86 mg, 30%)

The enantiomers were separated using a Chiralpak IA 55:45 heptane:IPA.

Peak 1 Yield 29.2 mg, 99.7% e.e. (first eluting peak at 11.70 mins)

Peak 2 Yield 98 mg, 98.9% e.e. (second eluting peak at 14.6 mins)

Preparation 62: 1-(4-Fluoro-benzoyl)-3-(4'-fluoro-biphenyl-4-yloxymethyl)-pyrrolidine-3-carboxylic acid ethyl ester (±)

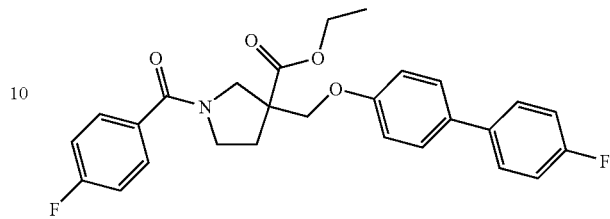

The title compound was prepared according to the method described for Preparation 29 using 4'-fluoro-biphenyl-4-ol and 1-(4-fluoro-benzoyl)-3-iodomethyl-pyrrolidine-3-carboxylic acid ethyl ester (Preparation 12) to afford the racemate as a white solid (150 mg, 73%)

ES m/z 467 [MH]+

Preparation 63: 3-(2,3-Difluoro-phenoxymethyl)-1-(4-fluoro-benzoyl)-pyrrolidine-3-carboxylic acid ethyl ester (±)

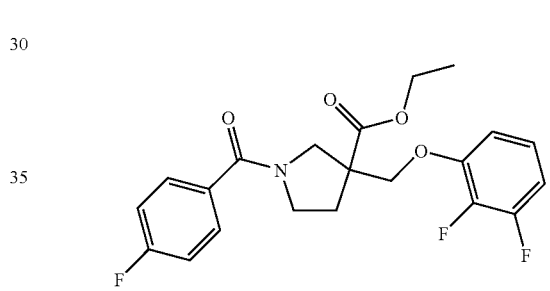

The title compound was prepared according to the method described for Preparation using 2,3-difluoro-phenol and 1-(4-fluoro-benzoyl)-3-iodomethyl-pyrrolidine-3-carboxylic acid ethyl ester (Preparation 12) to afford the racemate as a white solid (167 mg, 68%) ES m/z 408 [MH]+

Preparation 64: 3-(3-Chloro-4-fluoro-phenoxymethyl)-1-(4-fluoro-benzoyl)-pyrrolidine-3-carboxylic acid ethyl ester (±)

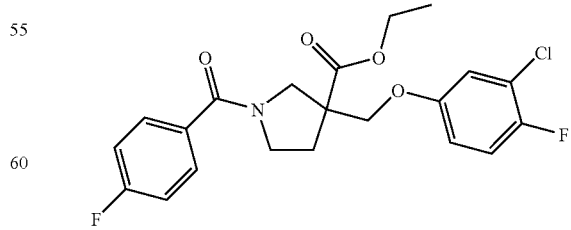

The title compound was prepared according to the method described for Preparation 29 using 3-chloro-4-fluoro-phenol and 1-(4-fluoro-benzoyl)-3-iodomethyl-pyrrolidine-3-carboxylic acid ethyl ester (Preparation 12) to afford the racemate as a white solid (153 mg, 69%) ES m/z 424 [MH]$^+$ Preparation 65: 3-(4'-Fluoro-biphenyl-4-yloxymethyl)-pyrrolidine-3-carboxylic acid ethyl ester (±)

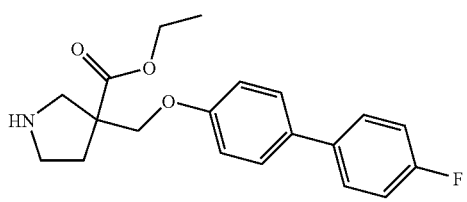

6M HCl aqueous solution (65 mL) was added to racemic 1-(4-fluoro-benzoyl)-3-(4'-fluoro-biphenyl-4-yloxymethyl)-pyrrolidine-3-carboxylic acid ethyl ester (see Preparation 62) (6.3 g, 13.5 mmol) and the resulting mixture refluxed for 18 hours. The reaction mixture was evaporated to dryness. The resulting crystalline solid was dissolved in ethanol (25 mL), cooled to 0° C. and thionyl chloride added (1.46 mL, 19.81 mmol). The mixture was then heated at reflux for 16 hours. The mixture was partitioned between saturated sodium hydrogen carbonate solution (100 mL) and ethyl acetate (100 mL). The organic layer was separated, washed with water (100 mL), dried over magnesium sulphate and concentrated under reduced pressure. The residue was purified by column chromatography on silica gel, eluting with 2% methanol in dichloromethane to afford the title compound as a brown oil (2.5 g, 52%).

1H NMR (400 MHz, DMSO d-6) δ ppm 1.14 (t, 3H) 1.72-1.79 (m, 1H) 2.09-2.15 (m, 1H) 2.76-2.93 (m, 3H) 3.09 (d, 1H) 4.07-4.16 (m, 4H) 7.00 (d, 2H) 7.24 (t, 2H) 7.56 (d, 2H) 7.61-7.65 (m, 2H).

Preparation 66: 3-(4'-Fluoro-biphenyl-4-yloxymethyl)-pyrrolidine-1,3-dicarboxylic acid 3-ethyl ester 1-(2-methoxy-phenyl) ester (±)

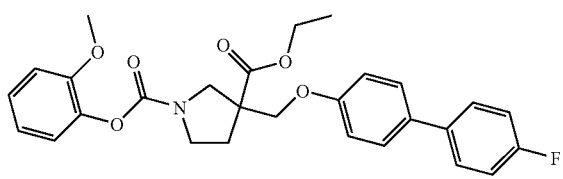

Sodium hydrogen carbonate (244 mg, 2.9 mmol) was added to a stirred solution of 3-(4'-fluoro-biphenyl-4-yloxymethyl)-pyrrolidine-3-carboxylic acid ethyl ester (see Preparation 65) (200 mg, 0.58 mmol) in dichloromethane (10 mL) and the resulting mixture cooled to 0° C. 2-Methoxy phenyl chloroformate (0.09 mL, 0.64 mmol) was added and the reaction mixture stirred at room temperature for 16 hours. The mixture was partitioned between water (25 mL) and dichloromethane (25 mL). The organic layer was separated, washed brine (25 mL), dried over magnesium sulphate and concentrated under reduced pressure. The residue was purified by column chromatography on silica gel, eluting with 15% ethyl acetate in hexane to afford the title compound as a white solid (210 mg, 74%).

1H NMR (400 MHz, DMSO d-6) δ ppm 1.18 (t, 3H) 2.16-2.21 (m, 1H) 2.32-2.40 (m, 1H) 3.44-4.34 (m, 11H) 6.92 (t, 1H) 7.03-7.10 (m, 4H) 7.19 (t, 1H) 7.25 (t, 2H) 7.58 (d, 2H) 7.63-7.66 (m, 2H).

The enantiomers were separated using a Chiralpak IB 55:45 heptane:IPA.

Peak 1 Yield 50 mg, 97.6% e.e. (first eluting peak at 9.629 mins)

Peak 2 Yield 50 mg, 97.8% e.e. (second eluting peak at 15.445 mins)

Preparation 67: 3-(4'-Fluoro-biphenyl-4-yloxymethyl)-pyrrolidine-1,3-dicarboxylic acid 3-ethyl ester 1-p-tolyl ester (±)

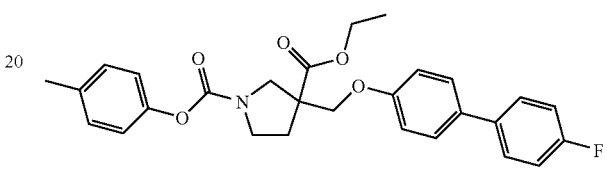

The title compound was prepared according to the method described for Preparation 66 using 4-methyl phenyl chloroformate and 3-(4'-fluoro-biphenyl-4-yloxymethyl)-pyrrolidine-3-carboxylic acid ethyl ester (Preparation 65) to afford the racemate as a white solid (215 mg, 70%).

1H NMR (400 MHz, DMSO d-6) δ ppm 1.17 (t, 3H) 2.12-2.36 (m, 2H) 2.28 (s, 3H) 3.44-4.34 (m, 8H) 6.99-7.04 (m, 4H) 7.16 (d, 2H) 7.24 (t, 2H) 7.56-7.65 (m, 4H).

The enantiomers were separated using a Chiralpak IB 55:45 heptane:IPA.

Peak 1 66 mg, Yield 95.6% e.e. (first eluting peak at 7.300 mins)

Peak 2 65 mg, Yield 98.6% e.e. (second eluting peak at 11.289 mins)

Preparation 68: 3-(4'-Fluoro-biphenyl-4-yloxymethyl)-pyrrolidine-1,3-dicarboxylic acid 3-ethyl ester 1-p-tolyl ester (±)

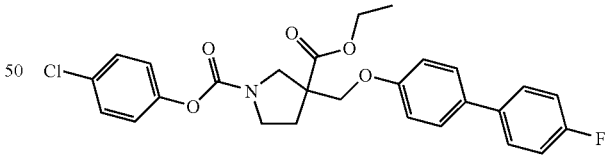

The title compound was prepared according to the method described for Preparation 66 using 4-chloro phenyl chloroformate and 3-(4'-fluoro-biphenyl-4-yloxymethyl)-pyrrolidine-3-carboxylic acid ethyl ester (Preparation 65) to afford the racemate as a white solid (222 mg, 77%)

1H NMR (400 MHz, DMSO d-6) δ ppm 1.17 (t, 3H) 2.13-2.38 (m, 2H), 3.44-4.34 (m, 8H), 7.03 (d, 2H, J=8.4 Hz), 7.17-7.27 (m, 4H), 7.44 (d, 2H, J=8.4 Hz), 7.57-7.66 (m, 4H).

The enantiomers were separated using a Chiralpak IB 55:45 heptane:IPA.

Peak 1 Yield 72 mg, 89.8% e.e. (first eluting peak at 6.812 mins)

Peak 2 Yield 67 mg, 97.2% e.e. (second eluting peak at 8.654 mins)

Preparation 69: 3-(4'-Fluoro-biphenyl-4-yloxymethyl)-pyrrolidine-1,3-dicarboxylic acid 3-ethyl ester 1-(4-fluoro-phenyl)ester (±)

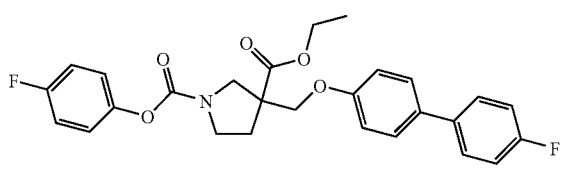

The title compound was prepared according to the method described for Preparation 66 using 4-fluoro phenyl chloroformate and 3-(4'-fluoro-biphenyl-4-yloxymethyl)-pyrrolidine-3-carboxylic acid ethyl ester (Preparation 65) to afford the racemate as a white solid (180 mg, 58%)

1H NMR (400 MHz, DMSO d-6) δ ppm 1.17 (t, 3H) 2.12-2.38 (m, 2H) 3.44-4.34 (m, 8H) 7.03 (d, 2H, J=8.4 Hz) 7.19-7.27 (m, 6H) 7.57 (d, 2H, J=8.4 Hz) 7.62-7.66 (m, 2H). The enantiomers were separated using a Chiralpak IB 55:45 heptane:IPA.

Peak 1 Yield 48 mg, 98.1% e.e. (first eluting peak at 6.7 mins)

Peak 2 Yield 45 mg, 78.5% e.e. (second eluting peak at 8.3 mins)

Preparation 70: 3-(4'-Fluoro-biphenyl-4-yloxymethyl)-pyrrolidine-1,3-dicarboxylic acid 3-ethyl ester 1-(4-methoxy-phenyl)ester (±)

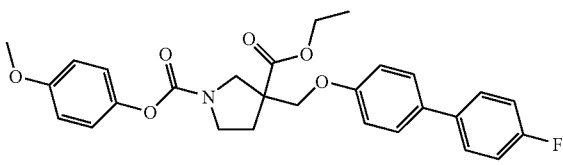

The title compound was prepared according to the method described for Preparation 66 using 4-methoxy phenyl chloroformate and 3-(4'-fluoro-biphenyl-4-yloxymethyl)-pyrrolidine-3-carboxylic acid ethyl ester (Preparation 65) to afford the racemate as a white solid (185 mg, 59%)

1H NMR (400 MHz, DMSO d-6) δ ppm 1.17 (t, 3H) 2.15-2.35 (m, 2H) 3.42-3.68 (m, 3H) 3.73 (s, 3H) 3.84-4.34 (m, 5H) 6.91 (d, 2H) 7.03-7.04 (m, 4H) 7.25 (t, 2H) 7.58 (d, 2H) 7.64-7.66 (m, 2H).

The enantiomers were separated using a Chiralpak IB 55:45 heptane:IPA.

Peak 1 Yield 67 mg, 97.4% e.e. (first eluting peak at 9.7 mins)

Peak 2 Yield 68 mg, 98.7% e.e. (second eluting peak at 14.9 mins)

Preparation 71: 1-(2-Chloro-phenylcarbamoyl)-3-(4'-fluoro-biphenyl-4-yloxymethyl)-pyrrolidine-3-carboxylic acid ethyl ester (±)

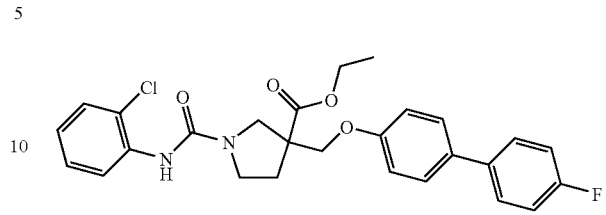

Triethylamine (0.23 mL, 1.67 mmol) was added to a stirred solution of 3-(4'-fluoro-biphenyl-4-yloxymethyl)-pyrrolidine-3-carboxylic acid ethyl ester (see Preparation 65) (185 mg, 0.54 mmol) in dichloromethane (10 mL) and the resulting mixture cooled to 0° C. 2-Chloro phenyl isocyanate (0.065 mL, 0.54 mmol) was added and the reaction mixture stirred at room temperature for 16 hours. The mixture was partitioned between water (25 mL) and dichloromethane (25 mL). The organic layer was separated, washed brine (25 mL), dried over magnesium sulphate and concentrated under reduced pressure. The residue was purified by column chromatography on silica gel, eluting with 25% ethyl acetate in hexane to afford the title compound as a colourless liquid (245 mg, 91%).

1H NMR (400 MHz, DMSO d-6) δ ppm 1.16 (t, 3H) 2.12-2.21 (m, 1H) 2.32-2.40 (m, 1H) 3.49-3.60 (m, 3H) 3.93 (d, 1H) 4.13-4.30 (m, 4H) 7.03 (d, 2H) 7.11 (t, 1H) 7.22-7.29 (m, 3H) 7.44 (d, 1H) 7.57 (d, 2H) 7.62-7.66 (m, 3H) 7.80 (br, 1H).

The enantiomers were separated using a Chiralpak IA 100% MeOH

Peak 1 Yield 57 mg, 75.2% e.e. (first eluting peak at 7.53 mins)

Peak 2 Yield 40 mg, 94.8% e.e. (second eluting peak at 9.39 mins)

Preparation 72: 3-(4'-Fluoro-biphenyl-4-yloxymethyl)-1-(3-methoxy-phenylcarbamoyl)pyrrolidine-3-carboxylic acid ethyl ester (±)

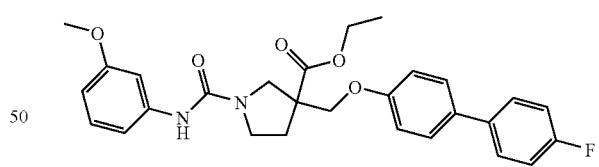

The title compound was prepared according to the method described for Preparation using 3-methoxy phenyl isocyanate and 3-(4'-fluoro-biphenyl-4-yloxymethyl)-pyrrolidine-3-carboxylic acid ethyl ester (Preparation 65) to afford a racemate as a colourless liquid (230 mg, 80%)

1H NMR (400 MHz, DMSO d-6) δ ppm 1.16 (t, 3H) 2.10-2.32 (m, 2H) 3.45-3.58 (m, 3H) 3.69 (s, 3H) 3.92 (d, 1H) 4.16 (q, 2H) 4.21 (d, 1H) 4.28 (d, 1H) 6.49 (br, 1H) 7.03 (d, 2H) 7.10-7.27 (m, 5H) 7.57 (d, 2H) 7.62-7.65 (m, 2H) 8.23 (brs, 1H).

The enantiomers were separated using a Chiralpak OD-H 100% MeOH

Peak 1 Yield 64 mg, 99.5% e.e. (first eluting peak at 9.51 mins)

Peak 2 Yield 66 mg, 99.5% e.e. (second eluting peak at 12.52 mins)

Preparation 73: 1-(4-Chloro-phenylcarbamoyl)-3-(4'-fluoro-biphenyl-4-yloxymethyl)-pyrrolidine-3-carboxylic acid ethyl ester (±)

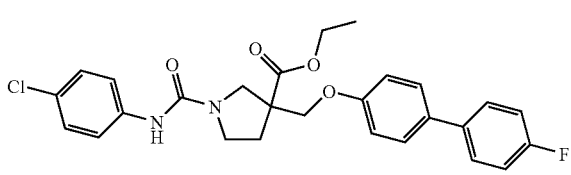

The title compound was prepared according to the method described for Preparation using 4-chloro phenyl isocyanate and 3-(4'-fluoro-biphenyl-4-yloxymethyl)-pyrrolidine-3-carboxylic acid ethyl ester (Preparation 65) to afford the racemate as a white solid (220 mg, 76%)

1H NMR (400 MHz, DMSO d-6) δ ppm 1.16 (t, 3H) 2.11-2.32 (m, 2H) 3.48-3.58 (m, 3H) 3.92 (d, 1H) 4.14-4.30 (m, 4H) 7.02 (d, 2H) 7.22-7.27 (m, 4H) 7.54-7.65 (m, 6H) 8.40 (brs, 1H).

The enantiomers were separated using a Chiralpak IC 55:45 heptane:IPA.

Peak 1 Yield 53 mg, 98.4% e.e. (first eluting peak at 6.9 mins)

Peak 2 Yield 47 mg, 97.6% e.e. (second eluting peak at 8.6 mins)

Preparation 74: 3-(4'-Fluoro-biphenyl-4-yloxymethyl)-1-(4-methoxy-phenylcarbamoyl)-pyrrolidine-3-carboxylic acid ethyl ester (±)

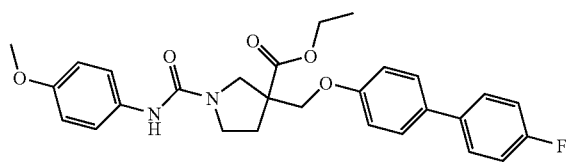

The title compound was prepared according to the method described for Preparation 71 using 4-methoxy phenyl isocyanate and 3-(4'-fluoro-biphenyl-4-yloxymethyl)-pyrrolidine-3-carboxylic acid ethyl ester (Preparation 65) to afford the racemate as a yellow liquid (78, mg, 88%)

1H NMR (400 MHz, DMSO d-6) δ ppm 1.16 (t, 3H) 2.10-2.32 (m, 2H) 3.45-3.58 (m, 3H) 3.87 (s, 3H) 4.12-4.29 (m, 4H) 6.87 (m, 1H) 6.95-7.04 (m, 4H) 7.22-7.26 (m, 2H) 7.57 (d, 2H) 7.62-7.65 (m, 2H) 7.77-7.81 (m, 1H) 8.31 (brs, 1H).

The enantiomers were separated using a Chiralpak OD-H 100% MeOH

Peak 1 Yield 63 mg, 100% e.e. (first eluting peak at 5.5 mins)

Peak 2 Yield 57 mg, 100% e.e. (second eluting peak at 7.5 mins)

Preparation 75: 3-(4'-Fluoro-biphenyl-4-yloxymethyl)-1-(2-fluoro-phenylcarbamoyl)-pyrrolidine-3-carboxylic acid ethyl ester (±)

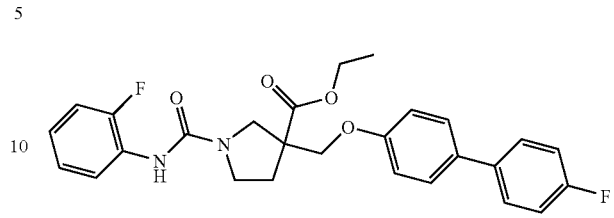

The title compound was prepared according to the method described for Preparation 71 using 2-fluoro phenyl isocyanate and 3-(4'-fluoro-biphenyl-4-yloxymethyl)-pyrrolidine-3-carboxylic acid ethyl ester (Preparation 65) to afford the racemate as a colourless liquid (230 mg, 82%)

1H NMR (400 MHz, DMSO d-6) δ ppm 1.16 (t, 3H) 2.10-2.32 (m, 2H) 3.40-4.28 (m, 8H) 7.03 (d, 2H) 7.09-7.26 (m, 5H) 7.50-7.65 (m, 5H).

The enantiomers were separated using a Chiralpak IB 55:45 heptane:IPA

Peak 1 Yield 64 mg, 99.4% e.e. (first eluting peak at 7.2 mins)

Peak 2 Yield 46 mg, 97.1% e.e. (second eluting peak at 9.1 mins)

Preparation 76: 1-Cyclopropanecarbonyl-3-(4'-fluoro-biphenyl-4-yloxymethyl)-pyrrolidine-3-carboxylic acid ethyl ester (±)

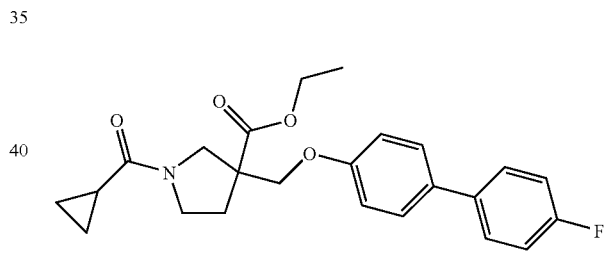

Triethylamine (0.37 mL, 2.7 mmol) was added to a stirred solution of 3-(4'-fluoro-biphenyl-4-yloxymethyl)-pyrrolidine-3-carboxylic acid ethyl ester (see Preparation 65) (300 mg, 0.87 mmol) in dichloromethane (10 mL) and the resulting mixture cooled to 0° C. Cyclopropanecarbonyl chloride (0.08 mL, 0.87 mmol) was added and the reaction mixture stirred at room temperature for 16 hours. The mixture was partitioned between water (50 mL) and dichloromethane (50 mL). The organic layer was separated, washed brine (50 mL), dried over magnesium sulphate and concentrated under reduced pressure. The residue was purified by column chromatography on silica gel, eluting with 15% ethyl acetate in hexane to afford the title compound as a pale yellow solid (305 mg, 85%).

1H NMR (400 MHz, DMSO d-6) δ ppm 0.72 (m, 4H) 0.85 (m, 1H) 1.15 (t, 3H) 1.75-1.85 (m, 1H) 2.15-2.30 (m, 1H) 3.48-4.24 (m, 8H) 7.00-7.03 (m, 2H) 7.24 (t, 2H) 7.56-7.65 (m, 4H).

The enantiomers of 108 mg of title compound were separated using a Chiralcel OJ-H 50:50 MeOH:EtOH.

Peak 1 9 mg, >99.5% e.e. (first eluting peak at 10.5 mins)

Peak 2 12 mg, >99.5% e.e. (second eluting peak at 13.7 mins)

Preparation 77: 1-Cyclobutanecarbonyl-3-(4'-fluoro-biphenyl-4-yloxymethyl)-pyrrolidine-3-carboxylic acid ethyl ester (±)

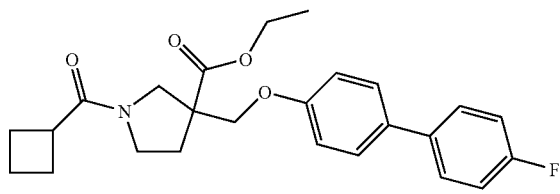

The title compound was prepared according to the method described for Preparation using cyclobutanecarbonyl chloride and 3-(4'-fluoro-biphenyl-4-yloxymethyl)-pyrrolidine-3-carboxylic acid ethyl ester (Preparation 65) to afford the racemate as a colourless oil (105 mg, 85%)

1H NMR (400 MHz, DMSO d-6) δ ppm 1.15 (t, 3H) 1.66-2.32 (m, 8H) 3.21-3.50 (m, 4H) 3.77-3.81 (m, 1H) 4.12-4.24 (m, 4H) 7.01 (d, 2H), 7.24 (t, 2H) 7.56 (d, 2H), 7.62-7.65 (m, 2H).

The enantiomers were separated using a Chiralcel OJ-H 50:50 MeOH:EtOH.

Peak 1 23 mg, >99.5% e.e. (first eluting peak at 10.6 mins)

Peak 2 70 mg, >99.5% e.e. (second eluting peak at 14.3 mins)

Preparation 78: 1-Cyclopentanecarbonyl-3-(4'-fluoro-biphenyl-4-yloxymethyl)pyrrolidine-3-carboxylic acid ethyl ester (±)

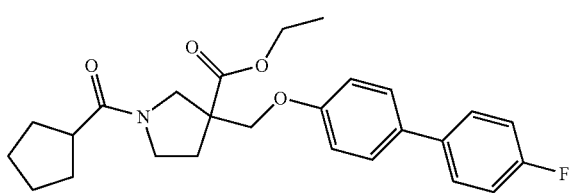

The title compound was prepared according to the method described for Preparation 76 using cyclopentanecarbonyl chloride and 3-(4'-fluoro-biphenyl-4-yloxymethyl)-pyrrolidine-3-carboxylic acid ethyl ester (Preparation 65) to afford the racemate as a white solid (120 mg, 94%)

1H NMR (400 MHz, DMSO d-6) δ ppm 1.15 (t, 3H) 1.50-1.78 (m, 8H) 2.05-2.25 (m, 2H) 2.82 (m, 1H) 3.44-4.27 (m, 8H) 7.01 (d, 2H) 7.25 (t, 2H) 7.57 (d, 2H) 7.62-7.65 (m, 2H).

The enantiomers were separated using a Chiralcel OJ-H 50:50 MeOH:EtOH.

Peak 1 61 mg, >99.5% e.e. (first eluting peak at 10.5 mins)

Peak 2 31 mg, >99.5% e.e. (second eluting peak at 14.9 mins)

The invention claimed is:

1. A compound of formula (I):

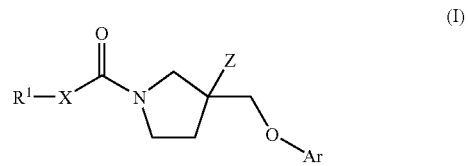

wherein:
$R^1$ is a phenyl group optionally substituted by one or two substituents independently selected from F, Cl, Br, CN, $C_{1-4}$ alkyl, $C_{1-4}$ alkylthio and $C_{1-4}$ alkoxy, fluoro-$C_{1-6}$ alkyl and fluoro-$C_{1-6}$ alkoxy, or a $C_{3-6}$ cycloalkyl group;
X represents a direct link, NH, or O;
Z is selected from

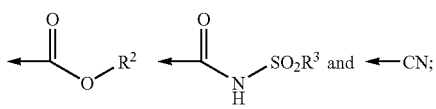

$R^2$ is H or $C_{1-6}$ alkyl (optionally substituted with 1 to 3 fluorine atoms);
$R^3$ is $C_{1-6}$ alkyl (optionally substituted with 1 to 3 fluorine atoms);
Ar is an aromatic group consisting of 1, 2 or 3 aromatic rings, which aromatic rings are independently selected from phenyl and a 5- or 6-membered heteroaromatic ring containing 1, 2, 3 or 4 heteroatoms independently selected from N, O and S, and which aromatic rings, if there are 2 or more, can be fused or linked by one or more covalent bond, and which aromatic rings are optionally substituted by 1, 2 or 3 substitutents independently selected from F, Cl, CN, OH, $C_{1-6}$ alkyl, $C_{1-6}$ alkylthio, fluoro-$C_{1-6}$ alkyl, fluoro-$C_{1-6}$ alkylthio, fluoro-$C_{1-6}$ alkoxy, $C_{1-6}$ alkoxy, $SO_2R^4$, $NR^5R^6$, $NHSO_2R^7$, $SO_2NR^8R^9$, and $NHCOR^{12}$;
$R^4$ and $R^7$ are each independently $C_{1-6}$ alkyl (optionally substituted by 1 to 3 fluorine atoms);
$R^5, R^6, R^8, R^9, R^{10}, R^{11}$ and $R^{12}$ are each independently H or $C_{1-6}$ alkyl (optionally substituted by 1 to 3 fluorine atoms);
or a pharmaceutically acceptable salt thereof.

2. A compound according to claim 1 wherein $R^1$ is a phenyl group optionally substituted by one or two substituents independently selected from F, Cl and $C_{1-4}$ alkoxy, or a $C_{3-6}$ cycloalkyl group, or a pharmaceutically acceptable salt thereof.

3. A compound according to claim 1, wherein X represents a direct link, or a pharmaceutically acceptable salt thereof.

4. A compound according to claim 1 wherein Z is

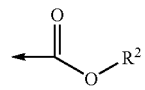

or a pharmaceutically acceptable salt thereof.

5. A compound according to claim 4, wherein $R^2$ is H, or a pharmaceutically acceptable salt thereof.

6. A compound according to claim 1, wherein Ar is a biphenyl, pyridinylphenyl, pyrimidinylphenyl or pyrazinylphenyl group, optionally substituted by 1, 2 or 3 substitutents independently selected from F, Cl, CN, OH, $C_{1-6}$ alkyl, $C_{1-6}$ alkylthio, fluoro-$C_{1-6}$ alkyl, fluoro-$C_{1-6}$ alkylthio, fluoro-$C_{1-6}$ alkoxy, $C_{1-6}$ alkoxy, $SO_2R^4$, $NR^5R^6$, $NHSO_2R^7$, $SO_2NR^8R^9$, $CONR^{10}R^{11}$ and $NHCOR^{12}$, or a pharmaceutically acceptable salt thereof.

7. A compound according to claim 6, wherein Ar is a biphenyl, pyridinylphenyl, pyrimidinylphenyl or pyrazinylphenyl optionally substituted by 1, 2 or 3 substitutents independently selected from F, Cl, CN, and a $C_{1-6}$ alkoxy group, or a pharmaceutically acceptable salt thereof.

8. A compound according to claim 1, which is a compound of formula (Ia)

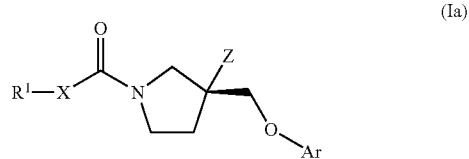

(Ia)

or a pharmaceutically acceptable salt thereof.

9. A compound according to claim 1, which is a compound of formula (Ib)

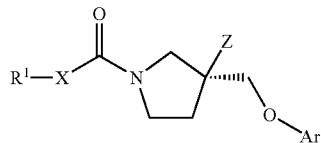

(Ib)

or a pharmaceutically acceptable salt thereof.

10. A pharmaceutical composition comprising a compound according to claim 1, or a pharmaceutically acceptable salt thereof, and a pharmaceutically acceptable diluent, carrier or adjuvant.

11. A method of treating endometriosis, uterine fibroids, menorrhagia, adenomyosis, primary dysmenorrhoea and secondary dysmenorrhoea or, chronic pelvic pain syndrome, the method comprising administering to a mammal in need thereof a therapeutically effective amount of a compound according to claim 1, or a pharmaceutically acceptable salt thereof.

12. A method according to claim 11, wherein the compound is administered as a pharmaceutical composition comprising a therapeutically effective amount of the compound or a pharmaceutically acceptable salt thereof, and a and a pharmaceutically acceptable diluent, carrier or adjuvant.

* * * * *